(12) United States Patent
Pierre et al.

(10) Patent No.: US 7,910,600 B2
(45) Date of Patent: Mar. 22, 2011

(54) THERAPEUTIC KINASE MODULATORS

(75) Inventors: Fabrice Pierre, La Jolla, CA (US); Mustapha Haddach, San Diego, CA (US)

(73) Assignee: Cylene Pharmaceuticals, Inc., San Diego, CA (US)

( * ) Notice: Subject to any disclaimer, the term of this patent is extended or adjusted under 35 U.S.C. 154(b) by 182 days.

(21) Appl. No.: 12/201,892

(22) Filed: Aug. 29, 2008

(65) Prior Publication Data

US 2009/0093465 A1    Apr. 9, 2009

Related U.S. Application Data

(60) Provisional application No. 60/969,556, filed on Aug. 31, 2007.

(51) Int. Cl.
   *A01N 43/42*   (2006.01)
   *A61K 31/44*   (2006.01)
   *C07D 471/04*  (2006.01)
(52) U.S. Cl. .......................... 514/292; 546/88
(58) Field of Classification Search .................. 514/292; 546/88
   See application file for complete search history.

(56) References Cited

U.S. PATENT DOCUMENTS

| | | | |
|---|---|---|---|
| 4,110,450 A | 8/1978 | Barreau et al. | |
| 5,624,677 A | 4/1997 | El-Rashidy et al. | |
| 5,766,863 A | 6/1998 | Godowski et al. | |
| 7,406,392 B2 | 7/2008 | Gedlinske et al. | |
| 2003/0065180 A1 | 4/2003 | Tsou et al. | |
| 2003/0069265 A1 | 4/2003 | Saxena et al. | |
| 2006/0029950 A1 | 2/2006 | Whitten et al. | |
| 2006/0074089 A1 | 4/2006 | Whitten et al. | |

FOREIGN PATENT DOCUMENTS

WO   WO-2004/007754   1/2004

OTHER PUBLICATIONS

Rewcastle, et al., Synthesis of 4-(Phenylamino)pyrimidine Derivatives as ATP-competitive Protein Kinase Inhibitors with Potential for Cancer Chemotherapy, Current Organic Chemistry, 4, 679-706 (2000).*

International Search Report and Written Opinion for PCT/US08/74820, mailed Aug. 17, 2009, 10 pages.
Rewcastle et al., Current Organic Chemistry (2000) 4:679-706.
Calebrese et al., Clin Cancer Res (2003) 9:2711-2718.
Calebrese et al., J Nat'l Cancer Inst (2004) 96(1):56-67.
Curtin, Expert Reviews in Molecular Medicine (2005) 7(4):1-20.
Di Paola et al., Eur J Pharmacology (2005) 527(1-3):163-171.
Jagtap, Nature Rev: Drug Discovery (2005) 4:421-440.
GenBank Database Accession No. NM_002019, Kommineni et al. (2008).
GenBank Database Accession No. NM_002020, Tammela et al. (2008).
GenBank Database Accession No. NM_002648, Hosgood et al. (2008).
GenBank Database Accession No. NM_004119, Paschka et al. (2008).
GenBank Database Accession No. NM_006875, Morishita et al. (2008).
GenBank Database Accession No. NP_002010, Kommineni et al. (2008).
GenBank Database Accession No. NP_002011, Tammela et al. (2008).
GenBank Database Accession No. NP_002639, Hosgood et al. (2008).
GenBank Database Accession No. NP_004110, Paschka et al. (2008).
GenBank Database Accession No. NP_006866, Morishita et al. (2008).
GenBank Database Accession No. XM_938171 (2006).
GenBank Database Accession No. XP_943264 (2006).
Li et al., Pain (2005) 115(1-2):182-190.
Parhar et al., Int J Colorectal Dis (2006) 22(6):601-609.
U.S. Appl. No. 11/849,230, filed Aug. 31, 2007 [Chua et al.].
U.S. Appl. No. 60/803,864, filed Jun. 3, 2006 [Lim et al.].
U.S. Appl. No. 60/811,990, filed Jun. 8, 2006 [Pierre et al.].
U.S. Appl. No. 60/811,992, filed Jun. 8, 2006 [Nagasawa et al.].
U.S. Appl. No. 60/904,694, filed Mar. 1, 2007 [Nagasawa et al.].
Veuger et al., Cancer Res (2003) 63:6008-6015.

* cited by examiner

*Primary Examiner* — James O Wilson
*Assistant Examiner* — Erich A Leeser
(74) *Attorney, Agent, or Firm* — Cooley LLP

(57) ABSTRACT

The invention relates in part to molecules having certain biological activities that include, but are not limited to, inhibiting cell proliferation, and modulating protein kinase activity. Molecules of the invention can modulate casein kinase (CK) activity. The invention also relates in part to methods for using such molecules.

17 Claims, No Drawings

SEQUENCE LISTING
<160> NUMBER OF SEQ ID NOS: 5
<210> SEQ ID NO 1
<211> LENGTH: 391
<212> TYPE: PRT
<213> ORGANISM: Homo sapiens
<220> FEATURE:

```
<221> NAME/KEY: DOMAIN
<222> LOCATION: (1)...(391)
<223> OTHER INFORMATION: casein kinase II alpha 1 subunit isoform a
      (NP_001886)

<400> SEQUENCE: 1
```

| | | | | | | | | | | | | | | |
|---|---|---|---|---|---|---|---|---|---|---|---|---|---|---|
| Met | Ser | Gly | Pro | Val | Pro | Ser | Arg | Ala | Arg | Val | Tyr | Thr | Asp | Val | Asn |
| 1 | | | | 5 | | | | | 10 | | | | | 15 | |

| Thr | His | Arg | Pro | Arg | Glu | Tyr | Trp | Asp | Tyr | Glu | Ser | His | Val | Val | Glu |
|---|---|---|---|---|---|---|---|---|---|---|---|---|---|---|---|
| | | | 20 | | | | | 25 | | | | | 30 | | |

| Trp | Gly | Asn | Gln | Asp | Asp | Tyr | Gln | Leu | Val | Arg | Lys | Leu | Gly | Arg | Gly |
|---|---|---|---|---|---|---|---|---|---|---|---|---|---|---|---|
| | | 35 | | | | | 40 | | | | | 45 | | | |

| Lys | Tyr | Ser | Glu | Val | Phe | Glu | Ala | Ile | Asn | Ile | Thr | Asn | Asn | Glu | Lys |
|---|---|---|---|---|---|---|---|---|---|---|---|---|---|---|---|
| | 50 | | | | | 55 | | | | | 60 | | | | |

| Val | Val | Val | Lys | Ile | Leu | Lys | Pro | Val | Lys | Lys | Lys | Lys | Ile | Lys | Arg |
|---|---|---|---|---|---|---|---|---|---|---|---|---|---|---|---|
| 65 | | | | | 70 | | | | | 75 | | | | | 80 |

| Glu | Ile | Lys | Ile | Leu | Glu | Asn | Leu | Arg | Gly | Gly | Pro | Asn | Ile | Ile | Thr |
|---|---|---|---|---|---|---|---|---|---|---|---|---|---|---|---|
| | | | | 85 | | | | | 90 | | | | | 95 | |

| Leu | Ala | Asp | Ile | Val | Lys | Asp | Pro | Val | Ser | Arg | Thr | Pro | Ala | Leu | Val |
|---|---|---|---|---|---|---|---|---|---|---|---|---|---|---|---|
| | | | 100 | | | | | 105 | | | | | 110 | | |

| Phe | Glu | His | Val | Asn | Asn | Thr | Asp | Phe | Lys | Gln | Leu | Tyr | Gln | Thr | Leu |
|---|---|---|---|---|---|---|---|---|---|---|---|---|---|---|---|
| | | 115 | | | | | 120 | | | | | 125 | | | |

| Thr | Asp | Tyr | Asp | Ile | Arg | Phe | Tyr | Met | Tyr | Glu | Ile | Leu | Lys | Ala | Leu |
|---|---|---|---|---|---|---|---|---|---|---|---|---|---|---|---|
| | 130 | | | | | 135 | | | | | 140 | | | | |

| Asp | Tyr | Cys | His | Ser | Met | Gly | Ile | Met | His | Arg | Asp | Val | Lys | Pro | His |
|---|---|---|---|---|---|---|---|---|---|---|---|---|---|---|---|
| 145 | | | | | 150 | | | | | 155 | | | | | 160 |

| Asn | Val | Met | Ile | Asp | His | Glu | His | Arg | Lys | Leu | Arg | Leu | Ile | Asp | Trp |
|---|---|---|---|---|---|---|---|---|---|---|---|---|---|---|---|
| | | | | 165 | | | | | 170 | | | | | 175 | |

| Gly | Leu | Ala | Glu | Phe | Tyr | His | Pro | Gly | Gln | Glu | Tyr | Asn | Val | Arg | Val |
|---|---|---|---|---|---|---|---|---|---|---|---|---|---|---|---|
| | | | 180 | | | | | 185 | | | | | 190 | | |

| Ala | Ser | Arg | Tyr | Phe | Lys | Gly | Pro | Glu | Leu | Leu | Val | Asp | Tyr | Gln | Met |
|---|---|---|---|---|---|---|---|---|---|---|---|---|---|---|---|
| | | 195 | | | | | 200 | | | | | 205 | | | |

| Tyr | Asp | Tyr | Ser | Leu | Asp | Met | Trp | Ser | Leu | Gly | Cys | Met | Leu | Ala | Ser |
|---|---|---|---|---|---|---|---|---|---|---|---|---|---|---|---|
| | 210 | | | | | 215 | | | | | 220 | | | | |

| Met | Ile | Phe | Arg | Lys | Glu | Pro | Phe | Phe | His | Gly | His | Asp | Asn | Tyr | Asp |
|---|---|---|---|---|---|---|---|---|---|---|---|---|---|---|---|
| 225 | | | | | 230 | | | | | 235 | | | | | 240 |

| Gln | Leu | Val | Arg | Ile | Ala | Lys | Val | Leu | Gly | Thr | Glu | Asp | Leu | Tyr | Asp |
|---|---|---|---|---|---|---|---|---|---|---|---|---|---|---|---|
| | | | | 245 | | | | | 250 | | | | | 255 | |

| Tyr | Ile | Asp | Lys | Tyr | Asn | Ile | Glu | Leu | Asp | Pro | Arg | Phe | Asn | Asp | Ile |
|---|---|---|---|---|---|---|---|---|---|---|---|---|---|---|---|
| | | | 260 | | | | | 265 | | | | | 270 | | |

| Leu | Gly | Arg | His | Ser | Arg | Lys | Arg | Trp | Glu | Arg | Phe | Val | His | Ser | Glu |
|---|---|---|---|---|---|---|---|---|---|---|---|---|---|---|---|
| | | 275 | | | | | 280 | | | | | 285 | | | |

| Asn | Gln | His | Leu | Val | Ser | Pro | Glu | Ala | Leu | Asp | Phe | Leu | Asp | Lys | Leu |
|---|---|---|---|---|---|---|---|---|---|---|---|---|---|---|---|
| | 290 | | | | | 295 | | | | | 300 | | | | |

| Leu | Arg | Tyr | Asp | His | Gln | Ser | Arg | Leu | Thr | Ala | Arg | Glu | Ala | Met | Glu |
|---|---|---|---|---|---|---|---|---|---|---|---|---|---|---|---|
| 305 | | | | | 310 | | | | | 315 | | | | | 320 |

| His | Pro | Tyr | Phe | Tyr | Thr | Val | Val | Lys | Asp | Gln | Ala | Arg | Met | Gly | Ser |
|---|---|---|---|---|---|---|---|---|---|---|---|---|---|---|---|
| | | | | 325 | | | | | 330 | | | | | 335 | |

| Ser | Ser | Met | Pro | Gly | Gly | Ser | Thr | Pro | Val | Ser | Ser | Ala | Asn | Met | Met |
|---|---|---|---|---|---|---|---|---|---|---|---|---|---|---|---|
| | | | 340 | | | | | 345 | | | | | 350 | | |

| Ser | Gly | Ile | Ser | Ser | Val | Pro | Thr | Pro | Ser | Pro | Leu | Gly | Pro | Leu | Ala |
|---|---|---|---|---|---|---|---|---|---|---|---|---|---|---|---|
| | | 355 | | | | | 360 | | | | | 365 | | | |

| Gly | Ser | Pro | Val | Ile | Ala | Ala | Ala | Asn | Pro | Leu | Gly | Met | Pro | Val | Pro |
|---|---|---|---|---|---|---|---|---|---|---|---|---|---|---|---|
| | 370 | | | | | 375 | | | | | 380 | | | | |

| Ala | Ala | Ala | Gly | Ala | Gln | Gln |
|---|---|---|---|---|---|---|

```
385                390
```

<210> SEQ ID NO 2
<211> LENGTH: 391
<212> TYPE: PRT
<213> ORGANISM: Homo sapiens
<220> FEATURE:
<221> NAME/KEY: DOMAIN
<222> LOCATION: (1)...(391)
<223> OTHER INFORMATION: casein kinase II alpha 1 subunit isoform a
      (NP_808227)

<400> SEQUENCE: 2

```
Met Ser Gly Pro Val Pro Ser Arg Ala Arg Val Tyr Thr Asp Val Asn
 1               5                  10                  15

Thr His Arg Pro Arg Glu Tyr Trp Asp Tyr Glu Ser His Val Val Glu
            20                  25                  30

Trp Gly Asn Gln Asp Asp Tyr Gln Leu Val Arg Lys Leu Gly Arg Gly
        35                  40                  45

Lys Tyr Ser Glu Val Phe Glu Ala Ile Asn Ile Thr Asn Asn Glu Lys
50                  55                  60

Val Val Val Lys Ile Leu Lys Pro Val Lys Lys Lys Lys Ile Lys Arg
65                  70                  75                  80

Glu Ile Lys Ile Leu Glu Asn Leu Arg Gly Gly Pro Asn Ile Ile Thr
                85                  90                  95

Leu Ala Asp Ile Val Lys Asp Pro Val Ser Arg Thr Pro Ala Leu Val
            100                 105                 110

Phe Glu His Val Asn Asn Thr Asp Phe Lys Gln Leu Tyr Gln Thr Leu
        115                 120                 125

Thr Asp Tyr Asp Ile Arg Phe Tyr Met Tyr Glu Ile Leu Lys Ala Leu
130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
                165                 170                 175

Gly Leu Ala Glu Phe Tyr His Pro Gly Gln Glu Tyr Asn Val Arg Val
            180                 185                 190

Ala Ser Arg Tyr Phe Lys Gly Pro Glu Leu Leu Val Asp Tyr Gln Met
        195                 200                 205

Tyr Asp Tyr Ser Leu Asp Met Trp Ser Leu Gly Cys Met Leu Ala Ser
210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
                245                 250                 255

Tyr Ile Asp Lys Tyr Asn Ile Glu Leu Asp Pro Arg Phe Asn Asp Ile
            260                 265                 270

Leu Gly Arg His Ser Arg Lys Arg Trp Glu Arg Phe Val His Ser Glu
        275                 280                 285

Asn Gln His Leu Val Ser Pro Glu Ala Leu Asp Phe Leu Asp Lys Leu
290                 295                 300

Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
                325                 330                 335

Ser Ser Met Pro Gly Gly Ser Thr Pro Val Ser Ser Ala Asn Met Met
            340                 345                 350
```

```
Ser Gly Ile Ser Ser Val Pro Thr Pro Ser Pro Leu Gly Pro Leu Ala
        355                 360                 365

Gly Ser Pro Val Ile Ala Ala Asn Pro Leu Gly Met Pro Val Pro
370                 375                 380

Ala Ala Ala Gly Ala Gln Gln
385                 390

<210> SEQ ID NO 3
<211> LENGTH: 255
<212> TYPE: PRT
<213> ORGANISM: Homo sapiens
<220> FEATURE:
<221> NAME/KEY: DOMAIN
<222> LOCATION: (1)...(255)
<223> OTHER INFORMATION: casein kinase II alpha 1 subunit isoform b
      (NP_808228)

<400> SEQUENCE: 3

Met Tyr Glu Ile Leu Lys Ala Leu Asp Tyr Cys His Ser Met Gly Ile
  1               5                  10                  15

Met His Arg Asp Val Lys Pro His Asn Val Met Ile Asp His Glu His
             20                  25                  30

Arg Lys Leu Arg Leu Ile Asp Trp Gly Leu Ala Glu Phe Tyr His Pro
         35                  40                  45

Gly Gln Glu Tyr Asn Val Arg Val Ala Ser Arg Tyr Phe Lys Gly Pro
     50                  55                  60

Glu Leu Leu Val Asp Tyr Gln Met Tyr Asp Tyr Ser Leu Asp Met Trp
 65                  70                  75                  80

Ser Leu Gly Cys Met Leu Ala Ser Met Ile Phe Arg Lys Glu Pro Phe
                 85                  90                  95

Phe His Gly His Asp Asn Tyr Asp Gln Leu Val Arg Ile Ala Lys Val
            100                 105                 110

Leu Gly Thr Glu Asp Leu Tyr Asp Tyr Ile Asp Lys Tyr Asn Ile Glu
        115                 120                 125

Leu Asp Pro Arg Phe Asn Asp Ile Leu Gly Arg His Ser Arg Lys Arg
    130                 135                 140

Trp Glu Arg Phe Val His Ser Glu Asn Gln His Leu Val Ser Pro Glu
145                 150                 155                 160

Ala Leu Asp Phe Leu Asp Lys Leu Leu Arg Tyr Asp His Gln Ser Arg
                165                 170                 175

Leu Thr Ala Arg Glu Ala Met Glu His Pro Tyr Phe Tyr Thr Val Val
            180                 185                 190

Lys Asp Gln Ala Arg Met Gly Ser Ser Ser Met Pro Gly Gly Ser Thr
        195                 200                 205

Pro Val Ser Ser Ala Asn Met Met Ser Gly Ile Ser Ser Val Pro Thr
    210                 215                 220

Pro Ser Pro Leu Gly Pro Leu Ala Gly Ser Pro Val Ile Ala Ala Ala
225                 230                 235                 240

Asn Pro Leu Gly Met Pro Val Pro Ala Ala Ala Gly Ala Gln Gln
                245                 250                 255

<210> SEQ ID NO 4
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
```

```
<222> LOCATION: (1)...(10)
<223> OTHER INFORMATION: substrate peptide

<400> SEQUENCE: 4

Arg Arg Arg Asp Asp Asp Ser Asp Asp Asp
1               5                   10

<210> SEQ ID NO 5
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: substrate peptide

<400> SEQUENCE: 5

Lys Lys Arg Asn Arg Thr Leu Thr Lys
1               5
```

THERAPEUTIC KINASE MODULATORS

CROSS-REFERENCE TO RELATED APPLICATIONS

This application claims priority under 35 U.S.C. §119(e) to U.S. Provisional Application Ser. No. 60/969,556 filed Aug. 31, 2007. The content of this document is incorporated herein by reference in its entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 532232004100Seqlist.txt | Oct. 31, 2008 | 9,866 bytes |

FIELD OF THE INVENTION

The invention relates in part to molecules having certain biological activities that include, but are not limited to, inhibiting cell proliferation, and modulating serine-threonine protein kinase activity. Molecules of the invention can modulate casein kinase (CK) activity (e.g., CK2 activity). The invention also relates in part to methods for using such molecules.

DISCLOSURE OF THE INVENTION

The present invention in part provides chemical compounds having certain biological activities that include, but are not limited to, inhibiting cell proliferation, inhibiting angiogenesis, modulating protein kinase activity and modulating polymerase activity. Certain molecules can modulate casein kinase 2 (CK2) activity and can affect biological functions that include but are not limited to, inhibiting gamma phosphate transfer from ATP to a protein or peptide substrate, inhibiting angiogenesis, inhibiting cell proliferation and inducing cell apoptosis, for example. The present invention also in part provides methods for preparing novel chemical compounds, and analogs thereof, and methods of using the foregoing. Also provided are compositions comprising the above-described molecules in combination with other agents, and methods for using such molecules in combination with other agents.

The compounds of the invention have the general formula (A):

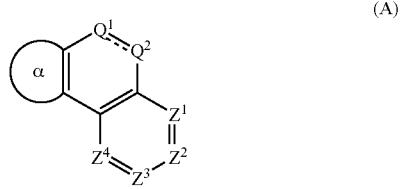

(A)

wherein the group labeled α represents a 5-6 membered aromatic or heteroaromatic ring fused onto the ring containing $Q^1$, wherein α is a 6-membered aryl ring optionally containing one or more nitrogen atoms as ring members, or a five membered aryl ring selected from thiophene and thiazole;

$Q^1$ is C—$R^{10}$, $Q^2$ is N, and the bond between $Q^1$ and $Q^2$ is a double bond; and wherein $Z^1$-$Z^4$ and $R^{10}$ are as defined below for Formula (I).

The invention also includes the pharmaceutically acceptable salts of compounds of formula (A). Thus in each compound of the invention, Formula (A) represents a fused tricyclic ring system which is linked through $Q^1$ to a group $R^{10}$, which is further described below.

Compounds related to Formula (A), wherein $Q^1$ is carbon substituted with various groups connected through a heteroatom have been previously disclosed by the present applicants in U.S. application Ser. No. 11/849,230, to Chua et al., which was filed Aug. 31, 2007, and is entitled SERINE-THREONINE PROTEIN KINASE AND PARP MODULATORS. In the present invention, it has surprisingly been found that compounds of Formula (A) wherein the group attached to $Q^1$ is not connected through a heteroatom provide unexpectedly beneficial results.

In one aspect, the invention provides compounds of Formula (I):

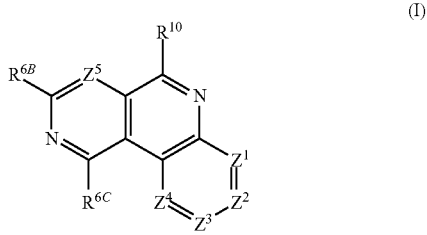

(I)

and pharmaceutically acceptable salts, esters, prodrugs and tautomers thereof; wherein:

each $Z^1$, $Z^2$, $Z^3$, and $Z^4$ is N, CH, or $CR^3$, provided that none, one or two of $Z^1$, $Z^2$, $Z^3$, and $Z^4$ are N; and further provided that one or more of $Z^1$, $Z^2$, $Z^3$, and $Z^4$ is $CR^3$;

each $R^3$ is independently an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^3$ is independently halo, $CF_3$, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, COOH, polar substituent, carboxy bioisostere, $CONR_2$, OOCR, COR, or $NO_2$;

$Z^5$ is $CR^{6A}$ or N;

each of $R^{6A}$, $R^{6B}$ and $R^{6C}$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each of $R^{6A}$, $R^{6B}$ and $R^{6C}$ can be halo, $CF_3$, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, $CONR_2$, OOCR, COR, or $NO_2$;

wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S; and $R^{10}$ is an optionally substituted five-membered or six-membered carbocyclic or heterocyclic aromatic ring.

In compounds of Formula (I), $Z^5$ is N or $CR^{6A}$, such that the ring containing $Z^5$ is independently an optionally substituted pyridine or pyrimidine ring. For example, one or more ring nitrogen atoms within the ring containing $Z^5$ may be arranged as follows:

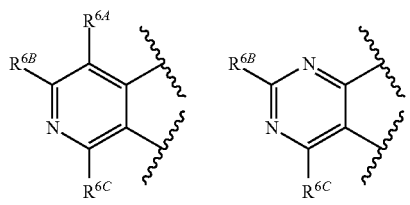

where each of $R^{6A}$, $R^{6B}$, and $R^{6C}$ is independently selected from the $R^6$ substituents defined above with respect to compounds of Formula (I).

In compounds of Formula (I), each of $Z^1$, $Z^2$, $Z^3$, and $Z^4$ is N, CH, or $CR^3$, provided that none, one or two of $Z^1$, $Z^2$, $Z^3$, and $Z^4$ are N; and further provided that one or more of $Z^1$, $Z^2$, $Z^3$, and $Z^4$ is $CR^3$, where each $R^3$ is independently selected from the $R^3$ substituents defined above with respect to compounds of Formula (I).

In certain embodiments, at least one of $Z^1$, $Z^2$, $Z^3$, and $Z^4$ is a nitrogen atom. One or more ring nitrogen atoms can be positioned in the ring containing $Z^1$, $Z^2$, $Z^3$, and $Z^4$ such that each ring is independently an optionally substituted pyridine, pyrimidine or pyridazine ring. In other embodiments, each of $Z^1$, $Z^2$, $Z^3$, and $Z^4$ is $CR^3$, where each $R^3$ is independently selected from the $R^3$ substituents defined above with respect to compounds of Formula (I). In further embodiments, one or more of $Z^1$, $Z^2$, $Z^3$, and $Z^4$ is $CR^3$, and the others are CH. In specific embodiments, one of $Z^1$, $Z^2$, $Z^3$, and $Z^4$ is $CR^4$, and the others are CH. In certain preferred embodiments, $Z^2$ is $CR^3$ and $Z^1$, $Z^3$, and $Z^4$ are CH.

In certain embodiments, at least one $R^3$ substituent is a polar substituent, such as a carboxylic acid or a salt, an ester or a bioisostere thereof. In some embodiments, at least one $R^3$ is a carboxylic acid-containing substituent or a carboxylate bioisostere, or a salt or ester thereof, for example. In certain embodiments, at least one $R^3$ is a carboxylic acid, carboxylate salt, ester, carboxamide, tetrazole or other carboxy bioisostere. In specific embodiments, at least one $R^3$ is a carboxylic acid-containing substituent or a salt thereof. This polar substituent is sometimes referred to herein as $R^{3P}$.

The term "polar substituent" as used herein refers to any substituent having an electric dipole, and optionally a dipole moment (e.g., an asymmetrical polar substituent has a dipole moment and a symmetrical polar substituent does not have a dipole moment). Polar substituents include substituents that accept or donate a hydrogen bond, and groups that would carry at least a partial positive or negative charge in aqueous solution at physiological pH levels. In certain embodiments, a polar substituent is one that can accept or donate electrons in a non-covalent hydrogen bond with another chemical moiety. In certain embodiments, a polar substituent is selected from a carboxy, a carboxy bioisostere or other acid-derived moiety that exists predominately as an anion at a pH of about 7 to 8. Other polar substituents include, but are not limited to, groups containing an OH or NH, an ether oxygen, an amine nitrogen, an oxidized sulfur or nitrogen, a carbonyl, a nitrile, and a nitrogen-containing or oxygen-containing heterocyclic ring whether aromatic or non-aromatic. In some embodiments, the polar substituent represented by $R^3$ is a carboxylate or a carboxylate bioisostere.

"Carboxylate bioisostere" or "carboxy bioisostere" as used herein refers to a moiety that is expected to be negatively charged to a substantial degree at physiological pH. In certain embodiments, the carboxylate bioisostere is a moiety selected from the group consisting of:

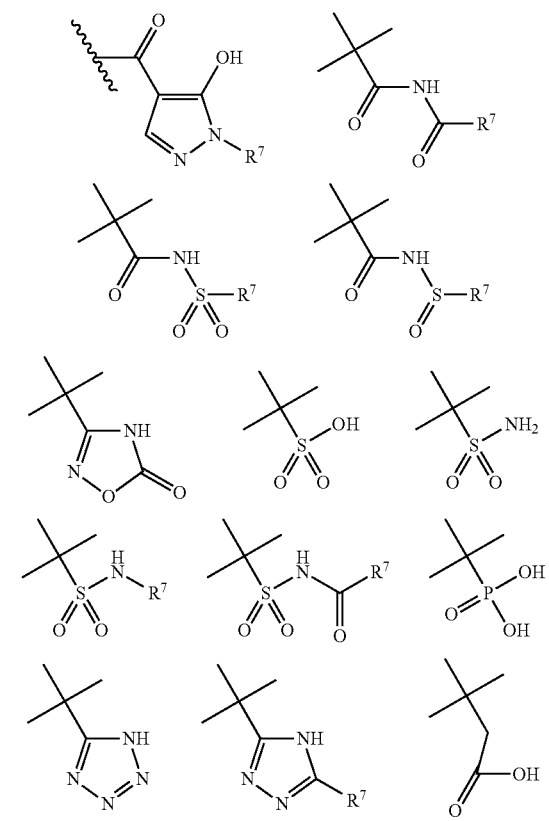

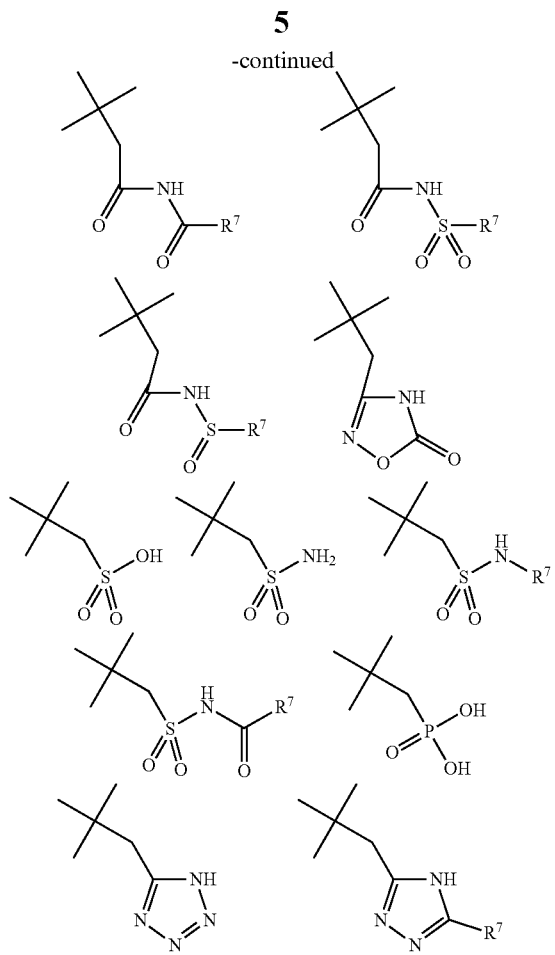

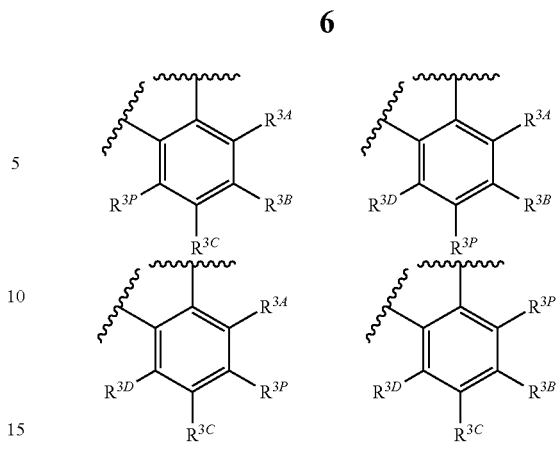

where $R^{3P}$ is a polar substituent and each $R^{3A}$, $R^{3B}$, $R^{3C}$ and $R^{3D}$ is H or is independently selected from the $R^3$ substituents, as defined above with respect to compounds of Formula (I).

In specific embodiments, one of $Z^1$-$Z^4$ is $CR^3$ and the others of $Z^1$-$Z^4$ are CH, where $R^3$ is a polar substituent (i.e., $R^{3P}$), for example, a carboxylate or carboxylic acid, ester, or amide, or a tetrazole, arranged at any one of the positions in the ring containing $Z^1$-$Z^4$:

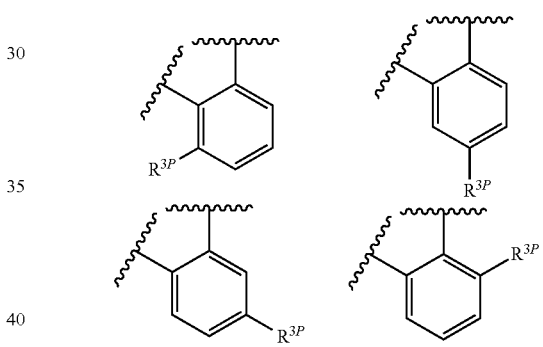

and salts and prodrugs of the foregoing, wherein each $R^7$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic ring; or $R^7$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring.

In certain embodiments, the polar substituent is selected from the group consisting of carboxylic acid, carboxylic ester, carboxamide, tetrazole, triazole, carboxymethanesulfonamide, oxadiazole, oxathiadiazole, thiazole, aminothiazole and hydroxythiazole.

In some embodiments, at least one $R^3$ present is a carboxylic acid or a salt, or ester or a bioisostere thereof. In certain embodiments, at least one $R^3$ present is a carboxylic acid-containing substituent or a salt, ester or bioisostere thereof. In the latter embodiments, the $R^3$ substituent may be a C1-C10 alkyl or C2-C10 alkenyl linked to a carboxylic acid (or salt, ester or bioisostere thereof), for example, and in some embodiments, the $R^3$ substituent is not $NHCOOCH_2CH_3$.

A polar substituent may be at any position on the ring containing $Z^1$-$Z^4$ in Formula (I), and the ring may include one, two, three or four polar substituents. In certain embodiments, at least one of $Z^1$-$Z^4$ may be $CR^3$ and one of the $R^3$ substituents may be a polar substituent (e.g., a carboxylate or carboxylic acid ester, or a tetrazole) arranged at any one of the positions in the ring containing $Z^1$-$Z^4$:

The polar substituent represented by $R^3$ in some embodiments is a carboxy (e.g., COOH), carboxyalkyl (e.g., carboxymethyl), tetrazole or amide (e.g., —$CONH_2$, —CONHc-Pr) substituent. In other embodiments, $R^3$ represents a carboxylate bioisostere. In preferred embodiments, $R^3$ at position $Z^2$ is a carboxylic acid-containing substituent or a carboxylate bioisostere, or a salt or ester thereof. In specific embodiments, $Z^2$ is $CR^3$, where $R^3$ is COOH or COOMe. In other embodiments, it is $CONR_2$, where each R is independently H or $C_{1-4}$ alkyl; sometimes, it is $CONH_2$ or CONHc-Pr.

In compounds of Formula (I), $R^{10}$ is an optionally substituted five-membered or six-membered carbocyclic or heterocyclic aromatic ring. In certain embodiments, $R^{10}$ is an optionally substituted six-membered carbocyclic or heterocyclic aromatic ring. In some such embodiments, the optionally substituted six-membered carbocyclic or heterocyclic aromatic ring is selected from phenyl, pyridine, pyridazine, pyrimidine, pyrazine, triazine, pyran, and optionally substituted variants of the foregoing. In particular embodiments, $R^{10}$ is an optionally substituted phenyl or pyridyl ring. In some embodiments, it is an unsubstituted phenyl ring. In other embodiments, $R^{10}$ is phenyl substituted with one or more halo, CN, $C_{1-4}$ alkyl, $C_{1-4}$ alkoxy, $NH_2$, or NHAc substitutents.

In other embodiments, $R^{10}$ is an optionally substituted five-membered heterocyclic aromatic ring. In some such embodiments, the optionally substituted five-membered heterocyclic aromatic ring is selected from pyrrole, imidazole, pyrazole, triazole, tetrazole, thiophene, thiazole, thiadiazole, isothiazole, furan, oxazole, isoxazole, oxadiazole and optionally substituted variants thereof. In particular embodiments, $R^{10}$ is an optionally substituted pyrazole, isoxazole or thiophene; in specific embodiments, it is an $N^1$-methyl-pyrazol-4-yl substituent or an optionally substituted 2- or 3-thiophene substituent. In certain embodiments, optional substituents when present on a five-membered heterocyclic aromatic ring include one or more halo, CN, or $C_{1-4}$ alkyl groups.

Each of $R^{6B}$, $R^{6C}$ and $R^{6A}$, where present, is independently selected from the list defined above with respect to compounds of Formula (I). In certain embodiments, at least one of $R^{6B}$ and $R^{6C}$ is H. In other embodiments, both $R^{6B}$ and $R^{6C}$ are H. In some embodiments, $R^{6B}$ is thiomethoxy (—SMe) and $R^{6C}$ is H. In certain embodiments, $Z^5$ is N, and $R^{6B}$ is SR, $SO_2R$, or $NR_2$, where each R is independently H or $C_{1-4}$ alkyl; in some such embodiments, $R^{6B}$ is SMe, $SO_2Me$ or NHc-Pr. In other embodiments, $Z^5$ is $R^{6A}$, and each of $R^{6A}$, $R^{6B}$ and $R^{6C}$ is H.

In another aspect, the invention provides compounds of Formula (II):

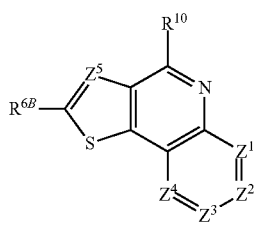

Formula (II)

and pharmaceutically acceptable salts, esters, prodrugs and tautomers thereof; wherein:
each $Z^1$, $Z^2$, $Z^3$, and $Z^4$ is N, CH, or $CR^3$, provided that none, one or two of $Z^1$, $Z^2$, $Z^3$, and $Z^4$ are N; and further provided that one or more of $Z^1$, $Z^2$, $Z^3$, and $Z^4$ is $CR^3$;
each $R^3$ is independently an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or
each $R^3$ is independently halo, $CF_3$, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, COOH, polar substituent, carboxy bioisostere, $CONR_2$, OOCR, COR, or $NO_2$;
$Z^5$ is $CR^{6A}$ or N;
each of $R^{6A}$ and $R^{6B}$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group,
or each of $R^{6A}$ and $R^{6B}$ can be halo, $CF_3$, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, $CONR_2$, OOCR, COR, or $NO_2$;

wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl,
and wherein two R on the same atom or on adjacent atoms can be linked to form a 3-8 membered ring, optionally containing one or more N, O or S;
and each R group, and each ring formed by linking two R groups together, is optionally substituted with one or more substituents selected from halo, =O, =N—CN, =N—OR', =NR', OR', NR'$_2$, SR', $SO_2R'$, $SO_2NR'_2$, NR'$SO_2R'$, NR'$CONR'_2$, NR'COOR', NR'COR', CN, COOR', CONR'$_2$, OOCR', COR', and $NO_2$,
wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;
and wherein two R' can be linked to form a 3-7 membered ring optionally containing up to three heteroatoms selected from N, O and S; and
$R^{10}$ is an optionally substituted five-membered or six-membered carbocyclic or heterocyclic aromatic ring.

Embodiments described with respect to compounds of Formula (I) for substituents $Z^1$, $Z^2$, $Z^3$, $Z^4$, $Z^5$, $R^{6A}$, $R^{6B}$, $R^3$ and $R^{10}$ may also be applied to compounds of Formula (II).

In compounds of Formula (II), $Z^5$ is N or $CR^{6A}$, such that the ring containing $Z^5$ is independently an optionally substituted thiophene or thiazole ring. For example, one or more heteroatoms within the ring containing $Z^5$ may be arranged as follows:

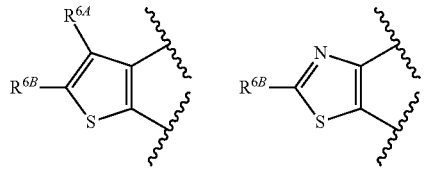

where each of $R^{6A}$ and $R^{6B}$ are independently selected from the $R^6$ substituents defined above with respect to compounds of Formula (II).

In compounds of Formula (II), each of $Z^1$, $Z^2$, $Z^3$, and $Z^4$ is N, CH, or $CR^3$, provided that none, one or two of $Z^1$, $Z^2$, $Z^3$, and $Z^4$ are N; and further provided that one or more of $Z^1$, $Z^3$, and $Z^4$ is $CR^3$, where each $R^3$ is independently selected from the $R^3$ substituents defined above with respect to compounds of Formula (I) or (II).

In certain embodiments, at least one of $Z^1$-$Z^4$ is a nitrogen atom. One or more ring nitrogen atoms can be positioned in the ring containing $Z^1$-$Z^4$ such that each ring is independently an optionally substituted pyridine, pyrimidine or pyridazine ring. In other embodiments, each of $Z^1$, $Z^2$, $Z^3$ and $Z^4$ is $CR^3$, where each $R^3$ is independently selected from the $R^3$ substituents defined above with respect to compounds of Formula (II). In further embodiments, at least one of $Z^1$, $Z^2$, $Z^3$ and $Z^4$ is $CR^3$, and the others are CH. In other embodiments, one of $Z^1$, $Z^2$, $Z^3$ and $Z^4$ is $CR^3$, and the others are CH. In some such embodiments, $Z^2$ is $CR^3$, and $Z^1$, $Z^3$ and $Z^4$ are CH.

In certain embodiments of Formula (II), at least one $R^3$ substituent is a polar substituent, such as a carboxylic acid or a salt, an ester or a bioisostere thereof. In compounds of Formula (II), a polar substituent may be at any position on the ring containing $Z^1$-$Z^4$, and the ring may include one, two, three or four polar substituents. In certain embodiments, at least one of $Z^1$-$Z^4$ may be $CR^3$ and one of the $R^3$ substituents may be a polar substituent (e.g., a carboxylate or carboxylic acid ester, or a tetrazole) arranged at any one of the positions in the ring, as described for compounds of Formula (I). In certain embodiments of Formula (II), at least one $R^3$ is a carboxylic acid-containing substituent or a carboxylate bioisostere, or a salt or ester thereof, for example. In some embodiments, at least one $R^3$ is a carboxylic acid-containing substituent or a salt thereof.

In compounds of Formula (II), $R^{10}$ is an optionally substituted five-membered or six-membered carbocyclic or heterocyclic aromatic ring. In certain embodiments of Formula (II), $R^{10}$ is an optionally substituted six-membered carbocyclic or heterocyclic aromatic ring. In some such embodiments, the optionally substituted six-membered carbocyclic or heterocyclic aromatic ring is selected from phenyl, pyridine, pyridazine, pyrimidine, pyrazine, triazine, pyran, and optionally substituted variants of the foregoing. In certain embodiments, $R^{10}$ is an optionally substituted phenyl ring.

In other embodiments of Formula (II), $R^{10}$ is an optionally substituted five-membered heterocyclic aromatic ring. In some such embodiments, the optionally substituted five-membered heterocyclic aromatic ring is selected from pyrrole, imidazole, pyrazole, triazole, tetrazole, thiophene, thiazole, thiadiazole, isothiazole, furan, oxazole, isoxazole, oxadiazole and optionally substituted variants thereof.

Each of $R^{6B}$ and $R^{6A}$, where present, is independently selected from the list defined above with respect to compounds of Formula (II). In certain embodiments, at least one of $R^{6A}$ and $R^{6B}$ is H. In other embodiments, both $R^{6A}$ and $R^{6B}$ are H. In other embodiments, $R^{6B}$ is halo or $NR_2$. In certain embodiments, $Z^5$ is $CR^{6A}$, where $R^{6A}$ is H, and $R^{6B}$ is H or halo. In other embodiments, $Z^5$ is N, and $R^{6B}$ is H or $NR_2$.

Also provided herein are compounds for formula (I) having the structures of formulae (III), (IV), (V) and (VI):

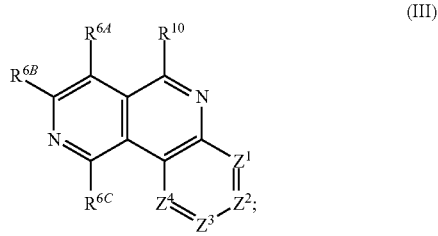

(III)

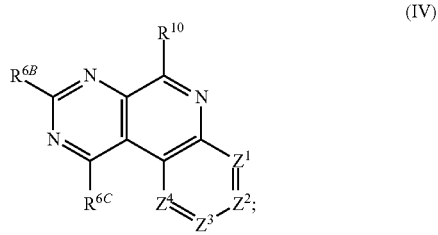

(IV)

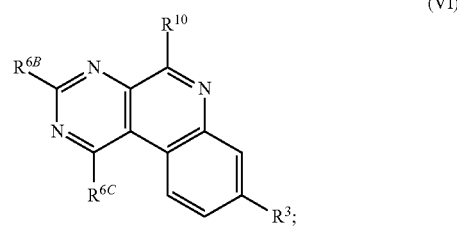

(V)

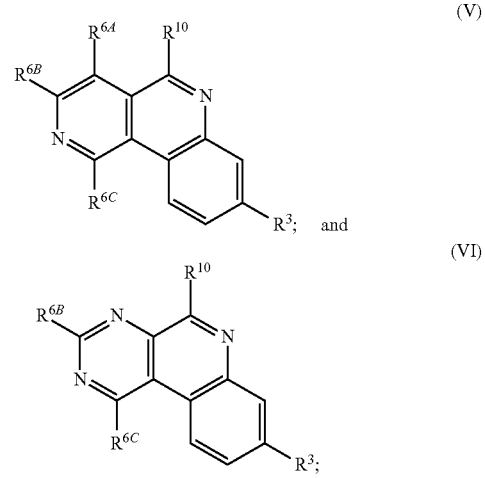

(VI)

and pharmaceutically acceptable salts, esters, and tautomers thereof;

wherein $R^{6A}$, $R^{6B}$, $R^{6C}$, $R^{10}$, $Z^1$, $Z^2$, $Z^3$, $Z^4$ and $R^3$ are defined as for Formula (I).

In compounds of Formula (III) and (IV), each of $Z^1$, $Z^2$, $Z^3$, and $Z^4$ is N, CH, or $CR^3$, provided that none, one or two of $Z^1$, $Z^2$, $Z^3$, and $Z^4$ are N; and further provided that one or more of $Z^1$, $Z^2$, $Z^3$, and $Z^4$ is $CR^3$, where each $R^3$ is independently selected from the $R^3$ substituents defined above with respect to compounds of Formula (I).

In certain embodiments of Formula (III) or (IV), at least one of $Z^1$, $Z^2$, $Z^3$, and $Z^4$ is a nitrogen atom. In further embodiments, one or more of $Z^1$, $Z^2$, $Z^3$, and $Z^4$ is $CR^3$, and the others are CH. In specific embodiments, one of $Z^1$, $Z^2$, $Z^3$, and $Z^4$ is $CR^3$, and the others are CH. In certain preferred embodiments, $Z^2$ is $CR^3$ and $Z^1$, $Z^3$, and $Z^4$ are CH.

In certain embodiments of Formula (III), (IV), (V) and (VI), at least one $R^3$ substituent is a polar substituent, such as a carboxylic acid or a salt, an ester or a bioisostere thereof. In some embodiments, at least one $R^3$ is a carboxylic acid-containing substituent or a carboxylate bioisostere, or a salt or ester thereof, for example. In certain embodiments, at least one $R^3$ is a carboxylic acid-containing substituent or a salt thereof. In some embodiments, $R^3$ at position $Z^2$ is COOH, $COOR$ or $CONR_2$, where each R is independently H or $C_{1-4}$ alkyl. In specific embodiments, $R^3$ at position $Z^2$ is COOH, COOMe or CONHc-Pr. In other embodiments, $Z^2$ is $CR^3$ where $R^3$ is F.

In compounds of Formula (III), (IV), (V) and (VI), $R^{10}$ is an optionally substituted five-membered heterocyclic aromatic ring or six-membered carbocyclic or heterocyclic aromatic ring. In certain embodiments, $R^{10}$ is an optionally substituted phenyl or pyridine ring. In some embodiments, it is an unsubstituted phenyl ring. In other embodiments, $R^{10}$ is phenyl substituted with one or more halo, CN, $C_{1-4}$ alkyl, $C_{1-4}$ alkoxy, $NH_2$, or NHAc substitutents. In certain embodiments, $R^{10}$ is an optionally substituted five-membered heterocyclic aromatic ring.

In some such embodiments, $R^{10}$ is an optionally substituted pyrazole, isoxazole or thiophene ring.

Each of $R^{6A}$, $R^{6B}$, and $R^{6C}$, where present in compounds of Formula (III), (IV), (V) and (VI) is independently selected from the list defined above with respect to compounds of Formula (I). In certain embodiments, at least one of $R^{6B}$ and $R^{6C}$ is H. In other embodiments, both $R^{6B}$ and $R^{6C}$ are H. In certain embodiments of Formula (IV) and (VI), $R^{6B}$ is SR, $SO_2R$, or $NR_2$, where each R is independently H or $C_{1-4}$ alkyl; in some such embodiments, $R^{6B}$ is SMe, $SO_2Me$ or NHc-Pr. In other embodiments of Formula (III) and (V), $R^{6A}$, $R^{6B}$ and $R^{6C}$ are H.

Other embodiments described herein with respect to compounds of Formula (I) also may be applied to compounds of Formula (III), Formula (IV), Formula (V) and Formula (VI).

Also provided herein is a pharmaceutical composition comprising a compound of Formula (A), Formula (I), Formula (II), Formula (III), Formula (IV), Formula (V), or Formula (VI), as described herein and a pharmaceutically acceptable carrier or excipient. Pharmaceutical compositions can be utilized in treatments described herein.

Provided also are methods for identifying a candidate molecule that interacts with a CK2 protein, which comprise: contacting a composition containing a CK2 protein and a compound described herein with a candidate molecule under conditions in which the compound and the protein interact, and determining whether the amount of the compound that interacts with the protein is modulated relative to a control interaction between the compound and the protein without the candidate molecule, whereby a candidate molecule that modulates the amount of the compound interacting with the protein relative to the control interaction is identified as a candidate molecule that interacts with the protein.

In certain embodiments, the protein is a CK2 protein, such as a CK2 protein comprising the amino acid sequence of SEQ ID NO: 1, 2 or 3 or a substantially identical variant thereof, for example.

In certain embodiments the protein is in a cell or in a cell-free system. The protein, the compound or the molecule in some embodiments is in association with a solid phase. In certain embodiments, the interaction between the compound and the protein is detected via a detectable label, where in some embodiments the protein comprises a detectable label and in certain embodiments the compound comprises a detectable label. The interaction between the compound and the protein sometimes is detected without a detectable label.

Also provided are methods for modulating the activity of a CK2 protein, which comprise contacting a system comprising the protein with a compound described herein in an amount effective for modulating the activity of the protein. Also provided are methods for modulating the activity of a Pim protein or a Flt protein which comprise contacting a system comprising the protein with a compound described herein in an amount effective for modulating the activity of the protein. In certain embodiments the activity of the protein is inhibited, and sometimes the protein is a CK2 protein, such as a CK2 protein comprising the amino acid sequence of SEQ ID NO: 1, 2 or 3 or a substantially identical variant thereof, for example. In certain embodiments, the system is a cell, and in other embodiments the system is a cell-free system. The protein or the compound may be in association with a solid phase in certain embodiments.

Provided also are methods for inhibiting cell proliferation, which comprise contacting cells with a compound described herein in an amount effective to inhibit proliferation of the cells. The cells sometimes are in a cell line, such as a cancer

```
SEQ ID NO: 1 (NP_001886; casein kinase II alpha 1 subunit isoform a
[Homo sapiens])
   1 msgpvpsrar vytdvnthrp reywdyeshv vewgnqddyq lvrklgrgky sevfeainit 61 nnekvvvkil kpvkkkkikr eikilenlrg gpnhitladi vkdpvsrtpa lvfehvnntd 121 fkqlyqtltd ydirfymyei lkaldychsm gimhrdvkph nvmidhehrk lrlidwglae 181 fyhpgqeynv rvasryfkgp ellvdyqmyd ysldmwslgc mlasmifrke pffhghdnyd 241 qlvriakvlg tedlydyidk ynieldprfn dilgrhsrkr werfvhsenq hlvspealdf 301 ldkllrydhq srltareame hpyfytvvkd qarmgsssmp ggstpvssan mmsgissvpt 361 psplgplags pviaaanplg mpvpaaagaq q SEQ ID NO: 2 (NP_808227; casein kinase II alpha 1 subunit isoform a
[Homo sapiens])
   1 msgpvpsrar vytdvnthrp reywdyeshv vewgnqddyq lvrklgrgky sevfeainit 61 nnekvvvkil kpvkkkkikr eikilenlrg gpniitladi vkdpvsrtpa lvfehvnntd 121 fkqlyqtltd ydirfymyei lkaldychsm gimhrdvkph nvmidhehrk lrlidwglae 181 fyhpgqeynv rvasryfkgp ellvdyqmyd ysldmwslgc mlasmifrke pffhghdnyd 241 qlvriakvlg tedlydyidk ynieldprfn dilgrhsrkr werfvhsenq hlvspealdf 301 ldkllrydhq srltareame hpyfytvvkd qarmgsssmp ggstpvssan mmsgissvpt 361 psplgplags pviaaanplg mpvpaaagaq q SEQ ID NO: 3 (NP_808228; casein kinase II alpha 1 subunit isoform b
[Homo sapiens])
   1 myeilkaldy chsmgimhrd vkphnvmidh ehrklrlidw glaefyhpgq eynvrvasry 61 fkgpellvdy qmydysldmw sigcmlasmi frkepffhgh dnydqlvria kvlgtedlyd 121 yidkynield prfndilgrh srkrwerfvh senqhlvspe aldfldkllr ydhqsrltar 181 eamehpyfyt vvkdqarmgs ssmpggstpv ssanmmsgis svptpsplgp lagspviaaa 241 nplgmpvpaa agaqq
``` cell line (e.g., breast cancer, prostate cancer, pancreatic cancer, lung cancer, hemopoietic cancer, colorectal cancer, skin cancer, ovary cancer cell line), for example. In some embodiments, the cancer cell line is a breast cancer, prostate cancer or pancreatic cancer cell line. The cells sometimes are in a tissue, can be in a subject, at times are in a tumor, and sometimes are in a tumor in a subject. In certain embodiments, the method further comprises inducing cell apoptosis. Cells sometimes are from a subject having macular degeneration.

Also provided are methods for treating a condition related to aberrant cell proliferation, which comprise administering a compound described herein to a subject in need thereof in an amount effective to treat the cell proliferative condition. In certain embodiments the cell proliferative condition is a tumor-associated cancer. The cancer sometimes is of the breast, prostate, pancreas, lung, colorectum, skin, or ovary. In some embodiments, the cell proliferative condition is a non-tumor cancer, such as a hematopoietic cancer, for example. The cell proliferative condition is macular degeneration in some embodiments.

Provided also are methods for treating cancer or an inflammatory disorder in a subject in need of such treatment, comprising: administering to the subject a therapeutically effective amount of a therapeutic agent as described herein; and administering to the subject a molecule that inhibits CK2, Pim or Flt in an amount that is effective to enhance a desired effect of the therapeutic agent. The therapeutic agent sometimes is a compound of formula TA1-1, TA2, TA3-1, TA4-1, TA5-1 or TA6-1 as described herein, or a pharmaceutically acceptable salt of one of these compounds. In certain embodiments, the molecule that inhibits CK2, Pim or Flt is a compound of Formula (I), (II), (III), (IV), (V), or (VI) as described herein, or a pharmaceutically acceptable salt thereof. In some embodiments, the molecule that inhibits CK2, Pim or Flt is a known compound, or a compound provided herein, or a pharmaceutically acceptable salt of one of these compounds. In some embodiments, the desired effect of the therapeutic agent that is enhanced by the molecule that inhibits CK2, Pim or Pt is a reduction in cell proliferation. In certain embodiments, the desired effect of the therapeutic agent that is enhanced by the molecule that inhibits CK2, Pim or Pt is an increase in apoptosis in at least one type of cell. The therapeutic agent in certain embodiments is:

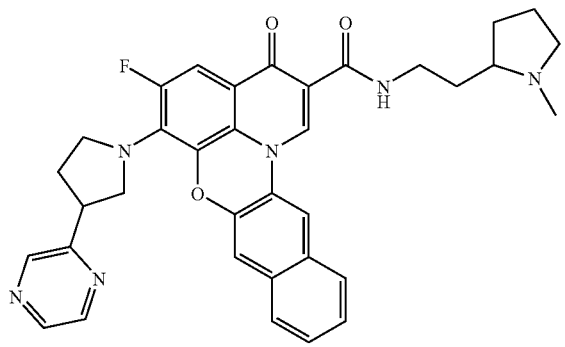

or a pharmaceutically acceptable salt thereof, or a specific isomer or mixture of isomers thereof.

In some embodiments, the therapeutic agent and the molecule that inhibits CK2, Pim or Flt are administered at substantially the same time. The therapeutic agent and molecule that inhibits CK2 sometimes are used concurrently by the subject. The therapeutic agent and the molecule that inhibits CK2, Pim or Flt are combined into one pharmaceutical composition in certain embodiments. Some embodiments are directed to a pharmaceutical composition comprising a therapeutic agent of any of formulas TA1-1, TA2, TA3-1, TA4-1, TA5-1 or TA6 admixed with a molecule that inhibits CK2, Pim or Pt, or a pharmaceutically acceptable salt thereof. In some embodiments, the molecule that inhibits CK2, Pim or Flt is a compound of Formula (I), (II), (III), (IV), (V), or (VI) as described herein, or a pharmaceutically acceptable salt thereof.

In some embodiments the therapeutic agent is a compound of formula TA2 or a pharmaceutically acceptable salt thereof. A therapeutic composition in certain embodiments comprises a therapeutically effective amount of a therapeutic agent of the formula TA2:

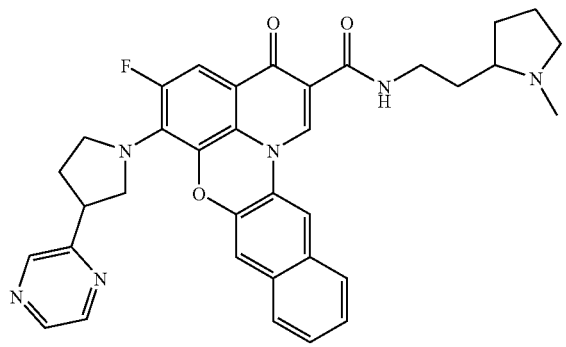

or a pharmaceutically acceptable salt thereof, or a specific isomer or mixture of isomers thereof, admixed with an amount of a CK modulator or a pharmaceutically acceptable salt of a CK modulator; and where the amount of the CK modulator or the pharmaceutically acceptable salt of a CK modulator is an amount that is effective to enhance a desired effect of the therapeutic agent.

Also provided are compositions comprising a compound described herein and an isolated protein. The protein sometimes is a CK2 protein, such as a CK2 protein comprising the amino acid sequence of SEQ ID NO: 1, 2 or 3 or a substantially identical variant thereof, for example. In some embodiments, the protein is a Pim protein. In other embodiments, the protein is a Flt protein. Certain compositions comprise a compound described herein in combination with a cell. The cell may be from a cell line, such as a cancer cell line. In the latter embodiments, the cancer cell line is sometimes a breast cancer, prostate cancer, pancreatic cancer, lung cancer, hemopoietic cancer, colorectal cancer, skin cancer, ovary cancer cell line.

These and other embodiments of the invention are described in the description that follows.

MODES OF CARRYING OUT THE INVENTION

Compounds of Formula (I), (II), (III), (IV), (V), and (VI) can exert biological activities that include, but are not limited to, inhibiting cell proliferation, modulating protein kinase activity and modulating polymerase activity. Compounds of Formula (I), (II), (III), (IV), (V), and (VI) can modulate CK2 activity, for example. Such compounds therefore can be utilized in multiple applications by a person of ordinary skill in the art. For example, compounds described herein may find uses that include, but are not limited to, (i) modulation of protein kinase activity (e.g., CK2 activity), (ii) modulation of cell proliferation, (iii) modulation of apoptosis, and (iv) treatments of cell proliferation related disorders (e.g., administration alone or co-administration with another molecule).

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

The compounds of the invention often have ionizable groups so as to be capable of preparation as salts. In that case, wherever reference is made to the compound, it is understood in the art that a pharmaceutically acceptable salt may also be used. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art. In some cases, the compounds may contain both an acidic and a basic functional group, in which case they may have two ionized groups and yet have no net charge.

In some cases, the compounds of the invention contain one or more chiral centers. The invention includes each of the isolated stereoisomeric forms as well as mixtures of stereoisomers in varying degrees of chiral purity, including racemic mixtures. It also encompasses the various diastereomers and tautomers that can be formed. The compounds of the invention may also exist in more than one tautomeric form; the depiction herein of one tautomer is for convenience only, and is also understood to encompass other tautomers of the form shown.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C or as C1-C10 or C1-10. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the backbone of the ring or chain being described.

Typically, the alkyl, alkenyl and alkynyl substituents of the invention contain 1-10C (alkyl) or 2-10C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl and alkynyl groups are often optionally substituted to the extent that such substitution makes sense chemically. Typical substituents include, but are not limited to, halo, =O, =N—CN, =N—OR, =NR, OR, $NR_2$, SR, $SO_2R$, $SO_2NR_2$, $NRSO_2R$, $NRCONR_2$, $NRCOOR$, NRCOR, CN, C≡CR, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', $NR'_2$, SR', $SO_2R'$, $SO_2NR'_2$, $NR'SO_2R$, $NR'CONR'_2$, NR'COOR', NR'COR', CN, C≡CR', COOR', $CONR'_2$, OOCR', COR', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

"Acetylene" substituents are 2-10C alkynyl groups that are optionally substituted, and are of the formula —C≡C—$R^a$, wherein $R^a$ is H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and each $R^a$ group is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O; and wherein two R' can be linked to form a 3-7 membered ring optionally containing up to three heteroatoms selected from N, O and S. In some embodiments, $R^a$ of —C≡C—$R^a$ is H or Me.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Typical heteroaromatic systems include monocyclic C5-C6 aromatic groups such as, for example, pyridine, pyridazine, pyrimidine, pyrazine, triazine, pyran, pyrrole, pyrroline, imidazole, imidazoline, pyrazole, pyrazoline, triazole, tetrazole, thiophene, thiazole, isothiazole, thiadiazole, furan, oxazole, isoxazole, oxadiazole, oxathiadiazole, and the fused bicyclic moieties formed by fusing one of these monocyclic groups with a phenyl ring or with any of the heteroaromatic monocyclic groups to form a C8-C10 bicyclic group such as indole, benzimidazole, indazole, benzotriazole, isoquinoline, quinoline, benzothiazole, benzofuran, pyrazolopyridine, quinazoline, quinoxaline, cinnoline, and the like.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, NR$_2$, SR, SO$_2$R, SO$_2$NR$_2$, NRSO$_2$R, NRCONR$_2$, NRCOOR, NRCOR, CN, C≡CR, COOR, CONR$_2$, OOCR, COR, and NO$_2$, wherein each R is independently H, C1-C8 alkyl, C2-C8 heteroalkyl, C2-C8 alkenyl, C2-C8 heteroalk-enyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —(CH$_2$)$_n$— where n is 1-8 and preferably n is 1-4, though where specified, an alkylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, $R^7$ is alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Halo", as used herein includes fluoro, chloro, bromo and iodo. Fluoro and chloro are often preferred.

"Amino" as used herein refers to NH$_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle" refers to a cyclic compound containing only carbon atoms in the ring, whereas a "heterocycle" refers to a cyclic compound comprising a heteroatom. The carbocyclic and heterocyclic structures encompass compounds having monocyclic, bicyclic or multiple ring systems, and may also comprise aryl or heteroaryl rings.

As used herein, the term "heteroatom" refers to any atom that is not carbon or hydrogen, such as nitrogen, oxygen or sulfur.

Illustrative examples of heterocycles include but are not limited to pyridine, pyridazine, pyrimidine, pyrazine, triazine, pyran, pyrrole, pyrroline, imidazole, imidazoline, pyrazole, pyrazoline, triazole, tetrazole, thiophene, thiazole, isothiazole, thiadiazole, furan, oxazole, isoxazole, oxadiazole, oxathiadiazole, benzimidazole, benzofuran, isobenzofuran, indole, benzothiazole, benzotriazole, isoquinoline, quinoline, pyrazolopyridine, quinazoline, quinoxaline, cinnoline, tetrahydrofuran, 1,3-dioxolane, 2,3-dihydrofuran, tetrahydropyran, 1,3-dihydro-isobenzofuran, 4,5-dihydroisoxazole, piperidine, pyrrolidine, pyrrolidin-2-one, octahydropyrrolo[3,4 b]pyridine, piperazine, morpholine, thiomorpholine, imidazolidine-2,4-dione, 1,3-dihydrobenzimidazol-2-one, tetrahydro-thiophene-1,1-dioxide, diazepine, diazabicyclo[2.2.1]heptane, 2,5 diazabicyclo[2.2.1] heptane, 2,3,4,4a,9,9a hexahydro-1H-β-carboline, oxirane, oxetane, dioxane, aziridine, azetidine, lactones, and lactams.

As used herein, the term "inorganic substituent" refers to substituents that do not contain carbon or contain carbon bound to elements other than hydrogen (e.g., elemental carbon, carbon monoxide, carbon dioxide, and carbonate). Examples of inorganic substituents include but are not limited to nitro, halogen, azido, cyano, sulfonyls, sulfinyls, sulfonates, phosphates, etc.

The terms "treat" and "treating" as used herein refer to ameliorating, alleviating, lessening, and removing symptoms of a disease or condition. A candidate molecule or compound described herein may be in a therapeutically effective amount in a formulation or medicament, which is an amount that can lead to a biological effect, such as apoptosis of certain cells (e.g., cancer cells), reduction of proliferation of certain cells, or lead to ameliorating, alleviating, lessening, or removing symptoms of a disease or condition, for example. The terms also can refer to reducing or stopping a cell proliferation rate (e.g., slowing or halting tumor growth) or reducing the number of proliferating cancer cells (e.g., removing part or all of a tumor). These terms also are applicable to reducing a titre of a microorganism in a system (i.e., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganism include but are not limited to virus, bacterium and fungus.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

The invention in part provides pharmaceutical compositions comprising at least one compound within the scope of the invention as described herein, and methods of using compounds described herein. For example, the invention in part provides methods for identifying a candidate molecule that interacts with a CK2 protein, which comprises contacting a composition containing a CK2 protein and a molecule described herein with a candidate molecule and determining whether the amount of the molecule described herein that interacts with the protein is modulated, whereby a candidate molecule that modulates the amount of the molecule described herein that interacts with the protein is identified as a candidate molecule that interacts with the protein. In other embodiments, the invention provides methods for identifying a candidate molecule that interacts with a Pim or Flt protein, which comprises contacting a composition containing a Pim or Flt protein and a molecule described herein with a candidate molecule and determining whether the amount of the molecule described herein that interacts with the protein is modulated, whereby a candidate molecule that modulates the amount of the molecule described herein that interacts with the protein is identified as a candidate molecule that interacts with the protein.

Also provided are methods for modulating the activity of a CK2 protein, which comprises contacting a system comprising the protein with a compound described herein in an amount effective for modulating (e.g., inhibiting) the activity of the protein. The system in such embodiments can be a cell-free system or a system comprising cells. Also provided are methods for reducing cell proliferation, and optionally inducing apoptosis, which comprises contacting cells with a compound described herein in an amount effective to reduce proliferation of the cells. The cells in such embodiments can be in a cell line, in a tissue or in a subject (e.g., a research animal or human). In related embodiments, provided are compositions comprising a compound described herein in combination with a protein or cell, such as an isolated protein (e.g., isolated CK2 or other serine-threonine protein kinase protein) or a cell in a cell line (e.g., HCT-116 cell line).

Provided also are methods for modulating a serine-threonine protein kinase activity. Serine-threonine protein kinases catalyze the transfer of a gamma phosphate from adenosine triphosphate to a serine or threonine amino acid in a peptide or protein substrate. Thus, included herein are methods which comprise contacting a system comprising a serine-threonine protein kinase protein with a compound described herein in an amount effective for modulating (e.g., inhibiting) the activity of the protein. In some embodiments, the activity of the serine-threonine protein kinase is the catalytic activity of the protein (e.g., catalyzing the transfer of a gamma phosphate from adenosine triphosphate to a peptide or protein substrate). In certain embodiments, provided are methods for identifying a candidate molecule that interacts with a serine-threonine protein kinase, which comprise: contacting a composition containing a serine-threonine protein kinase and a compound described herein with a candidate molecule under conditions in which the compound and the protein kinase interact, and determining whether the amount of the compound that interacts with the protein is modulated relative to a control interaction between the compound and the protein without the candidate molecule, whereby a candidate molecule that modulates the amount of the compound interacting with the protein relative to the control interaction is identified as a candidate molecule that interacts with the protein. Systems in such embodiments can be a cell-free system or a system comprising cells (e.g., in vitro). The protein, the compound or the molecule in some embodiments is in association with a solid phase. In certain embodiments, the interaction between the compound and the protein is detected via a detectable label, where in some embodiments the protein comprises a detectable label and in certain embodiments the compound comprises a detectable label. The interaction between the compound and the protein sometimes is detected without a detectable label.

Provided also are methods for modulating a protein kinase activity. Protein kinases catalyze the transfer of a gamma phosphate from adenosine triphosphate to a serine or threonine amino acid (serine/threonine protein kinase), tyrosine amino acid (tyrosine protein kinase), tyrosine, serine or threonine (dual specificity protein kinase) or histidine amino acid (histidine protein kinase) in a peptide or protein substrate. Thus, included herein are methods which comprise contacting a system comprising a protein kinase protein with a compound described herein in an amount effective for modulating (e.g., inhibiting) the activity of the protein kinase. In some embodiments, the activity of the protein kinase is the catalytic activity of the protein (e.g., catalyzing the transfer of a gamma phosphate from adenosine triphosphate to a peptide or protein substrate). In certain embodiments, provided are methods for identifying a candidate molecule that interacts with a protein kinase, which comprise: contacting a composition containing a protein kinase and a compound described herein with a candidate molecule under conditions in which the compound and the protein kinase interact, and determining whether the amount of the compound that interacts with the protein kinase is modulated relative to a control interaction between the compound and the protein kinase without the candidate molecule, whereby a candidate molecule that modulates the amount of the compound interacting with the protein kinase relative to the control interaction is identified as a candidate molecule that interacts with the protein kinase. Systems in such embodiments can be a cell-free system or a system comprising cells (e.g., in vitro). The protein kinase, the compound or the molecule in some embodiments is in association with a solid phase. In certain embodiments, the interaction between the compound and the protein kinase is detected via a detectable label, where in some embodiments the protein kinase comprises a detectable label and in certain embodiments the compound comprises a detectable label. The interaction between the compound and the protein kinase sometimes is detected without a detectable label.

Provided also are compositions of matter comprising a protein kinase and a compound described herein. In some embodiments, the protein kinase in the composition is a serine-threonine protein kinase or a tyrosine protein kinase. In certain embodiments, the protein kinase is a protein kinase fragment having compound-binding activity. In some embodiments, the protein kinase in the composition is, or contains a subunit (e.g., catalytic subunit, SH2 domain, SH3 domain) of, CK2, Pim subfamily protein kinase (e.g., PIM1, PIM2, PIM3) or Flt subfamily protein kinase (e.g, FLT1, FLT3, FLT4). In certain embodiments the composition is cell free and sometimes the protein kinase is a recombinant protein. The protein kinase can be from any source, such as cells from a mammal, ape or human, for example. In certain embodiments, the protein kinase is a human protein kinase.

The serine-threonine protein kinase can be from any source, such as a mammal, ape or human, for example. Examples of serine-threonine protein kinases that may be inhibited by compounds disclosed herein include without limitation human versions of CK2, CK2α2, Pim subfamily kinases (e.g., PIM1, PIM2, PIM3), CDK1/cyclinB, c-RAF, Mer, MELK, HIPK3, HIP 2, ZIPK and ZIPK. A serine-threonine protein kinase sometimes is a member of a sub-family containing one or more of the following amino acids at positions corresponding to those listed in human CK2: leucine at position 45, methionine at position 163 and isoleucine at position 174. Examples of such protein kinases include without limitation human versions of CK2, STK10, HIPK2, HIPK3, DAPK3, DYK2 and PIM-1. Examples of tyrosine protein kinases that can be inhibited, or may potentially be inhibited, by compounds disclosed herein include without limitation human versions of Flt subfamily members (e.g., FLT1, FLT2, FLT3, FLT3 (D835Y), FLT4). An example of a dual specificity protein kinase that can be inhibited, or may potentially be inhibited, by compounds disclosed herein includes without limitation DYRK2. Nucleotide and amino acid sequences for serine-threonine protein kinases and reagents are publicly available (e.g., World Wide Web URLs ncbi.nlm.nih.gov/sites/entrez/and Invitrogen.com). For example, various nucleotide sequences can be accessed using the following accession numbers: NM_002648.2 and NP_002639.1 for PIM1; NM_006875.2 and NP_006866.2 for PIM2; XM_938171.2 and XP_943264.2 for PIM3; NM_004119.2 and NP_004110.2 for FLT3; NM_002020.3 and NP_002011.2 for FLT4; and NM_002019.3 and NP_002010.2 for FLT1.

The invention also in part provides methods for treating a condition related to aberrant cell proliferation. For example, provided are methods of treating a cell proliferative condition in a subject, which comprises administering a compound described herein to a subject in need thereof in an amount effective to treat the cell proliferative condition. The subject may be a research animal (e.g., rodent, dog, cat, monkey), optionally containing a tumor such as a xenograft tumor (e.g., human tumor), for example, or may be a human. A cell proliferative condition sometimes is a tumor or non-tumor cancer, including but not limited to, cancers of the colorectum, breast, lung, liver, pancreas, lymph node, colon, prostate, brain, head and neck, skin, liver, kidney, blood and heart (e.g., leukemia, lymphoma, carcinoma).

Also provided are methods for treating a condition related to inflammation or pain. For example, provided are methods of treating pain in a subject, which comprise administering a compound described herein to a subject in need thereof in an amount effective to treat the pain. Provided also are methods of treating inflammation in a subject, which comprises administering a compound described herein to a subject in need thereof in an amount effective to treat the inflammation. The subject may be a research animal (e.g., rodent, dog, cat, monkey), for example, or may be a human. Conditions associated with inflammation and pain include without limitation acid reflux, heartburn, acne, allergies and sensitivities, Alzheimer's disease, asthma, atherosclerosis, bronchitis, carditis, celiac disease, chronic pain, Crohn's disease, cirrhosis, colitis, dementia, dermatitis, diabetes, dry eyes, edema, emphysema, eczema, fibromyalgia, gastroenteritis, gingivitis, heart disease, hepatitis, high blood pressure, insulin resistance, interstitial cystitis, joint pain/arthritis/rheumatoid arthritis, metabolic syndrome (syndrome X), myositis, nephritis, obesity, osteopenia, osteoporosis, Parkinson's disease, periodontal disease, polyarteritis, polychondritis, psoriasis, scleroderma, sinusitis, Sjögren's syndrome, spastic colon, systemic candidiasis, tendonitis, urinary track infections, vaginitis, inflammatory cancer (e.g., inflammatory breast cancer) and the like. Methods for determining effects of compounds herein on pain or inflammation are known. For example, formalin-stimulated pain behaviors in research animals can be monitored after administration of a compound described herein to assess treatment of pain (e.g., Li et al., *Pain* 115(1-2): 182-90 (2005)). Also, modulation of pro-inflammatory molecules (e.g., IL-8, GRO-alpha, MCP-1, TNFalpha and iNOS) can be monitored after administration of a compound described herein to assess treatment of inflammation (e.g., Parhar et al., *Int J Colorectal Dis.* 22(6): 601-9 (2006)), for example. Thus, also provided are methods for determining whether a compound herein reduces inflammation or pain, which comprise contacting a system with a compound described herein in an amount effective for modulating (e.g., inhibiting) the activity of a pain signal or inflammation signal. Provided also are methods for identifying a compound that reduces inflammation or pain, which comprise: contacting a system with a compound of Formula (I), (II), (III), (IV), (V) or (VI); and detecting a pain signal or inflammation signal, whereby a compound that modulates the pain signal relative to a control molecule is identified as a compound that reduces inflammation of pain. Non-limiting examples of pain signals are formalin-stimulated pain behaviors and examples of inflammation signals include without limitation a level of a pro-inflammatory molecule.

The invention also in part pertains to methods for modulating angiogenesis in a subject, and methods for treating a condition associated with aberrant angiogenesis in a subject. Thus, provided are methods for determining whether a compound herein modulates angiogenesis, which comprise contacting a system with a compound described herein in an amount effective for modulating (e.g., inhibiting) angiogenesis or a signal associated with angiogenesis. Signals associated with angiogenesis are levels of a pro-angiogenesis growth factor such as VEGF. Methods for assessing modulation of angiogenesis also are known, such as analyzing human endothelial tube formation (BD BioCoat™ Angiogenesis System from BD Biosciences). Provided also are methods for identifying a compound that modulates angiogenesis, which comprise contacting a system with a compound of Formula (I), (II), (III), (IV), (V) or (VI) or a pharmaceutically acceptable salt thereof; and detecting angiogenesis in the system or an angiogenesis signal, whereby a compound that modulates the angiogenesis or angiogenesis signal relative to a control molecule is identified as a compound that modulates angiogenesis. Also provided are methods for treating an angiogenesis condition, which comprise administering a compound described herein to a subject in need thereof in an amount effective to treat the angiogenesis condition. Angiogenesis conditions include without limitation solid tumor cancers, varicose disease and the like.

The invention also in part pertains to methods for modulating an immune response in a subject, and methods for treating a condition associated with an aberrant immune response in a subject. Thus, provided are methods for determining whether a compound herein modulates an immune response, which comprise contacting a system with a compound described herein in an amount effective for modulating (e.g., inhibiting) an immune response or a signal associated with an immune response. Signals associated with immunomodulatory activity include, e.g., stimulation of T-cell proliferation, suppression or induction of cytokines, including, e.g., interleukins, interferon-γ and TNF. Methods of assessing immunomodulatory activity are known in the art. Provided also are methods for identifying a compound that modulates an immune response, which comprise contacting a system with a compound of Formula (I), (II), (III), (IV), (V) or (VI) or a pharmaceutically acceptable salt thereof; and detecting immunomodulatory activity in a system, or a signal associated with immunomodulatory activity, whereby a compound that modulates the immune response relative to a control molecule is identified as an immune response modulatory compound. Also provided are methods for treating a condition associated with an aberrant immune response in a subject, which comprise administering a compound described herein to a subject in need thereof in an amount effective to treat the condition. Conditions characterized by an aberrant immune response include without limitation, organ transplant rejection, asthma, autoimmune disorders, including rheumatoid arthritis, multiple sclerosis, myasthenia gravis, systemic lupus erythematosus, Crohn's disease, and ulcerative colitis. In certain embodiments, an immune response may be modulated by administering a compound herein in combination with a molecule that modulates (e.g., inhibits) the biological activity of an mTOR pathway member or member of a related pathway (e.g., mTOR, PI3 kinase, AKT). In certain embodiments the molecule that modulates the biological activity of an mTOR pathway member or member of a related pathway is rapamycin. In certain embodiments, provided herein is a composition comprising a compound described herein in combination with a molecule that modulates the biological activity of an mTOR pathway member or member of a related pathway, such as rapamycin, for example.

In preferred embodiments of the present invention, the compound is a compound of Formula (I), (II), (III), (IV), (V) or (VI) in one of the Tables provided herein, or a pharmaceutically acceptable salt of one of these compounds.

Any suitable formulation of a compound described above can be prepared for administration. Any suitable route of administration may be used, including, but not limited to, oral, parenteral, intravenous, intramuscular, transdermal, topical and subcutaneous routes. Depending on the subject to be treated, the mode of administration, and the type of treatment desired—e.g., prevention, prophylaxis, therapy; the compounds are formulated in ways consonant with these parameters. Preparation of suitable formulations for each route of administration are known in the art. A summary of such formulation methods and techniques is found in *Remington's Pharmaceutical Sciences*, latest edition, Mack Publishing Co., Easton, Pa., which is incorporated herein by reference. The formulation of each substance or of the combination of two substances will generally include a diluent as well as, in some cases, adjuvants, buffers, preservatives and the like. The substances to be administered can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised, and can be applied to compounds of the invention. See, for example, U.S. Pat. No. 5,624,677, the methods of which are incorporated herein by reference.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as is understood in the art.

For administration to animal or human subjects, the appropriate dosage of a compound described above often is 0.01-150 mg/kg, and sometimes 0.1-100 mg/kg. Dosage levels are dependent on the nature of the condition, drug efficacy, the condition of the patient, the judgment of the practitioner, and the frequency and mode of administration; however, optimization of such parameters is within the ordinary level of skill in the art.

Therapeutic Combinations

Compounds of the invention may be used alone or in combination with another therapeutic agent. The invention provides methods to treat conditions such as cancer and inflammation by administering to a subject in need of such treatment a therapeutically effective amount of a therapeutic agent that binds to certain DNA segments and administering to the same subject a CK2 modulator in an amount that is effective to enhance the activity of the therapeutic agent. A CK2 modulator is an agent that inhibits or enhances a biological activity of a C protein, and is generically referred to hereafter as a "modulator." A Pim or Flt modulator is an agent that inhibits or enhances a biological activity of a Pim protein or a Flt protein. The therapeutic agent and the modulator may be administered together, either as separate pharmaceutical compositions or admixed in a single pharmaceutical composition. The therapeutic agent and the modulator may also be administered separately, including at different times and with different frequencies, as long as the modulator is administered at a time that increases the potency of the therapeutic agent. The modulator may be administered by any known route, such as orally, intravenously, intramuscularly, nasally, and the like; and the therapeutic agent may also be administered by any conventional route. In many embodiments, at least one and optionally both of the modulator and the therapeutic agent may be administered orally.

In some embodiments, the modulator and the therapeutic agent are administered at the same time, whether in separate dosages or admixed in a single dosage. Where the frequency of administration of the two materials can be adjusted to match, the modulator and therapeutic agent are preferably combined into a single pharmaceutical composition, so the treated patient may receive a single oral dosage or a single injection, for example.

The amount of each of these materials to be administered will vary with the route of administration, the condition of the subject, other treatments being administered to the subject, and other parameters. The therapeutic agents of the invention may, of course, cause multiple desired effects; and the amount of modulator to be used in combination with the therapeutic agent should be an amount that increases one or more of these desired effects. The modulator is to be administered in an amount that is effective to enhance a desired effect of the therapeutic agent. An amount is "effective to enhance a desired effect of the therapeutic agent", as used herein, if it increases by at least about 25% at least one of the desired effects of the therapeutic agent alone. Preferably, it is an amount that increases a desired effect of the therapeutic agent by at least 50% or by at least 100% (i.e., it doubles the effective activity of the therapeutic agent.) In some embodiments, it is an amount that increases a desired effect of the therapeutic agent by at least 200%.

The amount of a modulator that increases a desired effect of a therapeutic agent may be determined using in vitro methods, such as cell proliferation assays. The therapeutic agents of the invention are useful to counter hyperproliferative disorders such as cancer, thus they reduce cell proliferation. Thus, for example, a suitable amount of a modulator could be the amount needed to enhance an antiproliferative effect of a therapeutic agent by at least 25% as determined in a cell proliferation assay.

The modulator used in the present invention enhances at least one desired effect produced by the therapeutic agent it is used with, thus the combinations of the invention provide a synergistic effect, not merely an additive effect. The modulators themselves are at times useful for treating the same types of conditions, and thus may also have some direct effect in such assays. In that event, the "amount effective to increase a desired effect" must be a synergistic enhancement of the activity of the therapeutic agent that is attributable to enhancement by the modulator of an effect of the therapeutic agent, rather than a simple additive effect that would be expected with separate administration of the two materials. In many cases, the modulator can be used in an amount (concentration) that would not be expected to have any apparent effect on the treated subject or the in vitro assay, so the increased effect achieved with the combination is directly attributable to a synergistic effect.

The present invention includes methods and compositions for treating a patient having a cell proliferation disorder or an inflammatory disorder with a therapeutic agent as described herein, and a "modulator" described above, where the timing of administration of the modulator permits it to enhance a desired effect of the therapeutic agent.

In certain embodiments, a "modulator" as described above may be used in combination with a therapeutic agent that can act by binding to regions of DNA that can form certain quadruplex structures. In such embodiments, the therapeutic agents have anticancer activity on their own, but their activity is enhanced when they are used in combination with a modulator. This synergistic effect allows the therapeutic agent to be administered in a lower dosage while achieving equivalent or higher levels of at least one desired effect.

For administration to animal or human subjects, the appropriate dosage of a modulator, such as a compound of Formula (I), (II), (III), (IV), (V), or (VI) as described herein, is typically between about 0.01-15 mg/kg, and about 0.1-10 mg/kg. Dosage levels are dependent on the nature of the condition, drug efficacy, the condition of the patient, the judgment of the practitioner, and the frequency and mode of administration; however, optimization of such parameters is within the ordinary level of skill in the art.

A modulator may be separately active for treating a cancer. For combination therapies described above, when used in combination with a therapeutic agent, the dosage of a modulator will frequently be two-fold to ten-fold lower than the dosage required when the modulator is used alone to treat the same condition or subject. Determination of a suitable amount of the modulator for use in combination with a therapeutic agent is readily determined by methods known in the art.

The therapeutic agents of the invention are compounds that bind to certain motifs in nucleic acids. The therapeutic agent to be used can be selected from several different classes of compounds, such as those that bind to quadruplex-forming regions of DNA. The therapeutic agents are useful for the treatment of cancer and other indications such as inflammatory disorders, and methods for making and using them are known in the art. Several preferred classes of these therapeutic agents are described below. Each class of therapeutic agents can be used in combination with any active CK modulator, including but not limited to those disclosed herein.

In one aspect, the therapeutic agent can be a compound of formula (TA1-1):

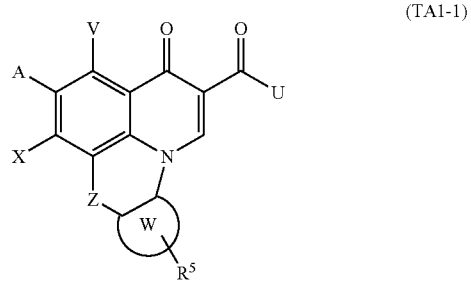

(TA1-1)

and pharmaceutically acceptable salts, esters and prodrugs thereof;
wherein V is H, halo, or $NR^1R^2$;
A is H, fluoro, or $NR^1{}_2$;
Z is O, S, $NR^1$ or $CH_2$;
U is $OR^2$ or $NR^1R^2$;
X is $OR^2$, $NR^1R^2$, halo, azido, or $SR^2$;
n is 1-3;
wherein in $NR^1R^2$, $R^1$ and $R^2$ may form a double bond or a ring, each of which is optionally substituted;
$R^1$ is H or a $C_{1-6}$ alkyl;
$R^2$ is H or a $C_{1-10}$ alkyl or $C_{2-10}$ alkenyl optionally containing one or more non-adjacent heteroatoms selected from N, O, and S, and optionally substituted with a carbocyclic or heterocyclic ring; or $R^2$ is an optionally substituted heterocyclic ring, aryl or heteroaryl;
$R^5$ is a substituent at any position on W; and is H, $OR^2$, $C_{1-6}$ alkyl, $C_{2-6}$ alkenyl, each optionally substituted by halo, =O or one or more heteroatoms; or $R^5$ is an inorganic substituent; and
W is an optionally substituted aryl or heteroaryl, which may be monocyclic or fused with a single or multiple ring and optionally containing a heteroatom;
or a compound having formula (TA1-2):

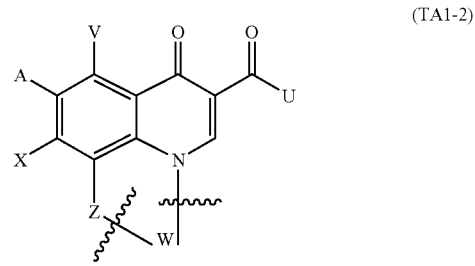

(TA1-2)

wherein V, A, X, Z and U are as defined in formula TA1-1, and W is selected from the group consisting of

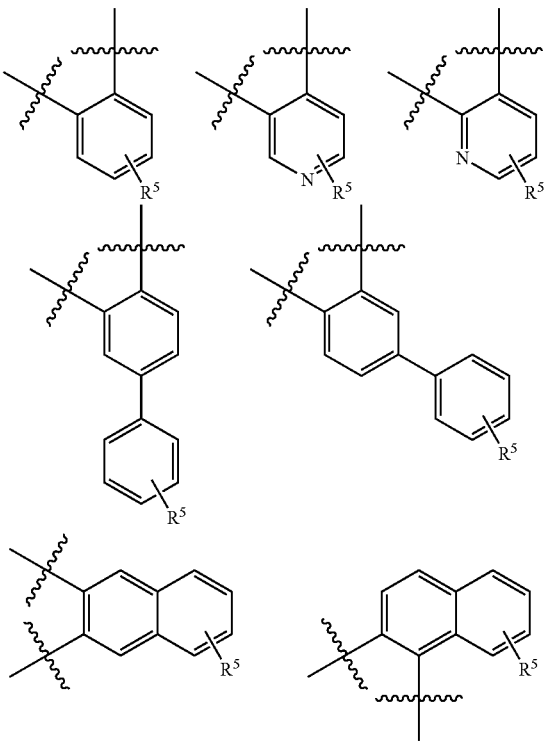

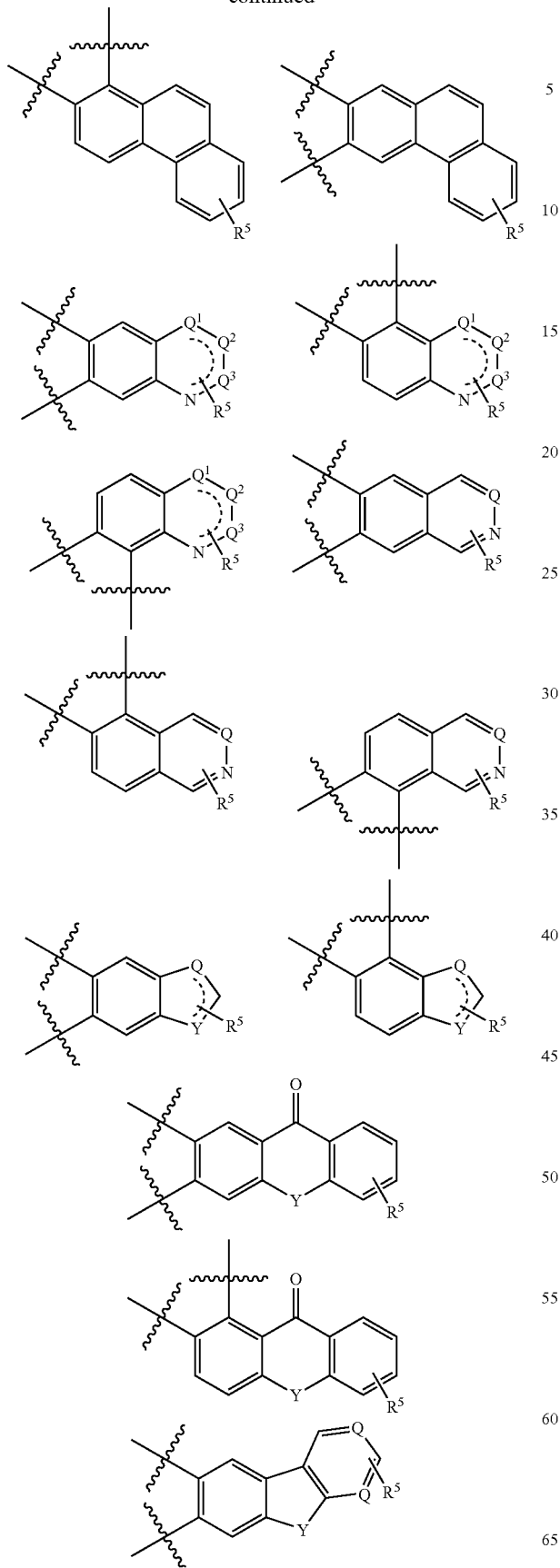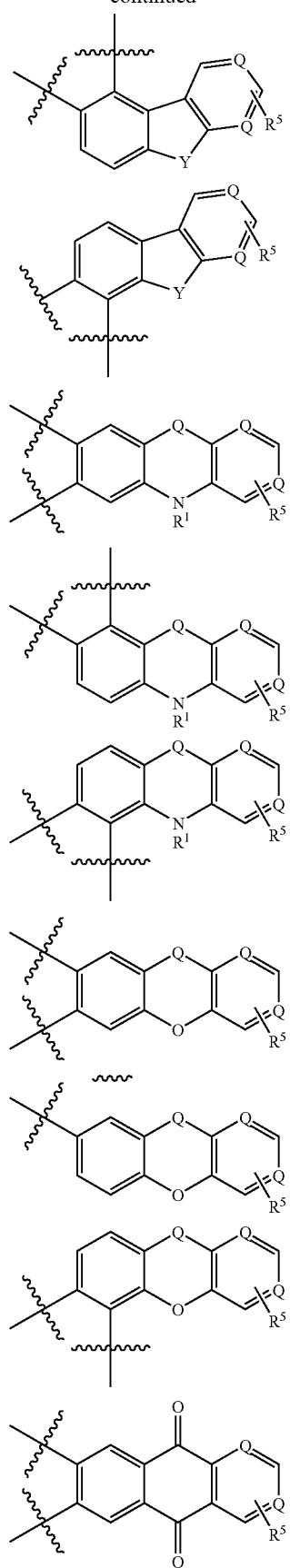

-continued

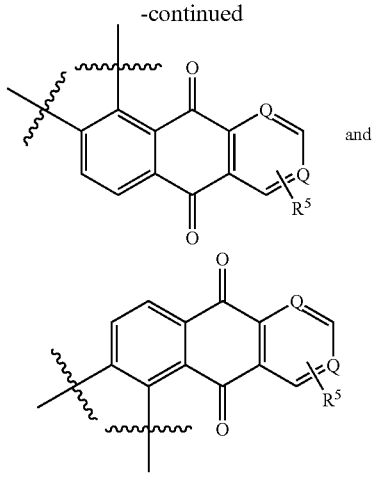
and wherein Q, $Q^1$, $Q^2$, and $Q^3$ are independently CH or N;
Y is independently O, CH, =O or $NR^1$; and
$R^5$ is as defined in formula 1.

Compounds of this structure, and methods for making and using them, are described in U.S. patent application Ser. No. 11/106,909, to Whitten, et al., which is entitled SUBSTITUTED QUINOBENZOXAZINE ANALOGS AND METHODS OF USING THEREOF, and was filed on Apr. 15, 2005.

In a specific embodiment of the therapeutic agents of formula (TA1-1), the therapeutic agent is a compound having formula (TA1-1A):

(TA2)

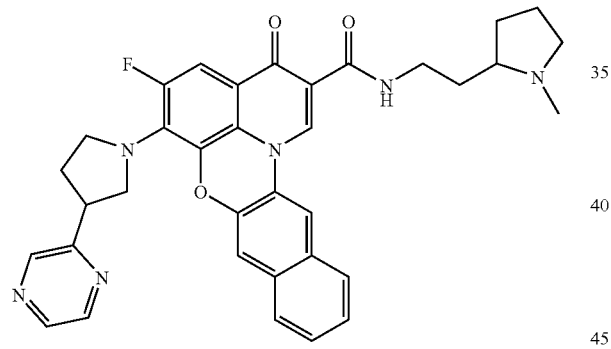

or a pharmaceutically acceptable salt, esters or prodrug thereof, or a specific isomer or mixture of isomers thereof.

In another aspect, the therapeutic agent of the combinations of the invention is a compound of this formula:

(TA3-1)

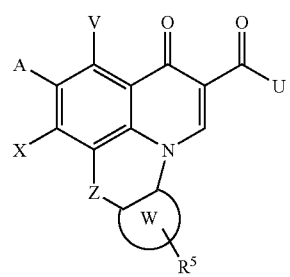

and pharmaceutically acceptable salts, esters and prodrugs thereof;
wherein V is H, halo, or $NR^1R^2$;
A is H, fluoro, or $NR^1_2$;
Z is O, S, $NR^1$ or $CH_2$;
U is $OR^2$ or $NR^1R^2$;
X is $OR^2$, $NR^1R^2$, halo, azido, or $SR^2$;
n is 1-3;
wherein in $NR^1R^2$, $R^1$ and $R^2$ may form a double bond or a ring, each of which is optionally substituted;
$R^1$ is H or a $C_{1-6}$ alkyl;
$R^2$ is H or a $C_{1-10}$ alkyl or $C_{2-10}$ alkenyl optionally containing one or more non-adjacent heteroatoms selected from N, O, and S, and optionally substituted with a carbocyclic or heterocyclic ring; or $R^2$ is an optionally substituted heterocyclic ring, aryl or heteroaryl;
$R^5$ is a substituent at any position on W; and is H, $OR^2$, $C_{1-6}$ alkyl, $C_{2-6}$ alkenyl, each optionally substituted by halo, =O or one or more heteroatoms; or $R^5$ is an inorganic substituent; and
W is an optionally substituted aryl or heteroaryl, which may be monocyclic or fused with a single or multiple ring and optionally containing a heteroatom;
or a compound having formula (TA3-2)

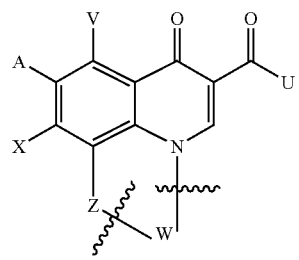

wherein V, A, X, Z and U are as defined in formula I, and W is selected from the group consisting of

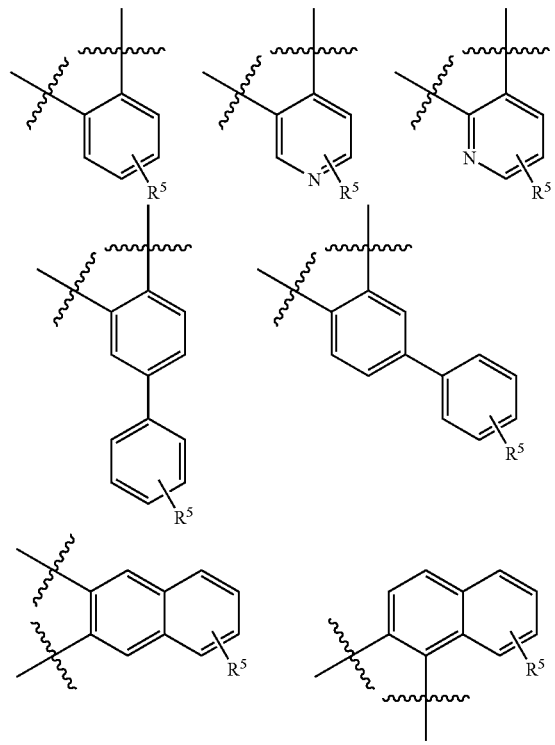

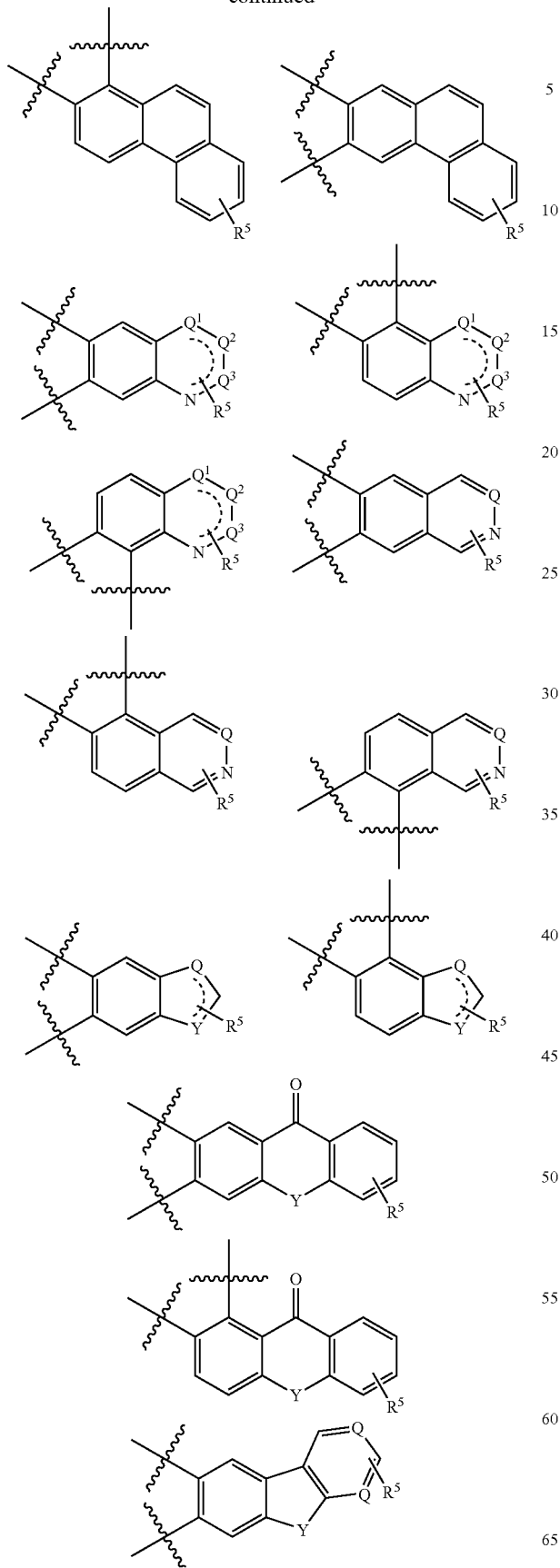
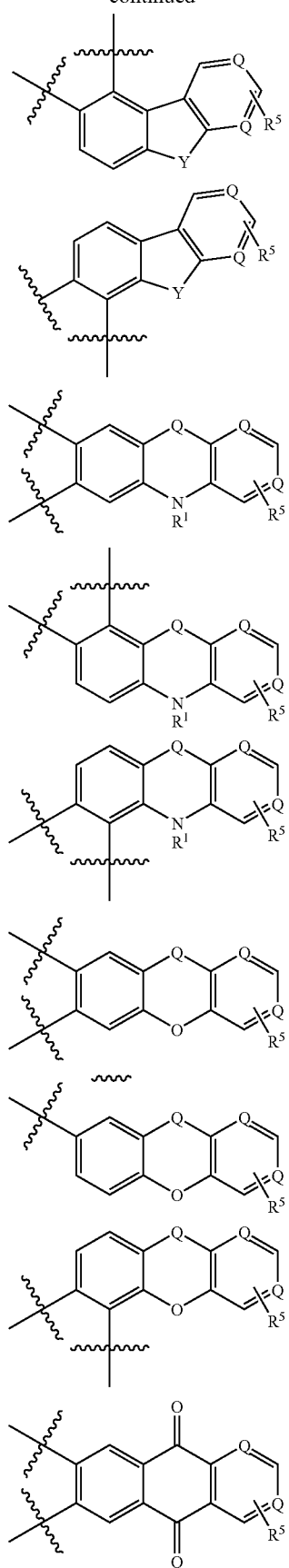

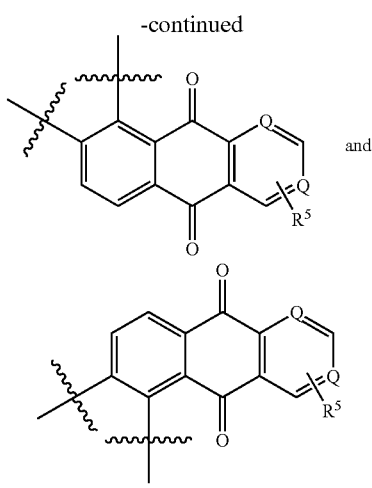

and wherein Q, $Q^1$, $Q^2$, and $Q^3$ are independently CH or N;
Y is independently O, CH, =O or $NR^1$; and
$R^5$ is as defined in formula 1.

The preparation and activity of these compounds of formula (TA3-1) are described in U.S. Patent Application Ser. No. 60/811,992, filed Jun. 8, 2006, to Nagasawa, et al., entitled QUINOLONE ANALOGS DERIVATIZED WITH SULFONIC ACID, SULFONATE OR SULFONAMIDE.

In another aspect, the therapeutic agent of the combinations of the invention is a compound of this formula:

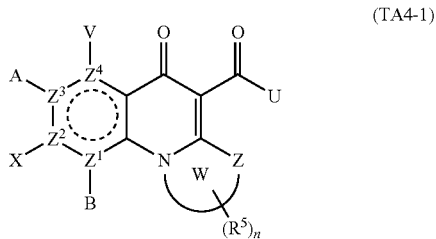

(TA4-1)

and pharmaceutically acceptable salts, esters and prodrugs thereof;
wherein B, X, A, or V is absent if $Z^2$, $Z^3$, or $Z^4$, respectively, is N, and independently H, halo, azido, $R^2$, $CH_2R^2$, $SR^2$, $OR^2$ or $NR^1R^2$ if $Z^2$, $Z^3$, or $Z^4$, respectively, is C; or
A and V, A and X, or X and B may form a carbocyclic ring, heterocyclic ring, aryl or heteroaryl, each of which may be optionally substituted and/or fused with a cyclic ring;
Z is O, S, $NR^1$, $CH_2$, or C=O;
$Z^1$, $Z^2$, $Z^3$ and $Z^4$ are C or N, provided any two N are non-adjacent;
W together with N and Z forms an optionally substituted 5- or 6-membered ring that is fused to an optionally substituted saturated or unsaturated ring; said saturated or unsaturated ring may contain a heteroatom and is monocyclic or fused with a single or multiple carbocyclic or heterocyclic rings;
U is $R^2$, $OR^2$, $NR^1R^2$, $NR^1$—$(CR^1{}_2)_n$—$NR^3R^4$, or N=$CR^1R^2$, wherein in N=$CR^1R^2R^1$ and $R^2$ together with C may form a ring,
provided U is not H, and when U is OH, $OR^2$ or $NH_2$, then at least one of $Z^1$-$Z^4$ is N;
in each $NR^1R^2$, $R^1$ and $R^2$ together with N may form an optionally substituted ring;
in $NR^3R^4$, $R^3$ and $R^4$ together with N may form an optionally substituted ring;
$R^1$ and $R^3$ are independently H or $C_{1-6}$ alkyl;
each $R^2$ is H, or a $C_{1-10}$ alkyl or $C_{2-10}$ alkenyl each optionally substituted with a halogen, one or more non-adjacent heteroatoms, a carbocyclic ring, a heterocyclic ring, an aryl or heteroaryl, wherein each ring is optionally substituted; or $R^2$ is an optionally substituted carbocyclic ring, heterocyclic ring, aryl or heteroaryl;
$R^4$ is H, a $C_{1-10}$ alkyl or $C_{2-10}$ alkenyl optionally containing one or more non-adjacent heteroatoms selected from N, O and S, and optionally substituted with a carbocyclic or heterocyclic ring; or $R^3$ and $R^4$ together with N may form an optionally substituted ring;
each $R^5$ is a substituent at any position on ring W; and is H, $OR^2$, amino, alkoxy, amido, halogen, cyano or an inorganic substituent; or $R^5$ is $C_{1-6}$ alkyl, $C_{2-6}$ alkenyl, $C_{2-6}$ alkynyl, —$CONHR^1$, each optionally substituted by halo, carbonyl or one or more non-adjacent heteroatoms; or two adjacent $R^5$ are linked to obtain a 5-6 membered optionally substituted carbocyclic or heterocyclic ring that may be fused to an additional optionally substituted carbocyclic or heterocyclic ring; and
n is 1-6.

In the above formula (TA4-1), B may be absent when $Z^1$ is N, or is H or a halogen when $Z^1$ is C.

In the above formula (TA4-1), W together with N and Z forms an optionally substituted 5- or 6-membered ring that is fused to an optionally substituted aryl or heteroaryl selected from the group consisting of:

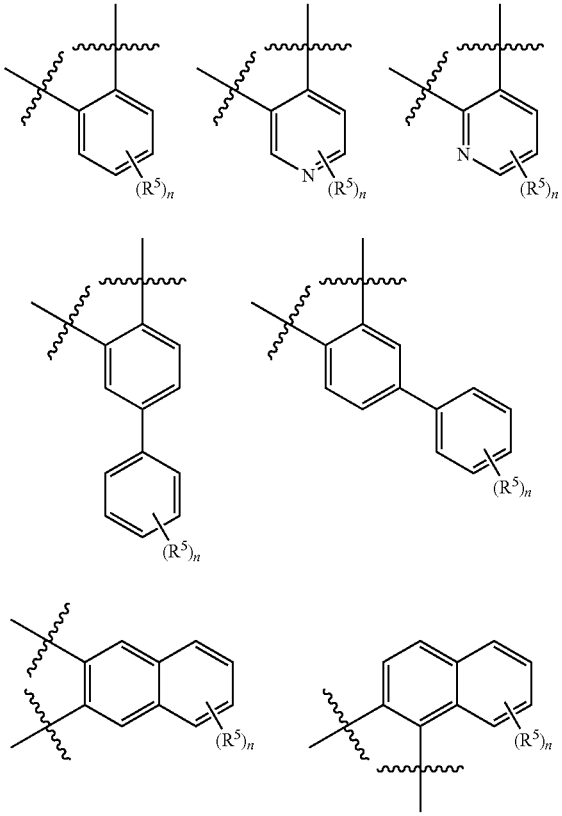

-continued
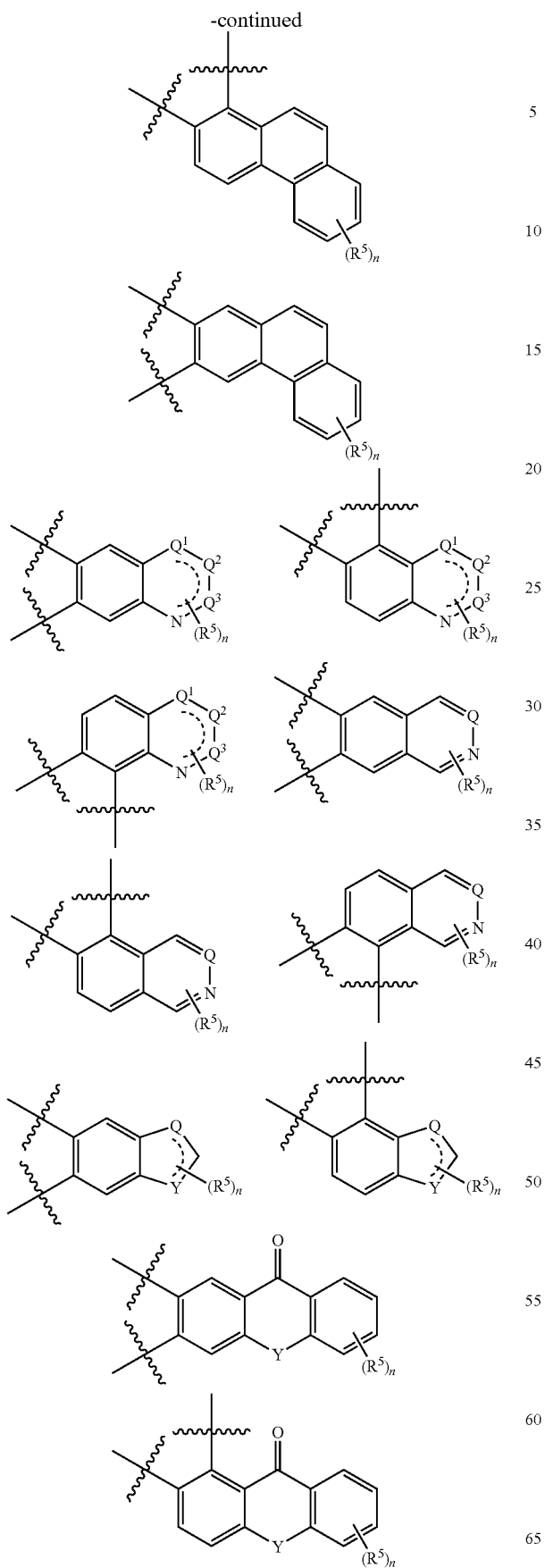
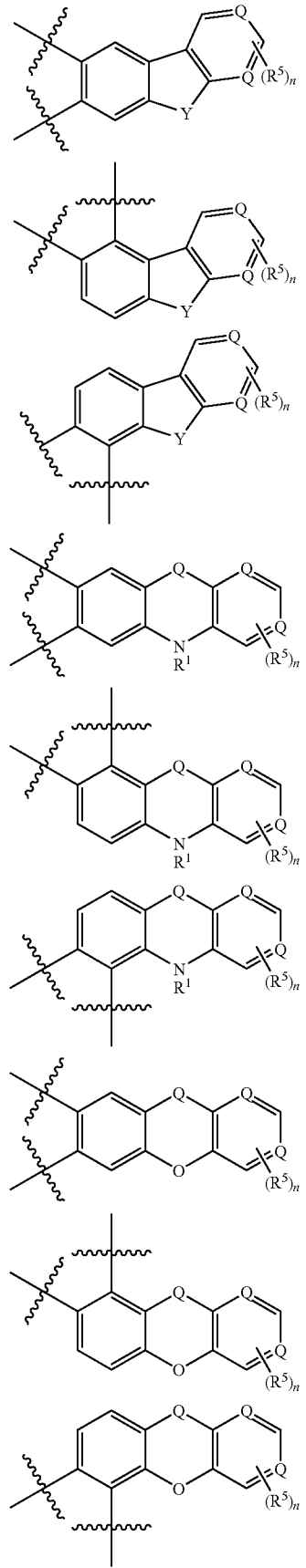

-continued

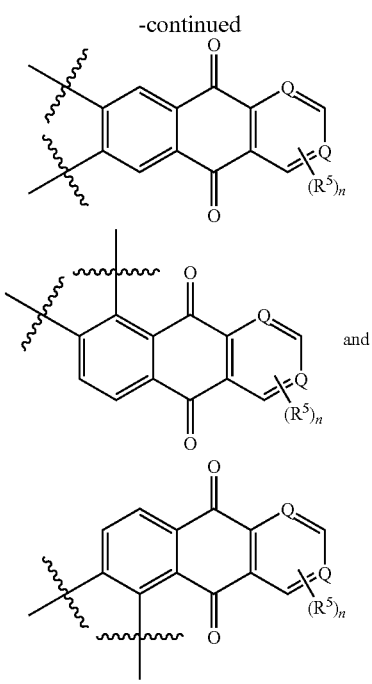

wherein each Q, $Q^1$, $Q^2$, and $Q^3$ is independently CH or N;
Y is independently O, CH, C=O or $NR^1$;
n and $R^5$ is as defined above.

In other embodiments, W together with N and Z form a group having the formula selected from the group consisting of

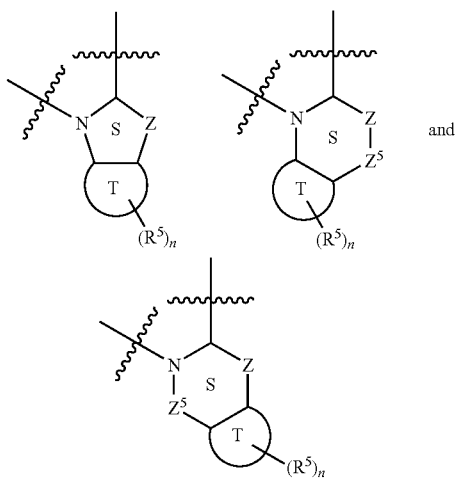

wherein Z is O, S, $CR^1$, $NR^1$, or C=O;
each $Z^5$ is $CR^6$, $NR^1$, or C=O, provided Z and $Z^5$ if adjacent are not both $NR^1$;
each $R^1$ is H, $C_{1-6}$ alkyl, $COR^2$ or $S(O)_p R^2$ wherein p is 1-2;
$R^6$ is H, or a substituent known in the art, including but not limited to hydroxyl, alkyl, alkoxy, halo, amino, or amido; and
ring S and ring T may be saturated or unsaturated.

In some embodiments, W together with N and Z forms a 5- or 6-membered ring that is fused to a phenyl. In other embodiments, W together with N and Z forms a 5- or 6-membered ring that is optionally fused to another ring, when U is $NR^1R^2$, provided U is not $NH_2$. In certain embodiments, W together with N and Z forms a 5- or 6-membered ring that is not fused to another ring, when U is $NR^1R^2$ (e.g., $NH_2$).

In yet another embodiment, the compounds of the present invention have the general formula (TA4-2A) or (TA4-2B):

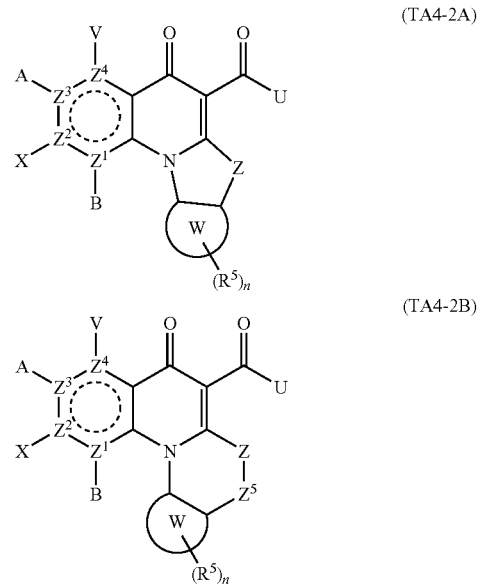

wherein A, B, V, X, U, Z, $Z^1$, $Z^2$, $Z^3$, $Z^4$ and n are as described for TA4-1;
$Z^5$ is O, $NR^1$, $CR^6$, or C=O;
$R^6$ is H, $C_{1-6}$ alkyl, hydroxyl, alkoxy, halo, amino or amido; and
Z and $Z^5$ may optionally form a double bond.

In the above formula (TA4-1), (TA4-2A) and (TA4-2B), U may be $NR^1R^2$, wherein $R^1$ is H, and $R^2$ is a $C_{1-10}$ alkyl optionally substituted with a heteroatom, a $C_{3-6}$ cycloalkyl, aryl or a 5-14 membered heterocyclic ring containing one or more N, O or S. For example, $R^2$ may be a $C_{1-10}$ alkyl substituted with an optionally substituted morpholine, thiomorpholine, imidazole, aminodithiadazole, pyrrolidine, piperazine, pyridine or piperidine. In other examples, $R^1$ and $R^2$ together with N form an optionally substituted piperidine, pyrrolidine, piperazine, morpholine, thiomorpholine, imidazole, or aminodithiazole.

The compounds of formula (TA4-1), and methods of making and using them, are described in U.S. patent application Ser. No. 11/228,636, to Whitten, et al., entitled QUINOLONE ANALOGS, and filed on Sep. 16, 2005.

In yet another aspect, the therapeutic agent to be combined with a CK modulator can be selected from compounds having this formula:

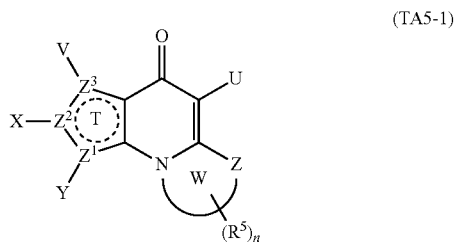

and pharmaceutically acceptable salts, esters and prodrugs thereof;

wherein V, X, and Y are absent if attached to a heteroatom other than Nitrogen, and independently H, halo, azido, $R^2$, $CH_2R^2$, $SR^2$, $OR^2$ or $NR^1R^2$ when attached to C or N; or wherein V and X, or X and Y may form a carbocyclic ring, heterocyclic ring, aryl or heteroaryl, each of which may be optionally substituted and/or fused with a cyclic ring;

$Z^1$, $Z^2$ and $Z^3$ are C, N, O or S;

Z is O, S, $NR^2$, $CH_2$ or C=O;

W together with N and Z forms an optionally substituted 5- or 6-membered ring that is fused to an optionally substituted aryl or heteroaryl, wherein said aryl or heteroaryl may be monocyclic or fused with a single or multiple ring, and wherein said ring optionally contains a heteroatom;

U is —C(=O)$R^2$, —COO$R^2$, —CON$R^1R^2$, —CON$R^1$—(C$R^1_2$)$_n$—N$R^3R^4$, SO$_3R^2$, SO$_2$N$R^1R^2$, SO$_2$N$R^1$N$R^1R^2$, SO$_2$N$R^1$O$R^2$, SO$_2$N$R^1$—(C$R^1_2$)$_n$—N$R^3R^4$ or SO$_2$N$R^1$N$R^1$—(C$R^1_2$)$_n$—N$R^3R^4$ or SO$_2$N$R^1$—O—(C$R^1_2$)$_n$—N$R^3$R;

wherein in each N$R^1R^2$, $R^1$ and $R^2$ together with N may form an optionally substituted ring;

in N$R^3R^4$, $R^3$ and $R^4$ together with N may form an optionally substituted ring;

$R^1$ and $R^3$ are independently H or $C_{1-6}$ alkyl;

each $R^2$ is H, or a $C_{1-10}$ alkyl or $C_{2-10}$ alkenyl each optionally substituted with a halogen, one or more non-adjacent heteroatoms selected from N, O and S, a carbocyclic ring, a heterocyclic ring, an aryl or heteroaryl, wherein each ring is optionally substituted; or $R^2$ is an optionally substituted carbocyclic ring, heterocyclic ring, aryl or heteroaryl; or $R^1$ is CO$R^1$ or S(O)$_xR^1$ wherein x is 1-2;

$R^4$ is H, a $C_{1-10}$ alkyl or $C_{2-10}$ alkenyl optionally containing one or more non-adjacent heteroatoms selected from N, O and S, and optionally substituted with a carbocyclic or heterocyclic ring; or $R^3$ and $R^4$ together with N may form an optionally substituted ring;

each $R^5$ is a substituent at any position on W; and is H, O$R^2$, amino, alkoxy, amido, halogen, cyano or an inorganic substituent; or $R^5$ is $C_{1-6}$ alkyl, $C_{2-6}$ alkenyl, —CONH$R^1$, each optionally substituted by halo, carbonyl or one or more non-adjacent heteroatoms; or two adjacent $R^5$ are linked to obtain a 5-6 membered optionally substituted carbocyclic or heterocyclic ring, optionally fused to an additional optionally substituted carbocyclic or heterocyclic ring; and n is 1-6.

In the above formula (TA5-1), ring T may form an optionally substituted 5-membered ring selected from the group consisting of:

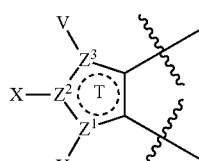

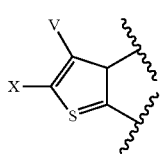 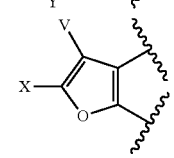 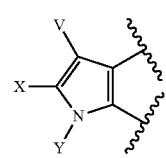

-continued

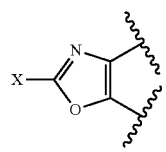 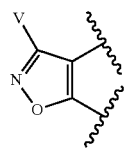 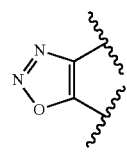

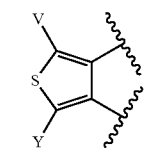 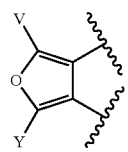 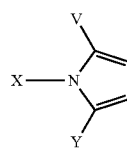

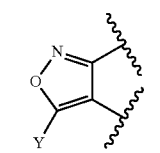 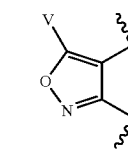 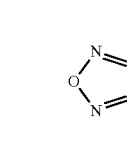

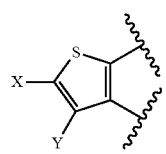 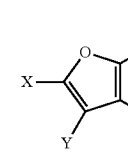 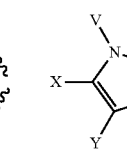

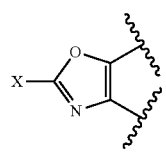 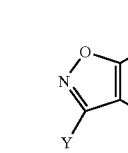 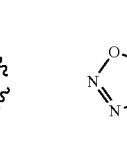

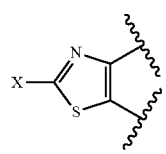 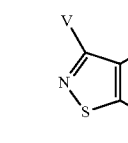 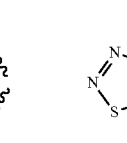

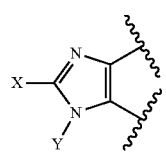 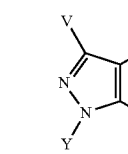 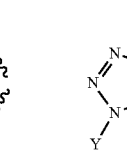

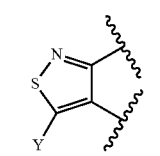 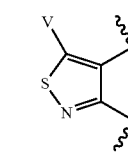 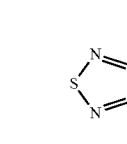

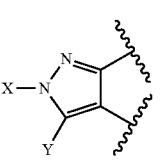 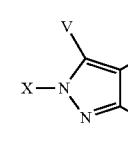 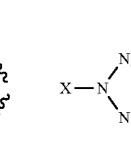

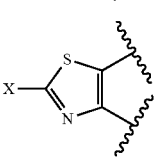 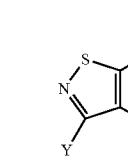 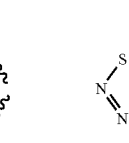

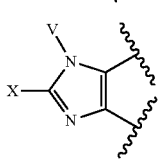 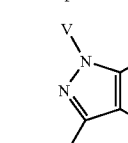 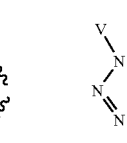

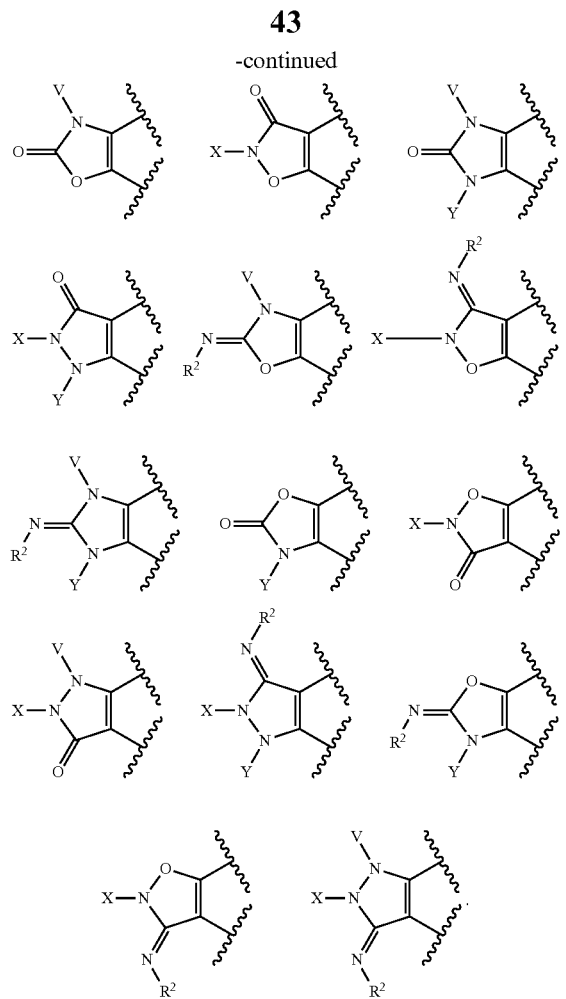
In the above formula (TA5-1), W together with N and Z may form an optionally substituted 5- or 6-membered aryl or heteroaryl ring that is fused to an optionally substituted aryl or heteroaryl selected from the group consisting of:
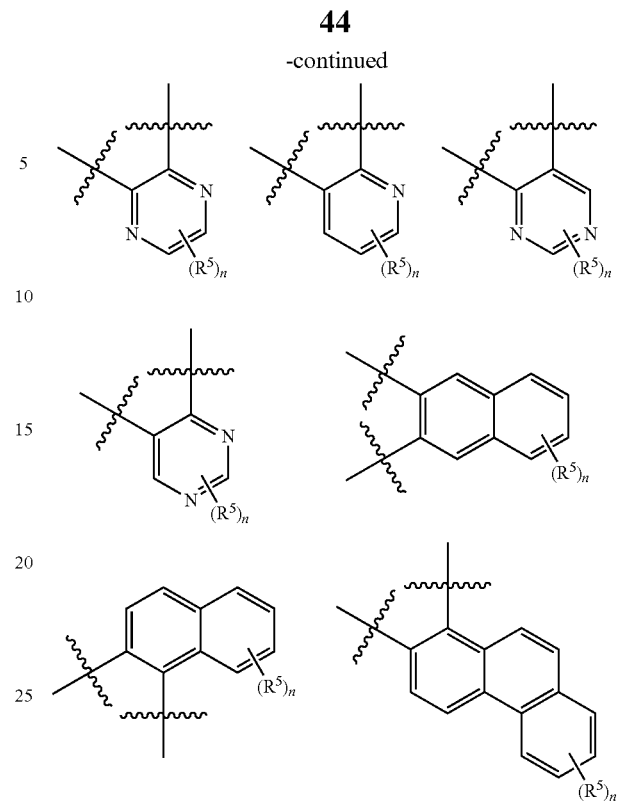
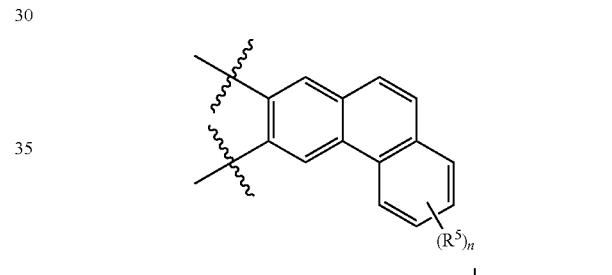
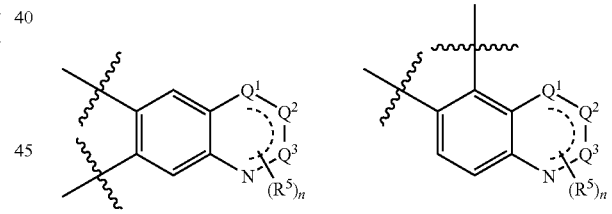
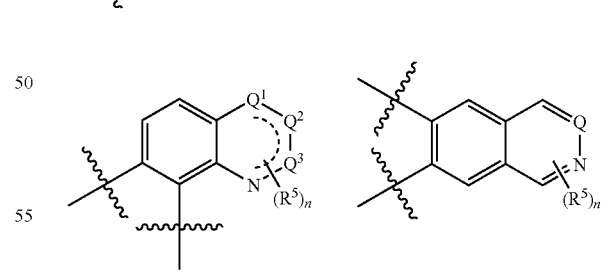
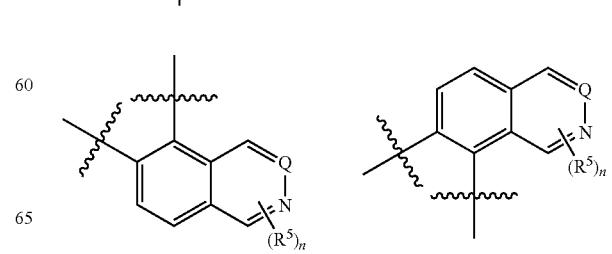

-continued
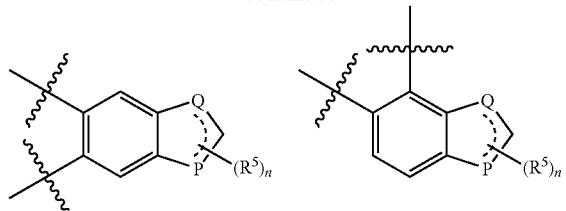
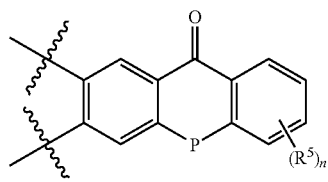
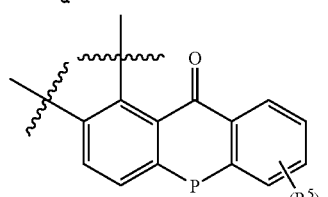
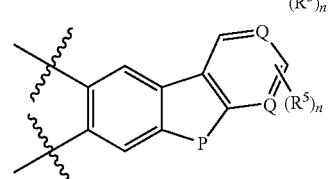
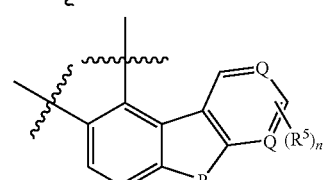
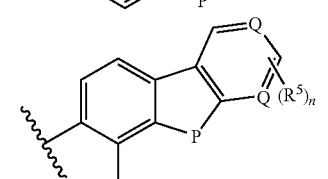
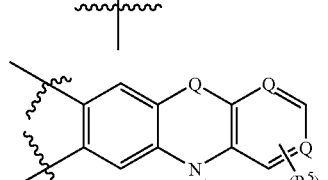
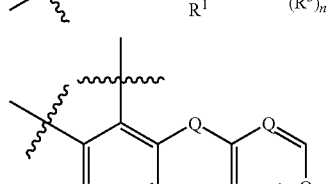
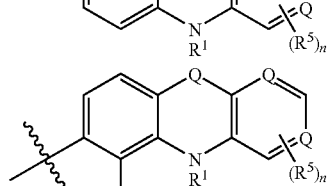
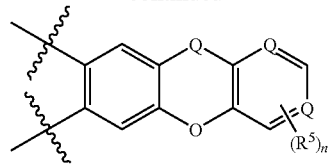
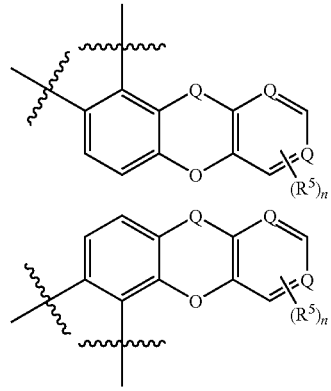
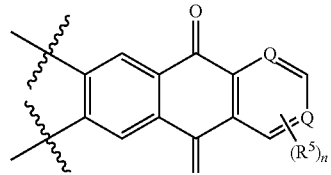
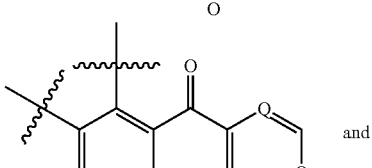
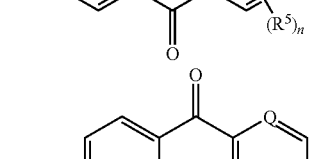
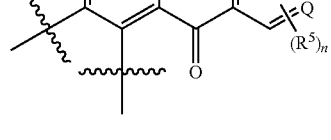
wherein each Q, $Q^1$, $Q^2$, and $Q^3$ is independently CH or N; P is independently O, CH, C=O or $NR^1$; n and $R^5$ is as defined above.
In other embodiments of these compounds, W together with N and Z may form a group having the formula selected from the group consisting of
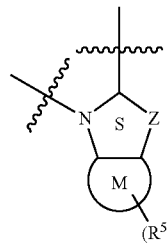 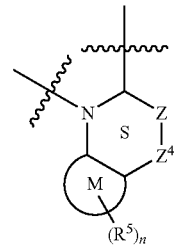 and

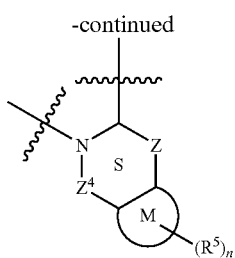

wherein Z is O, S, $NR^2$, $CH_2$ or C=O;
each $Z^4$ is $CR^6$, $NR^2$, or C=O;
$R^6$ is H, or a substituent known in the art, including but not limited to hydroxyl, alkyl, alkoxy, halo, amino, or amido; and
Ring S and M may be saturated or unsaturated.

In some embodiments, W together with N and Z may form a 5- or 6-membered ring that is fused to a phenyl.

In yet another embodiment, the compounds of the present invention have the general formula (TA5-2A) or (TA5-2B):

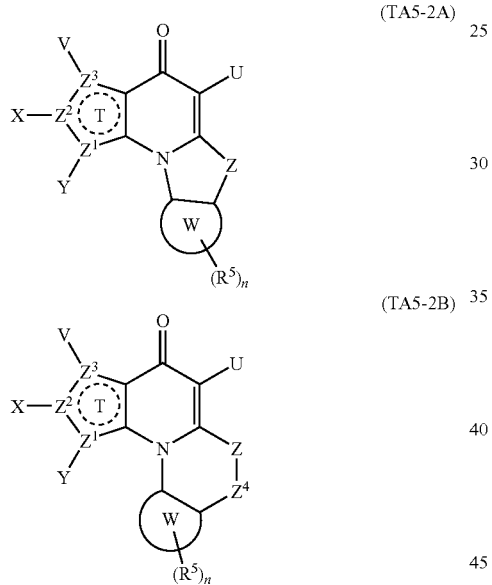

wherein U, V, W, X, Y, Z, $Z^1$, $Z^2$, $Z^3$, $R^5$ and n are as described above for TA5-1;
$Z^4$ is $CR^6$, $NR^2$, or C=O; and
Z and $Z^4$ may optionally form a double bond.

In the above formula (TA5-1), (TA5-2A) and (TA5-2B), U may be $SO_2NR^1R^2$, wherein $R^1$ is H, and $R^2$ is a $C_{1-10}$ alkyl optionally substituted with a heteroatom, a $C_{3-6}$ cycloalkyl, aryl or a 5-14 membered heterocyclic ring containing one or more N, O or S. For example, $R^2$ may be a $C_{1-10}$ alkyl substituted with an optionally substituted morpholine, thiomorpholine, imidazole, aminodithiadazole, pyrrolidine, piperazine, pyridine or piperidine. In other examples, $R^1$ and $R^2$ together with N form an optionally substituted piperidine, pyrrolidine, piperazine, morpholine, thiomorpholine, imidazole, or aminodithiazole.

In other embodiments of these compounds, U is $SO_2NR^1$—$(CR^1_2)_n$—$NR^3R^4$; n is 1-4; each $R^1$ is H or alkyl; and $R^3$ and $R^4$ in $NR^3R^4$ together form an optionally substituted piperidine, pyrrolidine, piperazine, morpholine, thiomorpholine, imidazole, or aminodithiazole. In some examples, U is $SO_2NH$—$(CH_2)_n$—$NR^3R^4$ wherein $R^3$ and $R^4$ together with N form an optionally substituted pyrrolidine, which may be linked to $(CH_2)_n$ at any position in the pyrrolidine ring. In one embodiment, $R^3$ and $R^4$ together with N form an N-methyl substituted pyrrolidine.

In one embodiment, the present invention provides compounds having formula (TA5-1), (TA5-2A) or (TA5-2B), wherein:
each of V and Y if present is independently H or halogen (e.g., chloro or fluoro);
X is —$(R^5)R^1R^2$, wherein $R^5$ is C or N and wherein in each —$(R^5)R^1R^2$, $R^1$ and $R^2$ together may form an optionally substituted aryl or heteroaryl ring;
Z is NH or N-alkyl (e.g., N—$CH_3$);
W together with N and Z forms an optionally substituted 5- or 6-membered ring that is fused with an optionally substituted aryl or heteroaryl ring; and
U is —$SO_2R^5R^6$—$(CH_2)_n$—$CHR^2$—$NR^3R^4$, wherein $R^5$ is $CR^1$ or N; $R^1$ is H or alkyl; $R^6$ is H or $C_{1-10}$ alkyl and wherein in the —$CHR^2$—$NR^3R^4$ moiety each $R^3$ or $R^4$ together with the C may form an optionally substituted heterocyclic or heteroaryl ring, or wherein in the —$CHR^2$—$NR^3R^4$ moiety each $R^3$ or $R^4$ together with the N may form an optionally substituted carbocyclic, heterocyclic, aryl or heteroaryl ring.

In another embodiment, the present invention provides compounds having formula (TA5-1), (TA5-2A) or (TA5-2B), wherein:
V and Y if present is H or halogen (e.g., chloro or fluoro);
X if present is —$(R^5)R^1R^2$, wherein $R^5$ is C or N and wherein in each —$(R^5)R^1R^2$, $R^1$ and $R^2$ together may form an optionally substituted aryl or heteroaryl ring;
Z is NH or N-alkyl (e.g., N—$CH_3$);
W together with N and Z forms an optionally substituted 5- or 6-membered ring that is fused with an optionally substituted aryl or heteroaryl ring; and
U is —$SO_2R^5R^6$—$(CH_2)_n$—$CHR^2$—$NR^3R^4$,
$R^5$ is $CR^1$ or N;
$R^6$ is H or alkyl and wherein in the —$CHR^2$—$NR^3R^4$ moiety each $R^3$ or $R^4$ together with the C may form an optionally substituted heterocyclic or heteroaryl ring, or wherein in the —$CHR^2$—$NR^3R^4$ moiety each $R^3$ or $R^4$ together with the N may form an optionally substituted carbocyclic, heterocyclic, aryl or heteroaryl ring.

In yet another embodiment, the compounds of the present invention have the general formula (TA5-3):

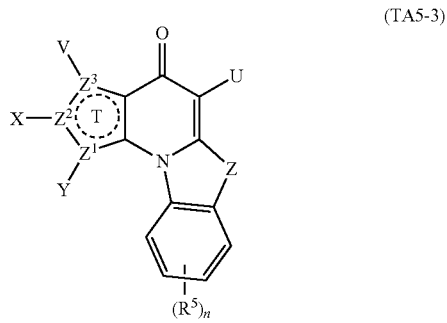

wherein U, V, X, Y, Z, $Z^1$, $Z^2$, $Z^3$, $R^5$ and n are as described above.

In yet another embodiment, the compounds of the present invention have the general formula (TA5-4A) or (TA5-4B):

(TA5-4A)

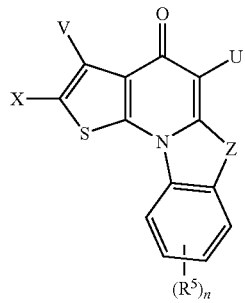

(TA5-4B)

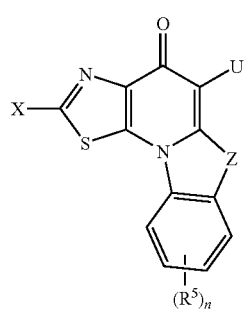

wherein U, V, X, Z, $R^5$ and n are as described above for TA5-1.

Compounds of Formula (TA5-1), and methods for making and using them, are described in U.S. Patent Application Ser. No. 60/811,990, to Pierre, et al., entitled PYRIDINONE ANALOGS, which was filed Jun. 8, 2006, and in U.S. Provisional Patent Application 60/904,694 to Nagasawa, et al., filed on Mar. 1, 2007.

In still another aspect, the therapeutic agent for the combinations of the invention can be a compound of the formula:

(TA6-1)

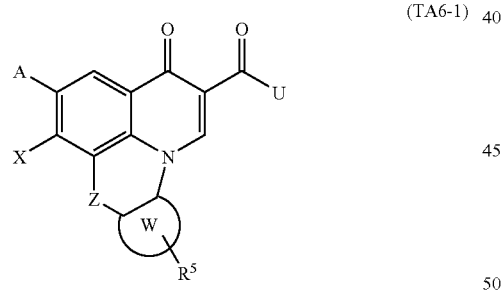

and pharmaceutically acceptable salts, esters and prodrugs thereof, wherein X is H, $OR^2$, $NR^1R^2$, halogen, azido, $SR^2$ or $CH_2R$;

A is H, halogen, $NR^1R^2$, $SR^2$, $OR^2$, $CH_2R^2$, azido or $NR^1$—$(CR^1{}_2)_n$—$NR^3R^4$;

Z is O, S, $NR^1$ or $CH_2$;

U is $R^2$, $OR^2$, $NR^1R^2$ or $NR^1$—$(CR^1{}_2)_n$—$NR^3R^4$ provided U is not H;

W is an optionally substituted aryl or heteroaryl, which may be monocyclic or fused with a single or multiple ring optionally containing a heteroatom;

wherein $R^1$ and $R^2$ together with N in $NR^1R^2$, and $R^3$ and $R^4$ together with N in $NR^3R^4$ may independently form an optionally substituted 5-6 membered ring containing N, and optionally O or S;

$R^1$ and $R^3$ are independently H or a $C_{1-6}$ alkyl; and $R^2$ and $R^4$ are independently H, or a $C_{1-10}$ alkyl or $C_{2-10}$ alkenyl optionally containing one or more non-adjacent heteroatoms selected from N, O, and S, and optionally substituted with a substituted or unsubstituted aryl, heteroaryl, carbocyclic, or heterocyclic ring; or $R^2$ is an optionally cycloalkyl, substituted heterocyclic ring, aryl or heteroaryl;

$R^5$ is a substituent at any position of W and is H, halo, cyano, azido, —$CONHR^1$, $OR^2$, or $C_{1-6}$ alkyl or $C_{2-6}$ alkenyl, each optionally substituted by halo, =O or one or more heteroatoms;

provided X and A both are not H, and further provided that $R^5$ is cyano or —$CONHR^1$ when A is H, halogen or $NR^1R^2$;

or a compound having formula (TA6-1A)

(TA6-1A)

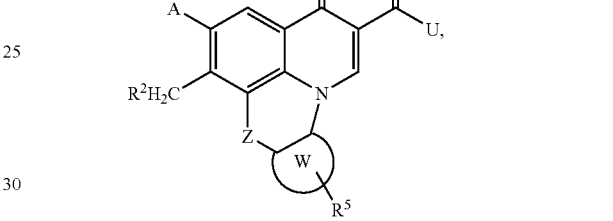

and pharmaceutically acceptable salts, esters and prodrugs thereof;

A is H, halogen, azido, $SR^2$, $OR^2$, $CH_2R^2$, $NR^1R^2$, or $NR^1$—$(CR^1{}_2)_n$—$NR^3R^4$;

Z, U, W, $R^1$, $R^2$, $R^3$ and $R^4$ are as defined in formula TA6-1; and $R^5$ is a substituent at any position of W and is H, halo, cyano, azido, —$CONHR^1$, $OR^2$, or $C_{1-6}$ alkyl or $C_{2-6}$ alkenyl, each optionally substituted by halo, =O or one or more heteroatoms;

wherein each optionally substituted moiety in formula TA6-1 and -1A is substituted with one or more halo, cyano, azido, acetyl, amido, $OR^2$, $NR^1R^2$, carbamate, $C_{1-10}$ alkyl, $C_{2-10}$ alkenyl, each optionally substituted by halo, =O, aryl or one or more heteroatoms selected from N, O and S; or is substituted with an aryl, a carbocyclic or a heterocyclic ring.

In the above formula TA6-1 or TA6-1A, W may be selected from the group consisting of

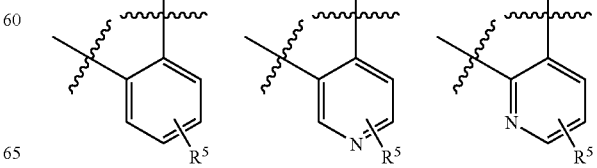

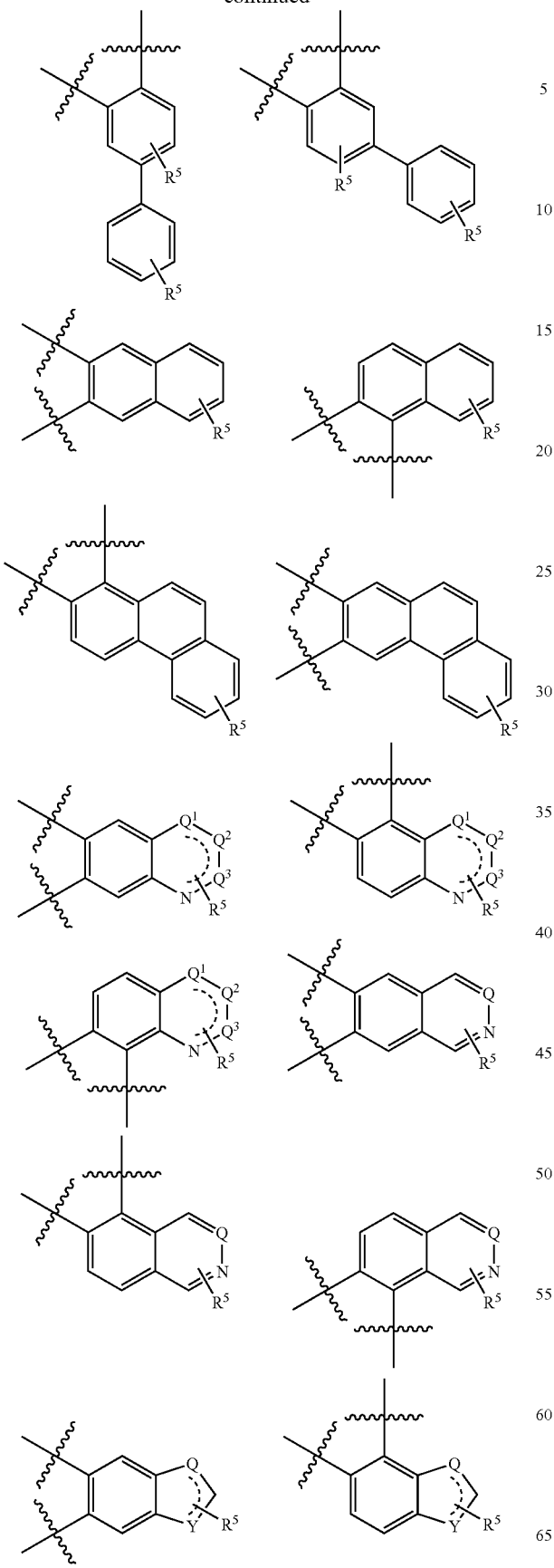
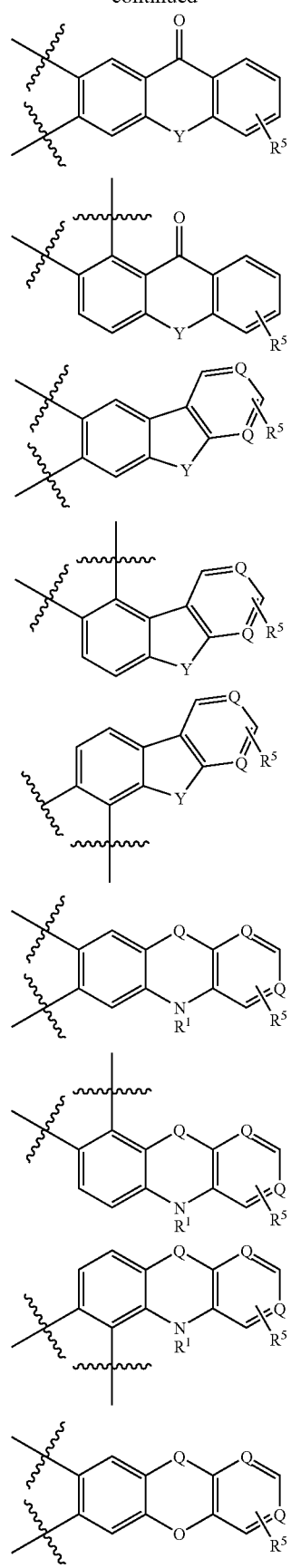

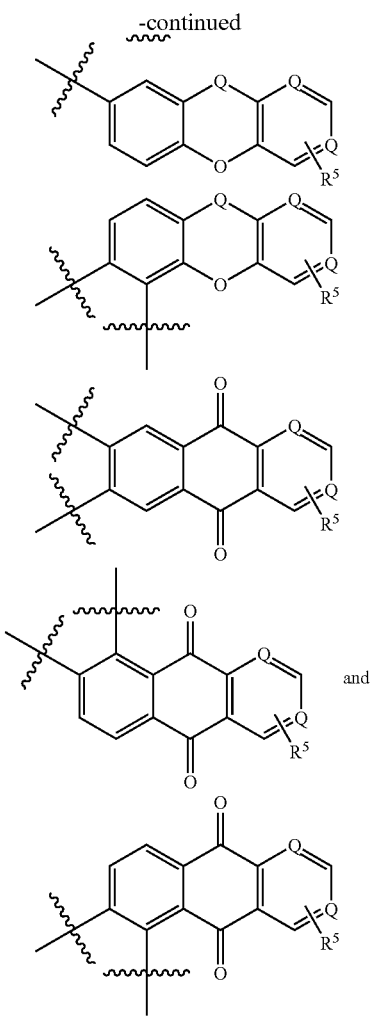

wherein Q, Q¹, Q², and Q³ are independently CH or N;
Y is independently O, CH, =O or NR¹; and
R⁵ is as defined in formula 1.

In some embodiments of these compounds, each W in the above formula TA6-1 or TA6-1A may be an optionally substituted phenyl, pyridine, biphenyl, naphthalene, phenanthrene, quinoline, isoquinoline, quinazoline, cinnoline, phthalazine, quinoxaline, indole, benzimidazole, benzoxazole, benzthiazole, benzofuran, anthrone, xanthone, acridone, fluorenone, carbazolyl, pyrimido[4,3-b]furan, pyrido[4,3-b]indole, pyrido[2,3-b]indole, dibenzofuran, acridine or acridizine. In one embodiment, W is an optionally substituted phenyl.

The compounds of formula (TA6-1), and methods for making and using them, are described in U.S. patent application Ser. No. 11/404,947, to Whitten, et al., which was filed on Apr. 14, 2006, and is entitled QUINOBENZOXAZINE ANALOGS AND METHODS OF USING THEREOF.

The present invention utilizes the above therapeutic agents in combination with at least one modulator. Modulators that can be utilized in combination with a therapeutic agent described above include compounds having structures of Formula (I), (II), (III), (IV), (V) and (VI) as described herein.

The present invention utilizes the above therapeutic agents in combination with at least one modulator. For example, compounds of the invention may be used in combination with PARP inhibitors. Examples of PARP inhibitors are known in the art, and are disclosed, for example, in C. R. Calebrese, et al., *Clin. Cancer Res.* vol. 9, 2711-18 (2003); S. J. Veuger, et al., *Cancer Res.* vol. 63, 6008-15 (2003); C. R. Calabrese et al., *J. Nat'l. Cancer Inst.* 96(1), 56-67 (2004); "Potent Novel PARP Inhibitors," *Expert Reviews in Molecular Medicine*, vol. 7(4) (March 2005); and P. Jagtap, *Nature Rev.: Drug Discovery*, vol. 4, 421-40 (20045). The PARP inhibitors disclosed in these documents are suitable for use in the methods and compositions of the present invention. Additional PARP inhibitors that can be used include, for example, 10-(4-methyl-piperazin-1-ylmethyl)-2H-7-oxa-1,2-diaza-benzo[de]anthracen-3-one (GPI 15427) and 2-(4-methyl-piperazin-1-yl)-5H-benzo[c][1,5]naphthyridin-6-one (GPI 16539). See Di Paola, et al., *Eur. J. Pharmacology*, 527(1-3), 163-71 (2005). Representative, but non-limiting, examples of PARP inhibitors that are suitable for use in the invention include the known compounds shown hereafter, including the pharmaceutically acceptable salts thereof, and individual isomers or mixtures of isomers thereof.

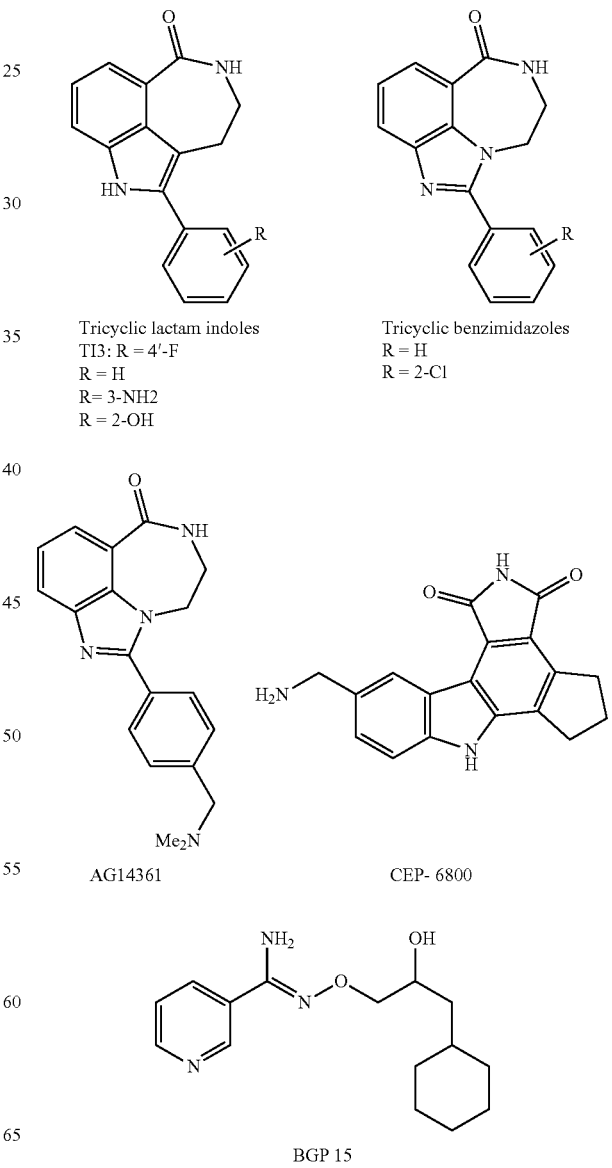

Tricyclic lactam indoles
TI3: R = 4'-F
R = H
R = 3-NH2
R = 2-OH

Tricyclic benzimidazoles
R = H
R = 2-Cl

AG14361

CEP-6800

BGP 15

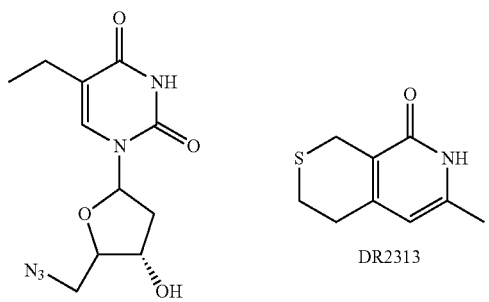
DR2313
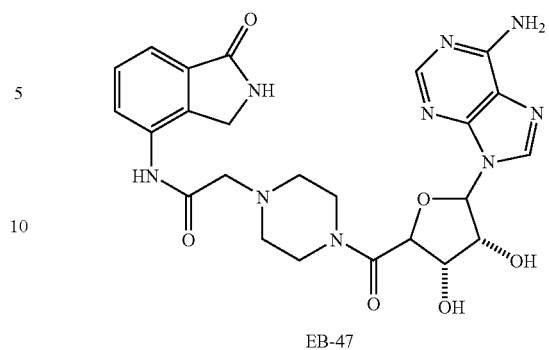
EB-47
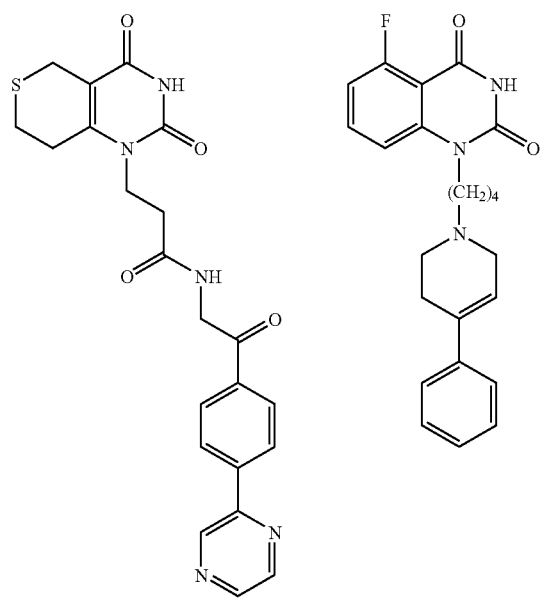
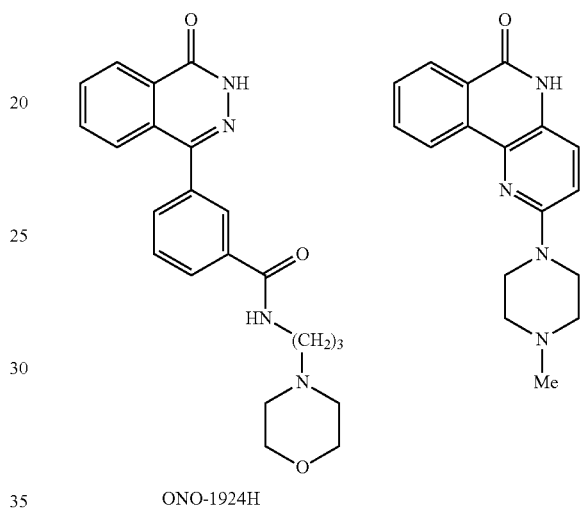
ONO-1924H
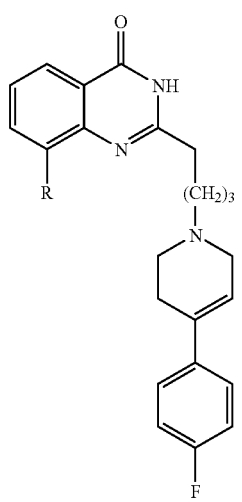
R = Cl
R = Me
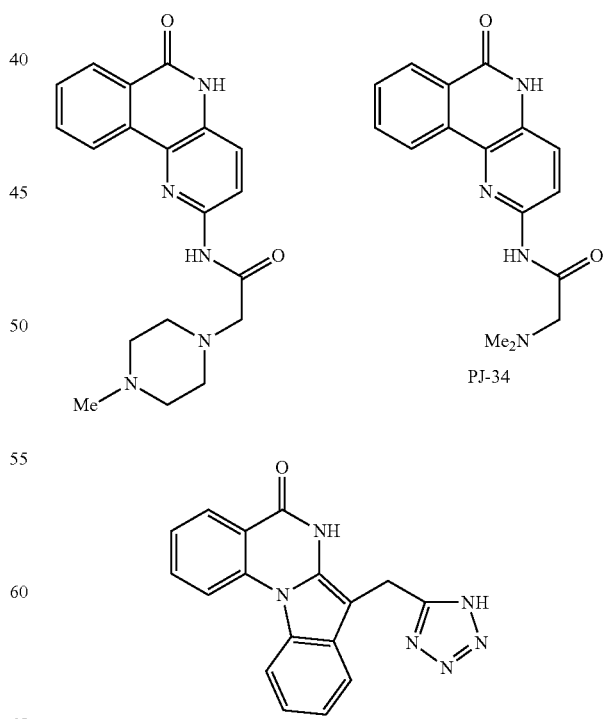
PJ-34

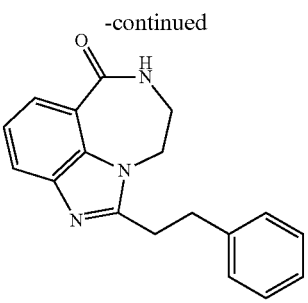

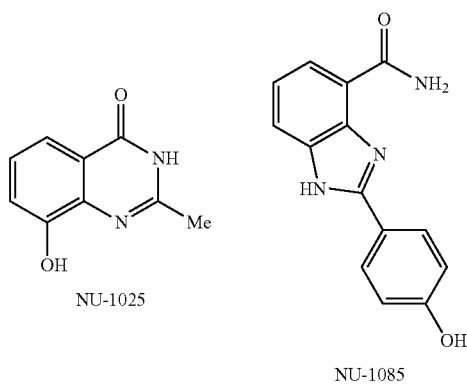

NU-1025

NU-1085

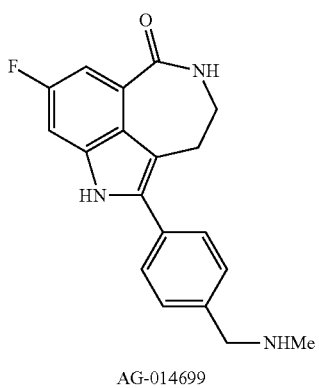

AG-014699

Modulators that can be utilized in combination with a therapeutic agent described above also include compounds having structures of Formula (I), (II), (III), (IV), (V) and (VI) as described herein.

The compound TA1-1A is a preferred therapeutic agent for use in the methods and compositions of the invention. More detail on suitable methods for its formulation and administration are provided in U.S. Provisional Application Ser. No. 60/803,864 to Lim, et al., which was filed on Jun. 3, 2006.

The invention also in part provides pharmaceutical compositions comprising at least one therapeutic agent within the scope of the invention as described herein in combination with at least one modulator. Optionally, the composition may comprise a diluent or other pharmaceutically acceptable excipients.

For administration to animal or human subjects, the appropriate dosage of the therapeutic agent is typically 0.01-15 mg/kg, preferably 0.1-10 mg/kg. Dosage levels are dependent on the nature of the condition, drug efficacy, the condition of the patient, the judgment of the practitioner, and the frequency and mode of administration; however, optimization of such parameters is within the ordinary level of skill in the art.

Similarly, the dosage of a modulator, such as a compound of Formula (I), (II), (III), (IV), (V) or (VI) as described herein, is typically between about 0.01-150 mg/kg, and about 0.1-100 mg/kg. A modulator may be separately active for treating a cancer. For combination therapies described above, when used in combination with a therapeutic agent, the dosage of a modulator will frequently be two-fold to ten-fold lower than the dosage required when the modulator is used alone to treat the same condition or subject. Determination of a suitable amount of the modulator for use in combination with a therapeutic agent is readily determined by methods known in the art.

Also provided are methods for modulating the activity of a CK protein, which comprises contacting a system comprising the CK protein with a composition described herein in an amount effective for modulating (e.g., inhibiting) the activity of the protein. The system in such embodiments can be a cell-free system or a system comprising cells. Also provided are methods for reducing cell proliferation, and optionally inducing apoptosis, which comprises contacting cells with a composition or a combination therapy as described herein, wherein a therapeutic agent is administered in an amount effective to reduce proliferation of the cells, and a CK inhibitor is administered in an amount sufficient to enhance the efficacy of the therapeutic agent. The cells in such embodiments can be in a cell line, in a tissue or in a subject (e.g., a research animal or human).

The invention also in part provides methods for treating a condition related to aberrant cell proliferation. For example, provided are methods of treating a cell proliferative condition in a subject, which comprises administering a therapeutic agent described herein and a CK inhibitor described herein to a subject in need of treatment for a cell proliferative disorder; the therapeutic agent and the CK inhibitor are administered in amounts effective to treat the cell proliferative condition. The subject may be a research animal (e.g., rodent, dog, cat, monkey), optionally containing a tumor such as a xenograft tumor (e.g., human tumor), for example, or may be a human.

A cell proliferative condition sometimes is a tumor or non-tumor cancer, including but not limited to, cancers of the colorectum, breast, lung, liver, pancreas, lymph node, colon, prostate, brain, head and neck, skin, liver, kidney, blood and heart (e.g., leukemia, lymphoma, carcinoma).

Any suitable formulation of the therapeutic agent and the CK inhibitor can be prepared for administration, either together or separately. Any suitable route of administration may be used for each component, including but not limited to oral, parenteral, intravenous, intramuscular, transdermal, topical and subcutaneous routes. The two substances used together (CK inhibitor and therapeutic agent) may be administered separately or together. When administered together, they may be in separate dosage forms, or they may be combined into a single combination drug. Thus, provided herein are pharmaceutical compositions comprising a therapeutic agent as described herein and at least one CK inhibitor, and a pharmaceutically acceptable excipient.

All references cited herein, including patents, patent applications, and publications, are hereby incorporated by reference in their entireties, whether previously specifically incorporated or not. As used herein, the terms "a", "an", and "any" are each intended to include both the singular and plural forms.

The following examples illustrate and do not limit the invention.

EXAMPLE 1

Preparation of Methyl 5-chlorobenzo[c][2,6]-naphthyridine-8-carboxylate

Process 1

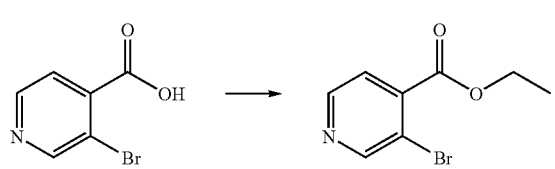

3-Bromo-4-pyridine carboxylic acid (3.0 g, 14.9 mmol) in ethanol (100 mL) was treated with concentrated sulfuric acid (5 mL). The mixture was brought to reflux at which time everything went into solution. After 12 hours at reflux, LCMS indicated that the reaction was complete. The reaction mixture was cooled to room temperature and concentrated on a rotary evaporator to a third of its original volume. The mixture was then diluted with 250 mL of ethyl acetate and washed twice with saturated aqueous sodium bicarbonate. Concentration on a rotary evaporator yielded 3.25 g of the ethyl ester as a yellowish oil which was sufficiently pure enough for subsequent chemical transformations. LCMS (ESI) 216.2 (M+1)$^+$.

Process 2

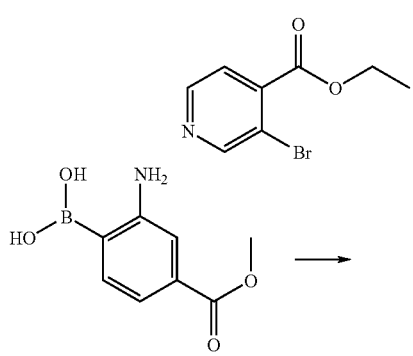

Ethyl 3-bromo-4-pyridine carboxylate 1.15 g, 5.0 mmol), 2-amino-4-methoxycarbonyl-phenylboronic acid (1.04 g, 4.5 mmol), sodium acetate (1.64 g, 20 mmol), 1,1'-bis(diphenylphosphino)ferrocene palladium (II) chloride (complexed with dichloromethane) (182 mg, 0.25 mmol) and dimethylformamide (7.5 mL) were combined in a flask. The flask was evacuated and filled with nitrogen twice and heated to 125° C. with stirring for 12 hours or until LCMS indicated the absence of any starting material. The mixture was cooled to room temperature and water (100 mL) was added to form a brown precipitate. The precipitate was filtered to yield 637 mg of methyl 5-oxo-5,6-dihydrobenzo[c][2,6]naphthyridine-8-carboxylate. LCMS (ESI) 255.4 (M+1)$^+$.

Process 3

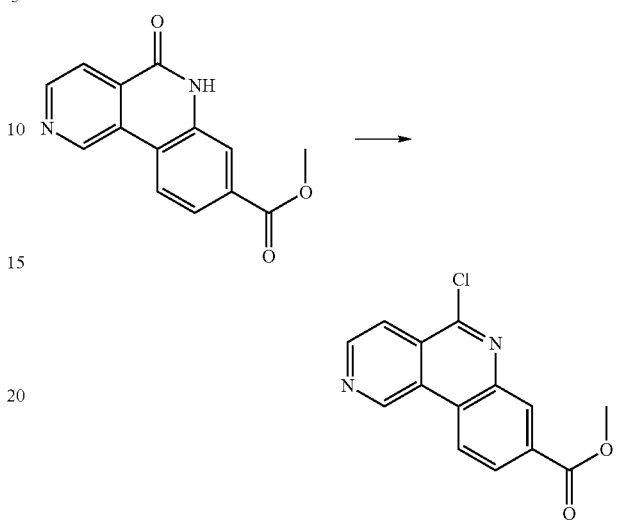

Methyl 5-oxo-5,6-dihydrobenzo[c][2,6]naphthyridine-8-carboxylate (200 mg, 0.787 mmol) was combined with phosphorus oxychloride (1 mL) and heated to reflux. After 2 hours, LCMS indicated the absence of any starting material. The volatiles were removed under reduced pressure. The residue was taken up in dichloromethane (50 mL) and washed twice with saturated aqueous sodium bicarbonate. The organic phase was dried over sodium sulfate and concentrated on a rotary evaporator to give methyl 5-chlorobenzo[c][2,6]naphthyridine-8-carboxylate (140 mg) as a grayish solid. LCMS (ESI) 273.3 (M+1)$^+$.

EXAMPLE 2

Preparation of Methyl 5-chloropyrimido[4,5-c]quinoline-8-carboxylate

Process 4

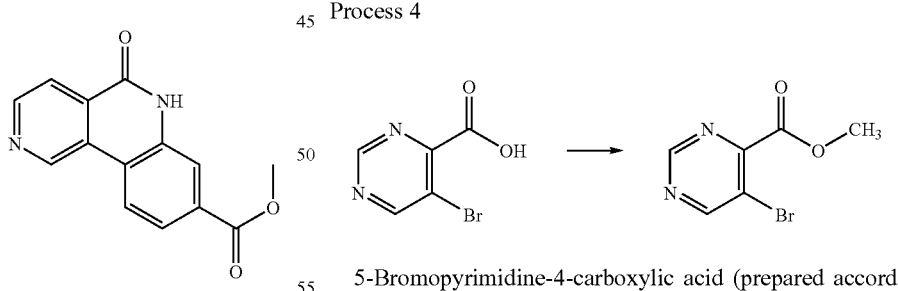

5-Bromopyrimidine-4-carboxylic acid (prepared according to the procedure described in U.S. Pat. No. 4,110,450) (1.0 eq, 6.14 g, 30.2 mmol) was suspended in CH$_2$Cl$_2$ (100 ml). Oxalylchloride (1.1 eq, 2.9 ml, 33.0 mmol) was added followed by 2 drops of DMF. The mixture was stirred at room temperature overnight and the volatiles were removed in vacuo. The residue was taken in MeOH (50 ml) and heated. After evaporation of MeOH in vacuo the compound was dissolved in CH$_2$Cl$_2$ and poured on a prepacked silica gel column. The material was eluted using 20% Ethyl acetate in hexanes. Evaporation of the solvent provided methyl-5-bromopyrimidine-4-carboxylate as a light orange crystalline solid (2.54 g, 39% yield). LCMS (ES): 95% pure, m/z 217

[M]+; 219 [M+2]+; 1H NMR (CDCl3, 400 MHz) δ 4.04 (s, 3H), 9.02 (s, 1H), 9.21 (s, 1H) ppm.

Process 5

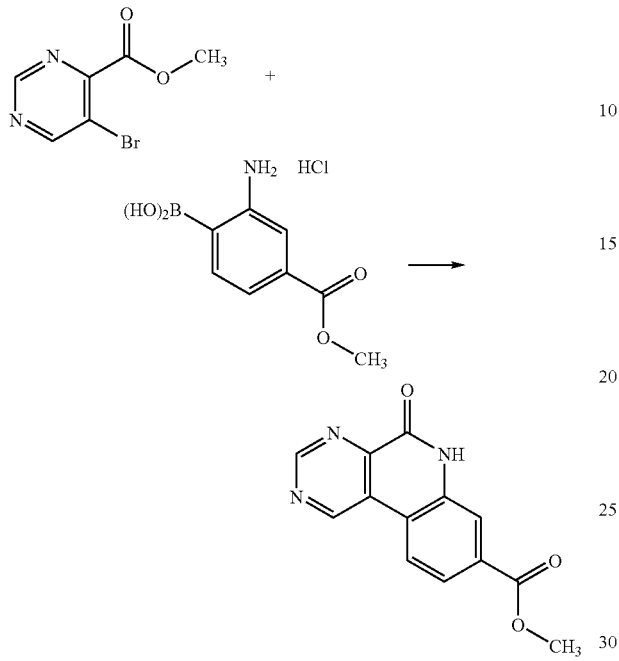

Sodium acetate (4.0 eq, 1.92 g, 23.41 mmol) and 1,1'-bis(diphenylphosphino)ferrocene palladium (II) chloride (complexed with dichloromethane) (0.05 eq, 214 mg, 0.29 mmol) were added to a mixture of methyl-5-bromopyrimidine-4-carboxylate (1.0 eq, 1.27 g, 5.85 mmol), and 2-amino-4-(methoxycarbonyl)phenylboronic acid hydrochloride (1.0 eq, 1.35 g, 5.85 mmol) in anhydrous DMF (10 ml). The mixture was stirred under nitrogen atmosphere at 120° C. for 18 hours. Water and brine were added and the resulting solid impurities filtered off. The material was extracted with $CH_2Cl_2$ (4×) and the combined extracts dried over $Na_2SO_4$. After evaporation of $CH_2Cl_2$, the remaining DMF was evaporated by heating the residue in vacuo. The resulting solid was triturated in $CH_2Cl_2$, filtered and dried to provide methyl 5-oxo-5,6-dihydropyrimido[4,5-c]quinoline-8-carboxylate as a beige solid (127 mg, 8.5% yield). LCMS (ES): >80% pure, m/z 256 [M+1]+; 1H NMR (DMSO-d6, 400 MHz) δ 3.79 (s, 3H), 7.81 (d, J=8.0, 1H), 8.68 (d, J=8.8, 1H), 9.49 (s, 1H), 10.19 (s, 1H), 12.37 (s, 1H) ppm.

Process 6

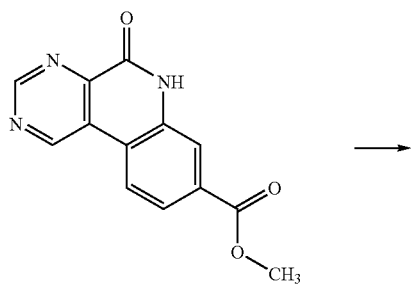

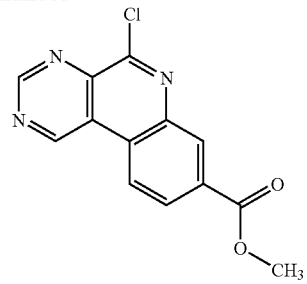

In a vial, methyl 5-oxo-5,6-dihydropyrimido[4,5-c]quinoline-8-carboxylate (1.0 eq, 151 mg, 0.59 mmol) was mixed in toluene (1 ml) with DIEA (1.5 eq, 155 ul, 0.89 mmol) and $POCl_3$ (5 eq, 270 ul, 3.0 mmol). The mixture was stirred at 120° C. for 1 hour and cooled down to room temperature. After adding ice and water the compound was extracted with $CH_2Cl_2$ (4×). The solution was filtered over $Na_2SO_4$ and filtered through a pad of celite. After evaporation of the volatiles, the material was triturated in a mixture of ethyl acetate and hexanes, filtered and dried to afford methyl 5-chloropyrimido[4,5-c]quinoline-8-carboxylate as a light brown fluffy solid (115 mg, 71% yield). LCMS (ES): 95% pure, m/z 274 [M+1]+. 1H NMR (DMSO-d6, 400 MHz) δ 3.96 (s, 3H), 8.37 (dd, J=1.6, J=8.4, 1H), 8.60 (d, J=1.6, 1H), 9.15 (d, J=8.8, 1H), 9.74 (s, 1H), 10.61 (s, 1H) ppm.

EXAMPLE 3

Preparation of methyl 5-chloro-3-(methylthio)pyrimido[4,5-c]quinoline-8-carboxylate Process 7

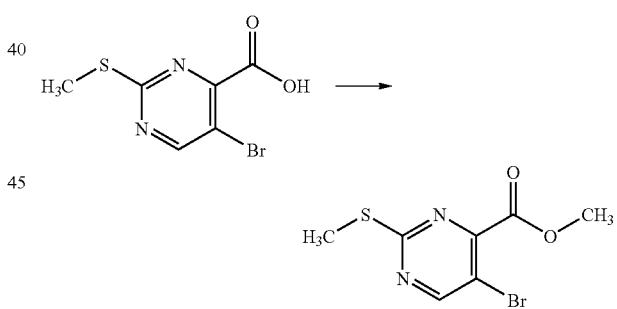

Methyl-5-bromo-2-(methylthio)pyrimidine-4-carboxylate was prepared according to the procedure used in Process 4 for the preparation of methyl-5-bromopyrimidine-4-carboxylate. LCMS (ES): >90% pure, m/z 263 [M]+, 265 [M+2]+; 1H NMR (CDCl3, 400 MHz) δ 2.59 (s, 3H), 4.00 (s, 3H), 8.71 (s, 1H) ppm.

Process 8

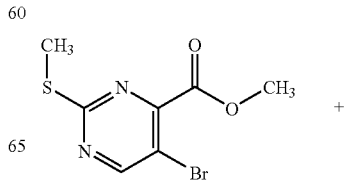

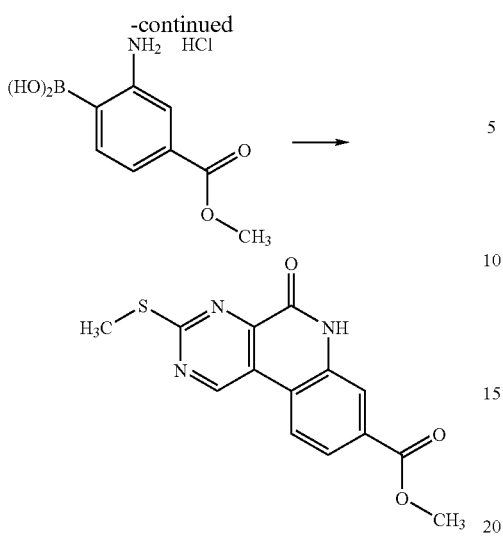

In a microwave vessel, methyl 5-bromo-2-(methylthio)pyrimidine-4-carboxylate (1.0 eq, 274 mg, 1.18 mmol), 2-amino-4-(methoxycarbonyl)phenylboronic acid hydrochloride (1.2 eq, 329 mg, 1.42 mmol), and sodium acetate (3.0 eq, 291 mg, 3.55 mmol) were mixed in anhydrous DMF (2 ml). The mixture was degassed by bubbling nitrogen gas in the solution for 10 min and the reaction heated under microwaves at 120° C. for 30 min. After cooling down the expected material crashed out of NMP. The solid was filtered, suspended in water filtered and dried. The material was triturated in AcOEt and filtered give a yellow solid. The same procedure was repeated 9 times using the same amounts of materials to provide methyl 3-(methylthio)-5-oxo-5,6-dihydropyrimido[4,5-c]quinoline-8-carboxylate (283 mg, 10% yield). LCMS (ES): >95% pure, m/z 302 [M+1]$^+$, $^1$H NMR (DMSO-d$_6$, 400 MHz) δ 2.71 (s, 3H), 3.89 (s, 3H), 7.80 (dd, J=1.6, J=8.4, 1H), 7.97 (d, J=1.6, 1H), 8.59 (d, J=8.8, 1H), 9.98 (s, 1H), 12.34 (s, 1H) ppm.
Process 9

Methyl 3-(methylthio)-5-oxo-5,6-dihydropyrimido[4,5-c] quinoline-8-carboxylate (1.0 eq, 279 mg, 0.926 mmol) was suspended in toluene (2 ml). POCl$_3$ (2 ml) and DIEA (0.5 ml) were added and the mixture stirred at 120° C. for 5 hours. The volatiles were removed in vacuo and CH$_2$Cl$_2$ was added. The organic phase was washed with saturated aqueous sodium bicarbonate, washed with water and dried over Na$_2$SO$_4$. The solution was filtered through a pad of celite and the solvents removed in vacuo. The material was triturated in hexanes and AcOEt, filtered and dried to provide methyl 5-chloro-3-(methylthio)pyrimido[4,5-c]quinoline-8-carboxylate as a beige solid (184 mg, 63% yield). LCMS (ES): >95% pure, m/z 320 [M+1]$^+$, 322 [M+3]$^+$.

EXAMPLE 4

Preparation of methyl 3-(methylthio)-5-phenylpyrimido[4,5-c]quinoline-8-carboxylate

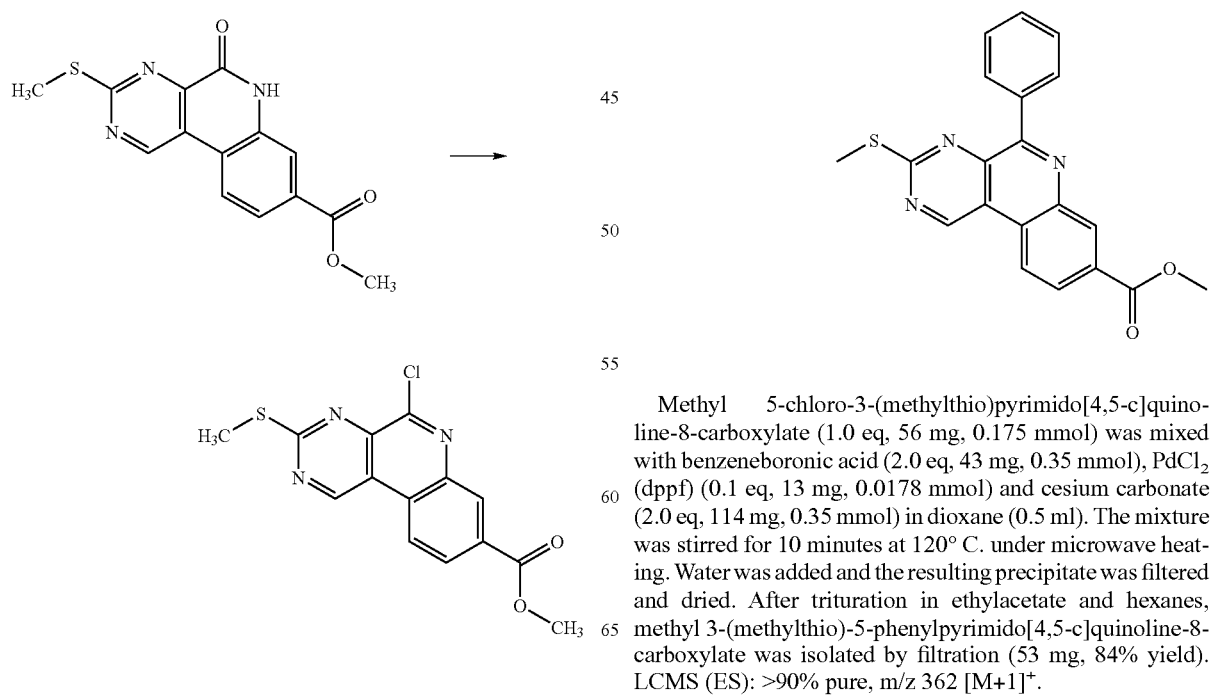

Methyl 5-chloro-3-(methylthio)pyrimido[4,5-c]quinoline-8-carboxylate (1.0 eq, 56 mg, 0.175 mmol) was mixed with benzeneboronic acid (2.0 eq, 43 mg, 0.35 mmol), PdCl$_2$ (dppf) (0.1 eq, 13 mg, 0.0178 mmol) and cesium carbonate (2.0 eq, 114 mg, 0.35 mmol) in dioxane (0.5 ml). The mixture was stirred for 10 minutes at 120° C. under microwave heating. Water was added and the resulting precipitate was filtered and dried. After trituration in ethylacetate and hexanes, methyl 3-(methylthio)-5-phenylpyrimido[4,5-c]quinoline-8-carboxylate was isolated by filtration (53 mg, 84% yield). LCMS (ES): >90% pure, m/z 362 [M+1]$^+$.

EXAMPLE 5

Preparation of methyl 3-(methylsulfonyl)-5-phenylpyrimido[4,5-c]quinoline-8-carboxylate

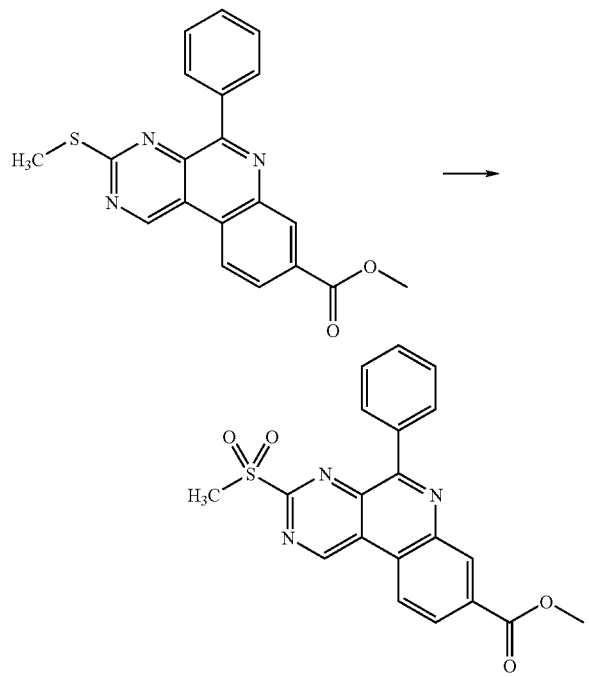

methyl 3-(methylthio)-5-phenylpyrimido[4,5-c]quinoline-8-carboxylate (1.0 eq, 44 mg, 0.1219 mmol) was dissolved in CH$_2$Cl$_2$ (1 ml). mcpba (3.0 eq, 82 mg, 0.366 mmol) was added and the mixture stirred at room temperature for 2.5 hours. CH$_2$Cl$_2$ was added and the organic phase washed with saturated NaHCO$_3$, then water. After drying over Na$_2$SO$_4$ and evaporation of the solvent, methyl 3-(methylsulfonyl)-5-phenylpyrimido[4,5-c]quinoline-8-carboxylate was isolated as a solid. LCMS (ES): >95% pure, m/z 394 [M+1]$^+$.

EXAMPLE 6

Preparation of methyl 3-(cyclopropylamino)-5-phenylpyrimido[4,5-c]quinoline-8-carboxylate

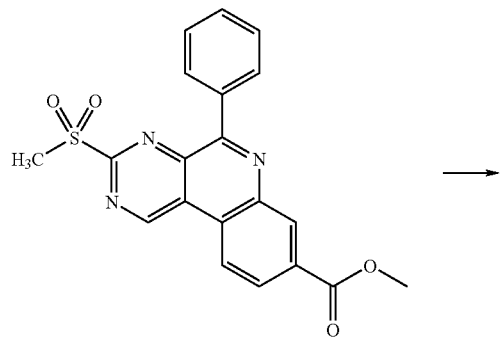

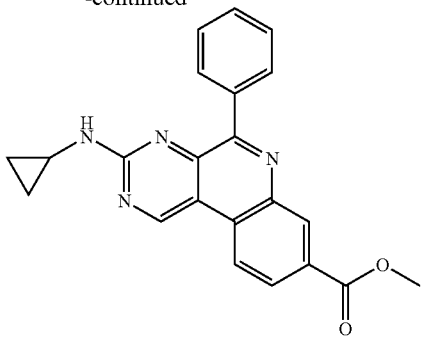

methyl 3-(methylsulfonyl)-5-phenylpyrimido[4,5-c]quinoline-8-carboxylate (1.0 eq, 117 mg, 0.298 mmol) was mixed in a vial with cylopropylamine (3.0 eq, 62 ul, 0.89 mmol) in NMP (2 ml). The mixture was stirred at 60° C. for 50 minutes. Water was added and the resulting solid filtered. The material was suspended in AcOEt/hexanes and filtered to afford methyl 3-(cyclopropylamino)-5-phenylpyrimido[4,5-c]quinoline-8-carboxylate as a yellow solid (86 mg, 78% yield). LCMS (ES): >95% pure, m/z 371 [M+1]$^+$.

EXAMPLE 7

Preparation of 3-(cyclopropylamino)-5-phenylpyrimido[4,5-c]quinoline-8-carboxylic acid

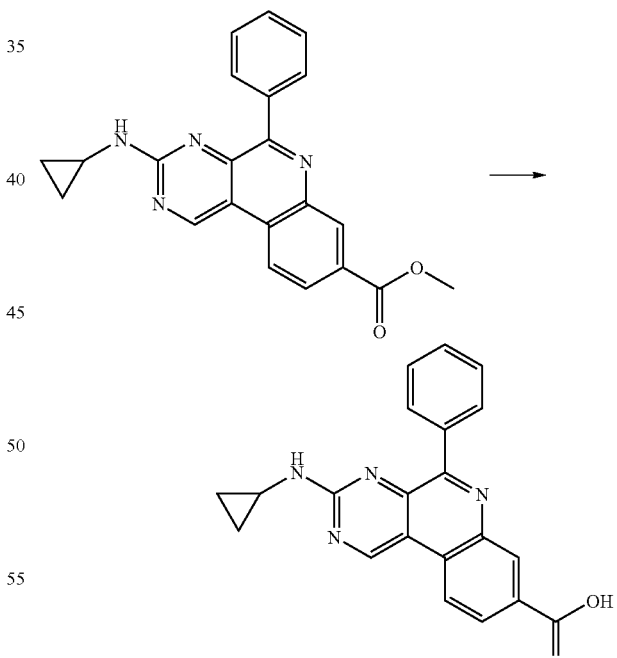

methyl 3-(cyclopropylamino)-5-phenylpyrimido[4,5-c]quinoline-8-carboxylate (1.0 eq, 81 mg, 0.219 mmol) was stirred in EtOH (3 ml) and 6N NaOH (1 ml) at 60° C. for 15 hours. Water was added and the mixture acidified using 6 N HCl. The solid was filtered, washed with water and dried. After trituration in MeOH and filtration, 3-(cyclopropylamino)-5-phenylpyrimido[4,5-c]quinoline-8-carboxylic acid was isolated as yellow solid (57 mg, 73% yield)). LCMS (ES): >95% pure, m/z 357 [M+1]+.

EXAMPLE 8

Preparation of N-cyclopropyl-3-(cyclopropylamino)-5-phenylpyrimido[4,5-c]quinoline-8-carboxamide

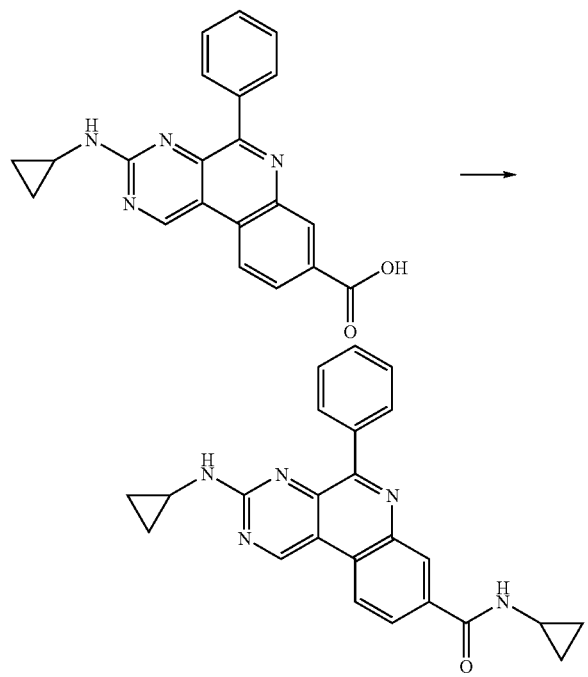

3-(cyclopropylamino)-5-phenylpyrimido[4,5-c]quinoline-8-carboxylic (1.0 eq, 25 mg) was reacted in NMP (0.5 ml), HOBt.H₂O (2.0 eq, 19 mg), DIEA (4.0 eq, 50 ul), EDCI (2.0 eq, 27 mg) and 4.0 equivalent of cyclopropylamine at 70° C. for 1.5 hours. Water was added and the solid isolated by filtration. After trituration in AcOEt/hexanes, filtration and drying, N-cyclopropyl-3-(cyclopropylamino)-5-phenylpyrimido[4,5-c]quinoline-8-carboxamide was isolated as a solid (21 mg). LCMS (ES): >95% pure, m/z 396 [M+1]+.

EXAMPLE 9

Preparation of Methyl 5-phenylbenzo[c][2,6]naphthyridine-8-carboxylate

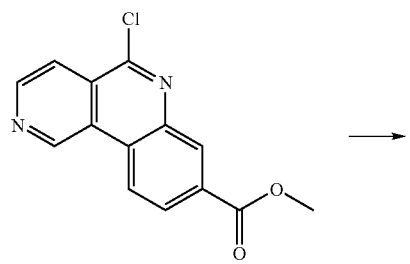

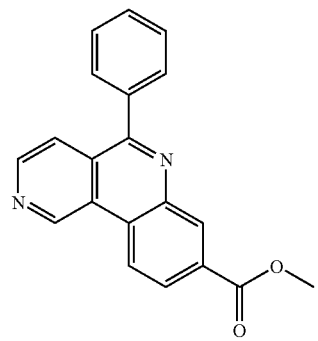

Methyl 5-phenylbenzo[c][2,6]naphthyridine-8-carboxylate was prepared from methyl 5-chlorobenzo[c][2,6]naphthyridine-8-carboxylate using the same protocol as described in Example 4 (91% yield). LCMS (ES): >95% pure, m/z 315 [M+1]+.

EXAMPLE 10

Preparation of 5-phenylbenzo[c][2,6]naphthyridine-8-carboxylic acid

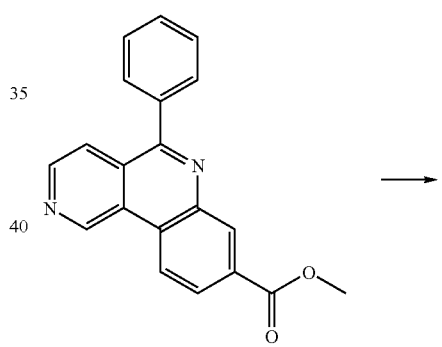

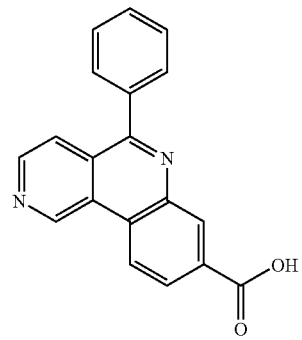

methyl 5-phenylbenzo[c][2,6]naphthyridine-8-carboxylate (147 mg, 0.468 mmol) was reacted with EtOH (3 ml) and 6 N NaOH (1 ml) at 60° C. for 2 hours. Water was added and the mixture acidified using 6N HCl. The solid was filtered and washed with water. The material was triturated in AcOEt/hexanes, filtered and dried to afford 5-phenylbenzo[c][2,6]naphthyridine-8-carboxylic acid as an off-white solid (121 mg, 86% yield). LCMS (ES): >95% pure, m/z 301[M+1]+.

EXAMPLE 11
The molecules depicted in the following table were prepared using similar chemistries in the presence of appropriate boronic acids or esters, as well as appropriate amines.
TABLE 1
Representative compounds and data
| Structure | MW | LCMS m/z [M + 1]+ |
|---|---|---|
| 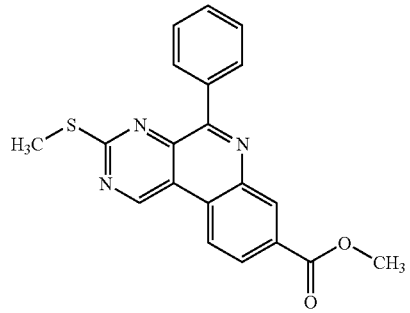 | 361.42 | 362 |
| 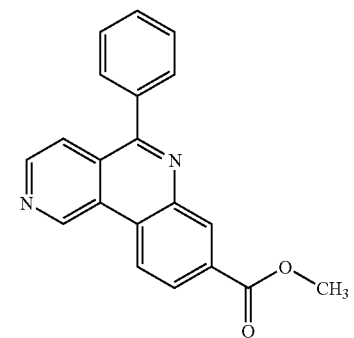 | 314.34 | 315 |
| 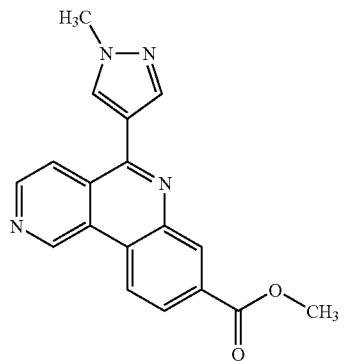 | 318.33 | 319 |
| 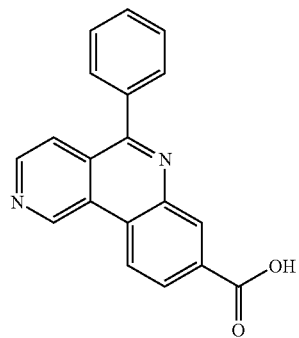 | 300.31 | 301 |
TABLE 1-continued
Representative compounds and data
| Structure | MW | LCMS m/z [M + 1]+ |
|---|---|---|
| 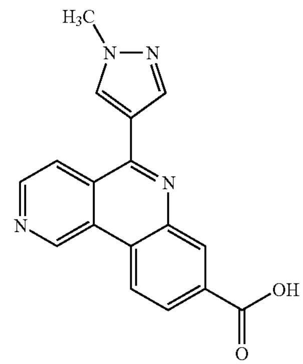 | 304.30 | 305 |
| 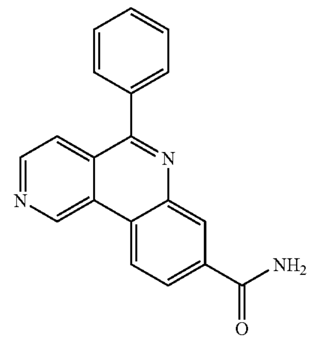 | 299.33 | 300 |
| 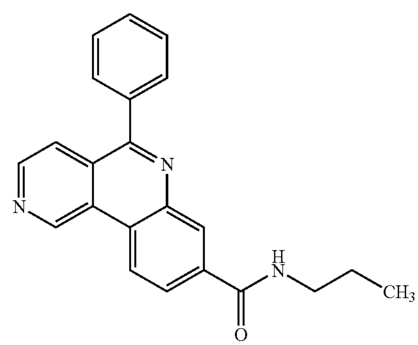 | 341.41 | 342 |
| 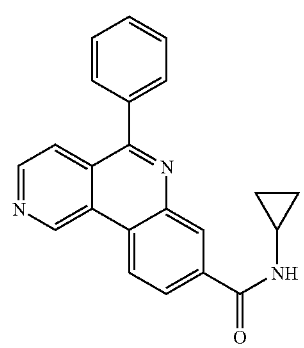 | 339.39 | 340 |

TABLE 1-continued

Representative compounds and data

| Structure | MW | LCMS m/z [M + 1]+ |
|---|---|---|
| (structure) | 327.38 | 328 |
| (structure) | 303.32 | 304 |
| (structure) | 345.40 | 346 |
| (structure) | 343.38 | 344 |

TABLE 1-continued

Representative compounds and data

| Structure | MW | LCMS m/z [M + 1]+ |
|---|---|---|
| (structure) | 331.37 | 332 |
| (structure) | 382.46 | 383 |
| (structure) | 396.48 | 397 |
| (structure) | 357.36 | 358 |

TABLE 1-continued
Representative compounds and data
| Structure | MW | LCMS m/z [M + 1]+ |
|---|---|---|
| 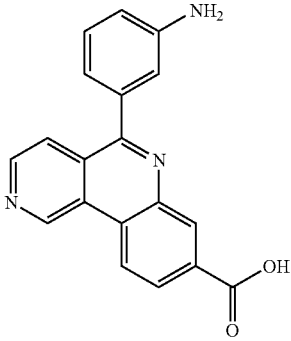 | 315.33 | 316 |
| 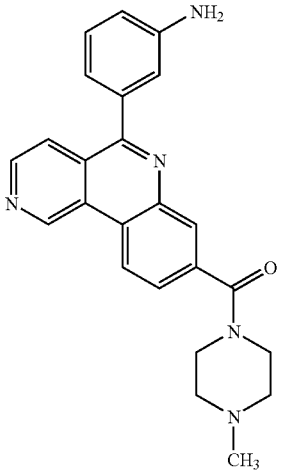 | 397.47 | 398 |
| 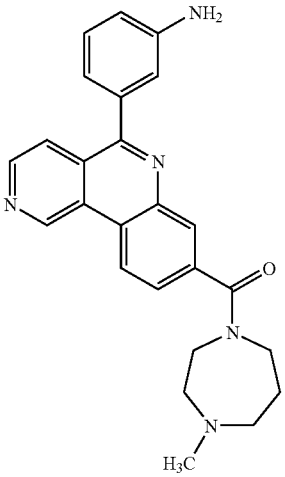 | 411.50 | 412 |
| 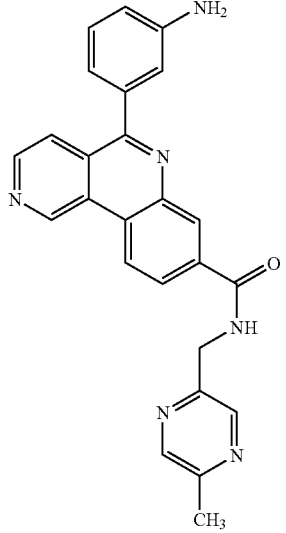 | 420.47 | 421 |
| 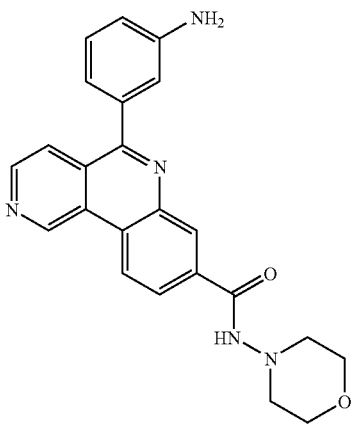 | 399.45 | 400 |
| 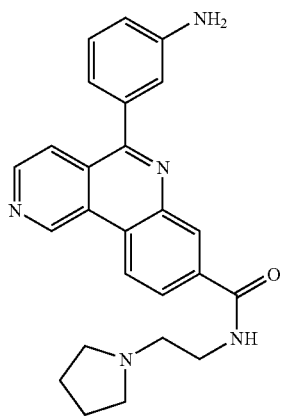 | 411.50 | 412 |

TABLE 1-continued

Representative compounds and data

| Structure | MW | LCMS m/z [M + 1]+ |
|---|---|---|
| (structure with aniline NH₂, pyrido-fused core, carboxamide to (1-methylpiperidin-2-yl)methyl) | 425.53 | 426 |
| (structure with 3-acetamidophenyl, pyrido-fused core, carboxamide to 4-methylpiperazine) | 439.51 | 440 |
| (structure with 3-acetamidophenyl, pyrido-fused core, carboxamide to 4-methyl-1,4-diazepane) | 453.54 | 454 |
| (structure with 3-acetamidophenyl, pyrido-fused core, carboxamide NH to (5-methylpyrazin-2-yl)methyl) | 462.50 | 463 |
| (structure with 3-acetamidophenyl, pyrido-fused core, carboxamide NH to morpholin-4-yl) | 441.48 | 442 |
| (structure with 3-acetamidophenyl, pyrido-fused core, carboxamide NH to 2-(pyrrolidin-1-yl)ethyl) | 453.54 | 454 |

TABLE 1-continued

Representative compounds and data

| Structure | MW | LCMS m/z [M + 1]+ |
|---|---|---|
| (structure) | 467.56 | 468 |
| (structure) | 365.41 | 366 |
| (structure) | 393.42 | 394 |
| (structure) | 370.40 | 371 |
| (structure) | 356.38 | 357 |
| (structure) | 355.39 | 356 |
| (structure) | 395.46 | 396 |
| (structure) | 397.41 | 398 |

TABLE 1-continued
Representative compounds and data
| Structure | MW | LCMS m/z [M + 1]+ |
|---|---|---|
| 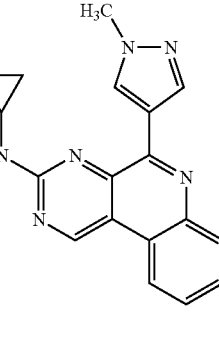 | 374.40 | 375 |
| 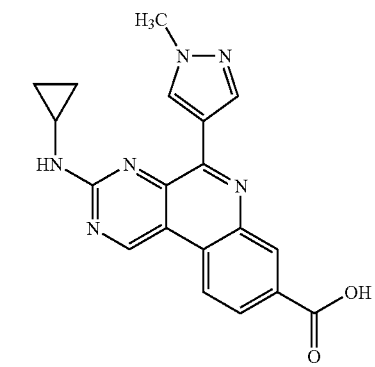 | 360.37 | 361 |
| 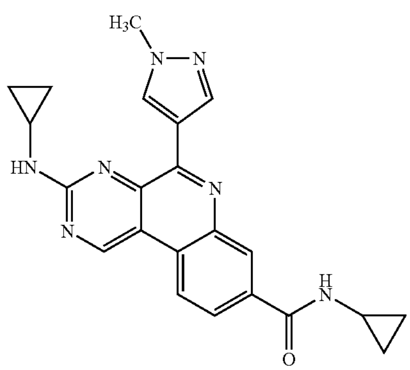 | 399.45 | 400 |
| 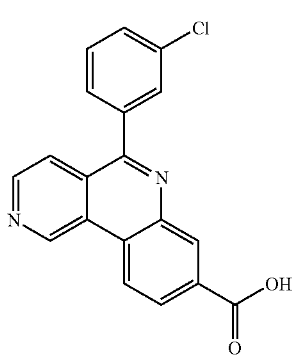 | 334.76 | 336 |
TABLE 1-continued
Representative compounds and data
| Structure | MW | LCMS m/z [M + 1]+ |
|---|---|---|
| 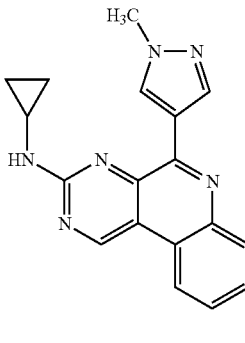 | 314.34 | 315 |
| 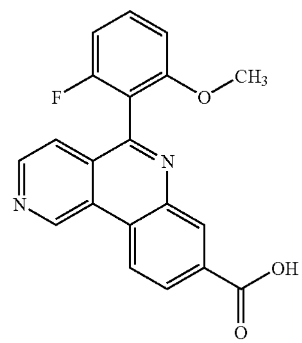 | 348.33 | 349 |
| 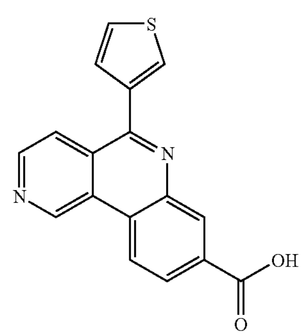 | 306.34 | 307 |
| 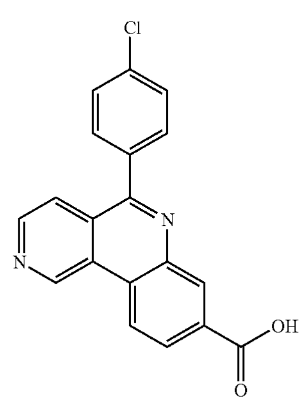 | 334.76 | 336 |

TABLE 1-continued

Representative compounds and data

| Structure | MW | LCMS m/z [M + 1]+ |
|---|---|---|
| (4-chlorophenyl compound) | 290.75 | 292 |
| (2-methylphenyl compound) | 270.33 | 271 |
| (3-chlorophenyl compound) | 290.75 | 292 |
| (2-fluorophenyl carboxylic acid compound) | 318.30 | 319 |
| (3-fluorophenyl carboxylic acid compound) | 318.30 | 319 |
| (4-fluorophenyl carboxylic acid compound) | 318.30 | 319 |
| (2-trifluoromethoxyphenyl carboxylic acid compound) | 384.31 | 385 |
| (3-cyanophenyl carboxylic acid compound) | 325.32 | 326 |

TABLE 1-continued
Representative compounds and data
| Structure | MW | LCMS m/z [M + 1]+ |
|---|---|---|
| 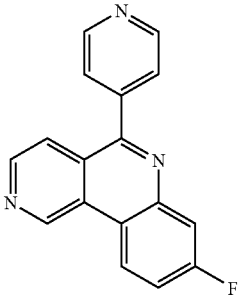 | 275.28 | 276 |
| 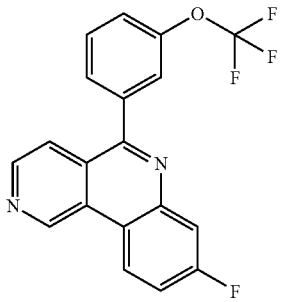 | 358.29 | 359 |
| 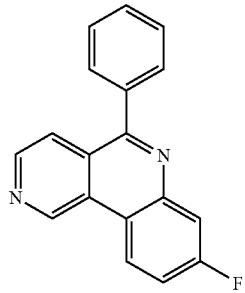 | 274.29 | 275 |
| 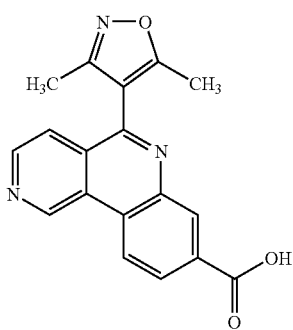 | 319.31 | 320 |
TABLE 1-continued
Representative compounds and data
| Structure | MW | LCMS m/z [M + 1]+ |
|---|---|---|
| 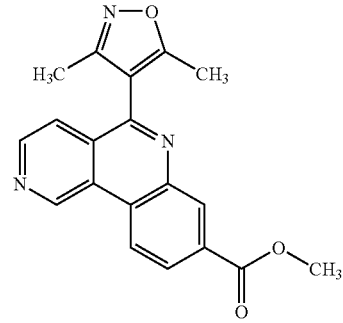 | 333.34 | 334 |
| 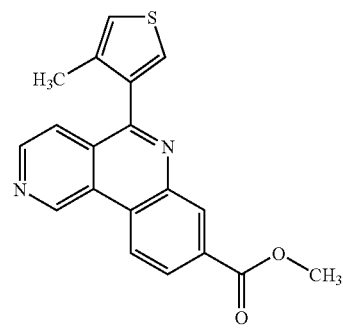 | 334.39 | 335 |
| 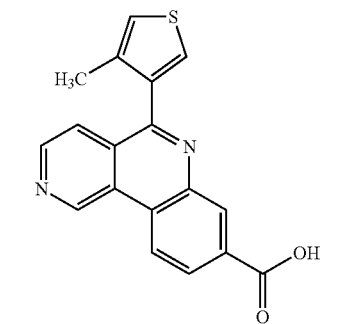 | 320.37 | 321 |
| 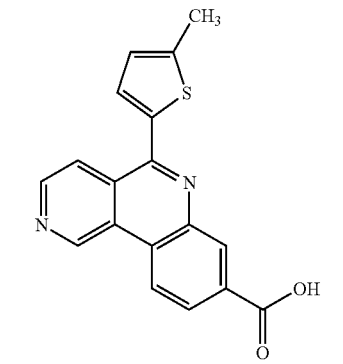 | 340.78 | 342 |

EXAMPLE 12

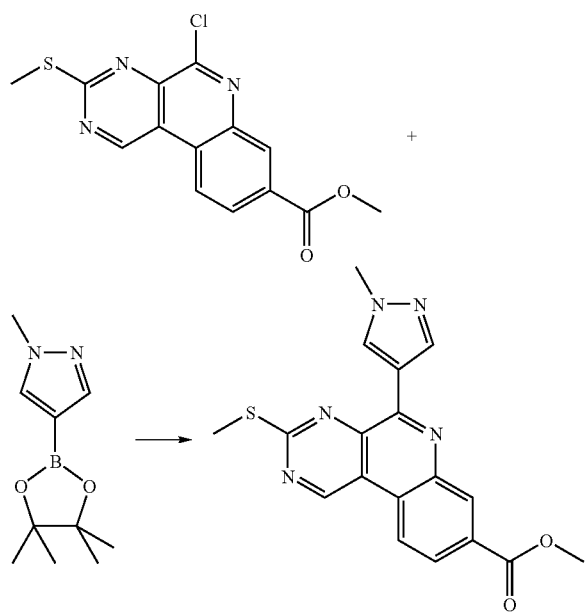

Methyl 5-(1-methyl-1H-pyrazol-4-yl)-3-(methylthio)pyrimido[4,5-c]quinoline-8-carboxylate was prepared using the same protocol as described in Example 4. LCMS (ES): m/z 366 [M+1]$^+$.

EXAMPLE 13

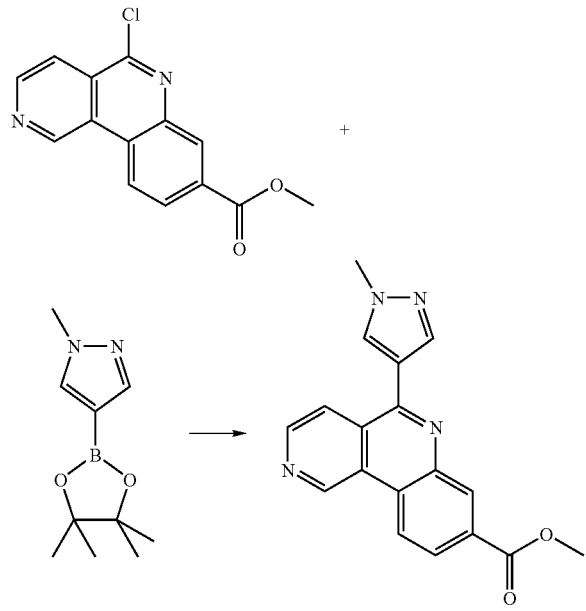

Methyl 5-(1-methyl-1H-pyrazol-4-yl)benzo[c][2,6]naphthyridine-8-carboxylate was prepared was prepared using the same protocol as described in Example 4. LCMS (ES): m/z 319 [M+1]$^+$.

EXAMPLE 14

Processes for Synthesizing Compounds of Formula (II)

Process 10

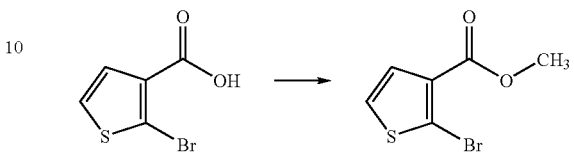

2-bromo-3-thiophene carboxylic acid (1.0 eq, 12.56 g, 60.66 mmol) was suspended in CH$_2$Cl$_2$ (200 ml). Oxalyl chloride (1.1 eq, 5.9 ml, 67.16 mmol) and 5 drops of DMF were added, inducing formation of gas. The mixture was stirred overnight at room temperature and the volatiles were removed in vacuo. The resulting solid was suspended in dry methanol (150 ml) and the mixture heated to ebullition. Evaporation of the solvents afforded methyl 2-bromo-3-thiophene carboxylate (13.16 g, 98% yield) as a crude brown oil. LCMS (ES): 99% pure, m/z not detected; $^1$H NMR (CDCl$_3$, 400 MHz) δ 3.88 (s, 3H), 7.23 (d, J=5.6, 1H), 7.56 (d, J=5.6, 1H) ppm.

Process 11

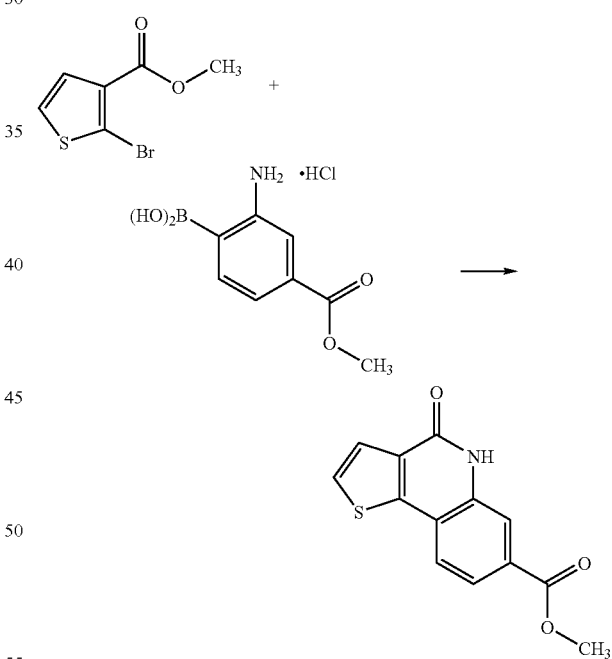

In a microwave vessel, methyl 2-bromo-3-thiophene carboxylate (1.0 eq, 260 mg, 1.18 mmol), 2-amino-4-(methoxycarbonyl)phenylboronic acid hydrochloride (1.1 eq, 300 mg, 1.30 mmol), sodium acetate (3.0 eq, 292 mg, 3.56 mmol) and PdCl$_2$(dppf) (0.05 eq, 31 mg, 0.059 mmol) were mixed together in anhydrous DMF (2 ml). The mixture was heated in a microwave oven at 120° C. for 10 nm. Water was added and the solid filtered and dried. The material was suspended in CH$_2$Cl$_2$, filtered and dried to afford methyl 4-oxo-4,5-dihydrothieno[3,2-c]quinoline-7-carboxylate as a yellow solid (152 mg, 50% yield). LCMS (ES): 95% pure, m/z 260

[M+1]⁺; ¹H NMR (CDCl₃, 400 MHz) δ 3.99 (s, 3H), 7.54 (d, J=5.2, 1H), 7.79 (d, J=4.8, 1H), 7.86 (d, J=8.4, 1H), 7.91 (dd, J=8.4, J=1.6, 1H), 8.03 (d, J=1.2, 1H) ppm.

Process 12

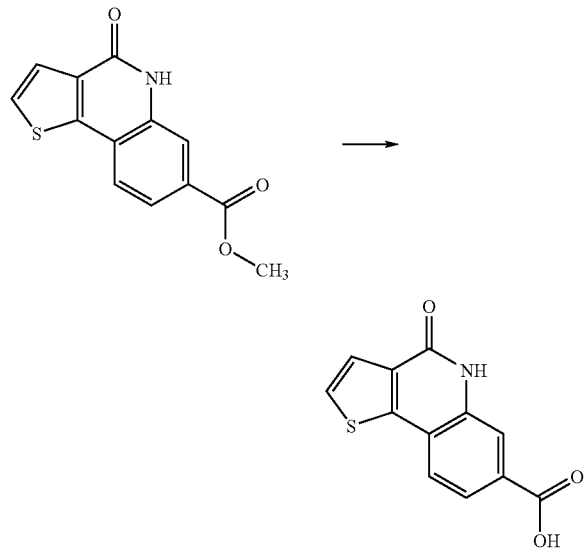

Methyl 4-oxo-4,5-dihydrothieno[3,2-c]quinoline-7-carboxylate (1.0 eq, 618 mg, 2.38 mmol) was suspended in 10 ml of a mixture of MeOH, THF, and water (1:1:1, v:v:v). LiOH (2.0 eq, 114 mg, 4.76 mmol) was added and the mixture was stirred at room temperature for 2 hours. An additional amount of LiOH (114 mg) was added and the mixture was stirred for an hour. LiOH (50 mg) was added and the mixture stirred for an additional 2 hours. Water was added and the solution filtered through a pad of celite. The pad of celite was thoroughly washed with aqueous 1 N NaOH. The solution was acidified with 6 N aqueous HCl to induce precipitation of the expected material. Filtration and drying afforded 4-oxo-4,5-dihydrothieno[3,2-c]quinoline-7-carboxylic acid as a yellow solid (562 mg, 96% yield). LCMS (ES): 95% pure, m/z 246 [M+1]⁺; ¹H NMR (DMSO-d₆, 400 MHz) δ 7.61 (d, J=5.2, 1H), 7.73 (dd, J=1.6, J=8.0, 1H), 7.88 (d, J=5.6, 1H), 7.92 (d, J=8.4, 1H), 8.02 (d, J=1.6, 1H), 11.92 (s, 1H), 13.21 (br. s, 1H) ppm.

Process 13

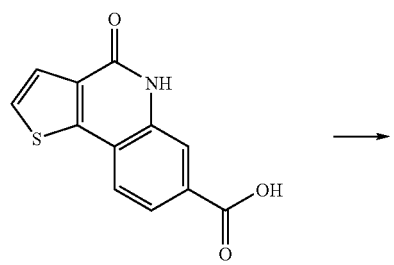

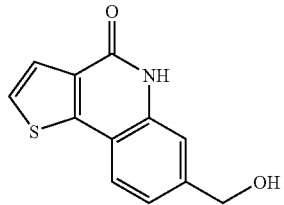

4-oxo-4,5-dihydrothieno[3,2-c]quinoline-7-carboxylic acid (1.0 eq, 38 mg, 0.155 mmol) was suspended in dioxane (1 ml). LiAlH₄ (7.0 eq, 40 mg, 1.05 mmol) was added and the mixture stirred at 100° C. for 45 nm. Water was added, then MeOH and CH₂Cl₂. The solid salts were filtered off and washed with MeOH and CH₂Cl₂. After evaporation of the volatiles in vacuo, the material was dissolved in a mixture of NMP, MeOH and water and was purified by preparative HPLC. Genevac evaporation afforded 7-(hydroxymethyl)thieno[3,2-c]quinolin-4(5H)-one as an off-white solid (12 mg, 34%). LCMS (ES): 95% pure, m/z 232 [M+1]⁺; ¹H NMR (DMSO-d₆, 400 MHz) δ 4.56 (s, 2H), 7.15 (d, J=7.6, 1H), 7.39 (br s, 1H), 7.55 (d, J=5.2, 1H), 7.73 (d, J=5.2, 1H), 7.76 (d, J=8.0, 1H), 11.73 (s, 1H) ppm.

Process 14

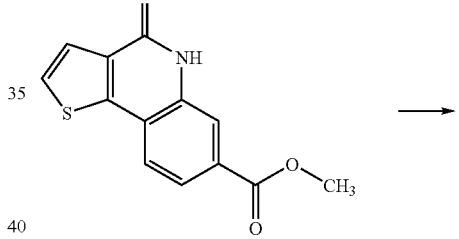

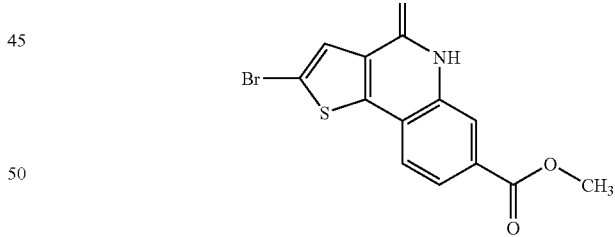

Methyl 4-oxo-4,5-dihydrothieno[3,2-c]quinoline-7-carboxylate (1.0 eq, 17 mg, 0.066 mmol) was suspended in a mixture of chloroform (0.3 ml) and acetic acid (0.1 ml). NBS was added (9.5 eq, 112 mg, 0.63 mmol) and the mixture stirred at 70° C. for 16 hours. Water and aqueous ammonia was added and the material was extracted with CH₂Cl₂ (2×). The combined extracts were dried over Na₂SO₄ and the solvent removed in vacuo to provide methyl 2-bromo-4-oxo-4,5-dihydrothieno[3,2-c]quinoline-7-carboxylate (17 mg, 76%). LCMS (ES): >85% pure, m/z 338 [M]⁺, 340 [M+2]⁺; ¹H NMR (CDCl₃/CD₃OD, δ: 1, 400 MHz) δ 3.99 (s, 3H), 7.30 (m, 1H), 7.69 (d, J=8.4, 1H), 7.45 (m, 1H), 7.88 (br d, J=8, 1H), 8.05 (br s, 1H) ppm.

Process 15

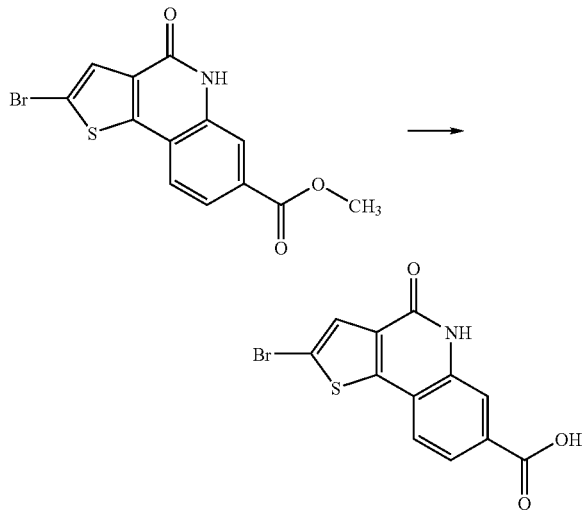

Methyl 2-bromo-4-oxo-4,5-dihydrothieno[3,2-c]quinoline-7-carboxylate (1.0 eq, 17 mg, 0.050 mmol) was suspended in a 1:1:1 mixture of MeOH/THF/water (0.6 ml). LiOH (39 mg) was added and the mixture stirred at room temperature for one hour. Water and 6N HCl was added and the resulting precipitate was filtered. The material was purified by preparative HPLC. Genevac evaporation provided 2-bromo-4-oxo-4,5-dihydrothieno[3,2-c]quinoline-7-carboxylic acid as a solid (2.1 mg, 13% yield). LCMS (ES): >95% pure, m/z 324 [M]$^+$, 326[M+2]$^+$; $^1$H NMR (DMSO-d$_6$, 400 MHz) δ 7.75 (s, 1H), 7.75 (dd, J=1.6, J=8.0, 1H), 7.90 (d, J=8.4, 1H), 8.03 (d, J=1.6, 1H), 12.06 (s, 1H) ppm.

Process 16

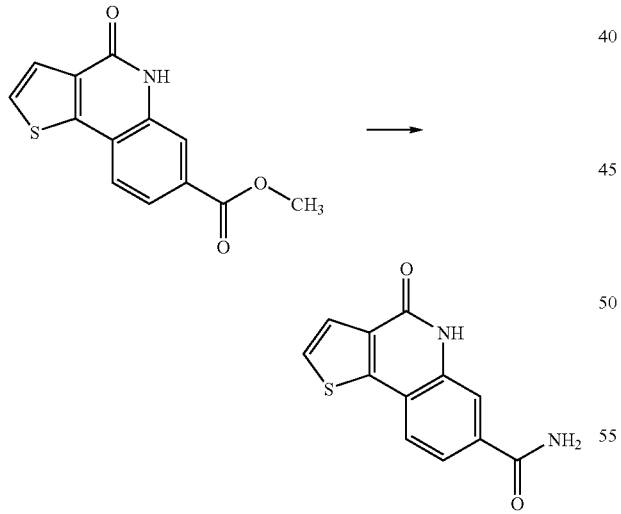

In a closed vessel, Methyl 4-oxo-4,5-dihydrothieno[3,2-c]quinoline-7-carboxylate (44 mg, 0.170 mmol) was suspended in concentrated aqueous ammonia (1 ml). The mixture was stirred at 100° C. overnight. Aqueous 1N NaOH was added and the mixture stirred at room temperature for 2 hours. The solid was filtered and dried to provide 4-oxo-4,5-dihydrothieno[3,2-c]quinoline-7-carboxamide as a brown solid (13 mg, 32% yield). LCMS (ES): 95% pure, m/z 245 [M+1]$^+$.

Process 17

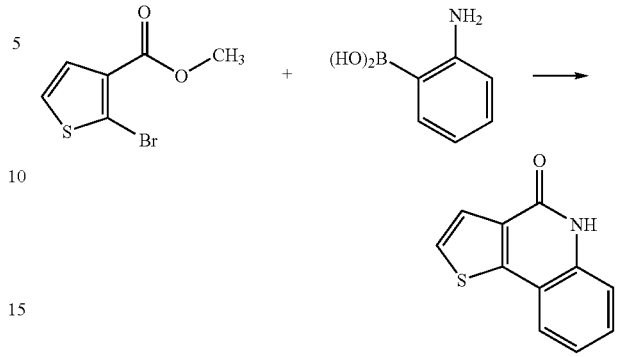

In a microwave vessel, methyl 2-bromo-3-thiophene carboxylate (1.0 eq, 64 mg, 0.29 mmol), 2-amino phenyl boronic acid (1.2 eq, 48 mg, 0.35 mmol), sodium acetate (3.0 eq, 71 mg, 0.86 mmol) and PdCl$_2$(dppf) (0.1 eq, 15 mg, 0.028 mmol) were mixed together in anhydrous DMF (0.2 ml). The mixture was heated in a microwave oven at 120° C. for 5 nm. The material was purified by preparative HPLC. Acetonitrile was evaporated, and the compound was extracted with CH$_2$Cl$_2$ (3×). The combined extracts were washed with water, dried over Na$_2$SO$_4$, and the solvents removed in vacuo. Recrystallization in EtOH provided thieno[3,2-c]quinolin-4(5H)-one as a tan crystalline solid (7 mg, 12% yield). LCMS (ES): 95% pure, m/z 202 [M+1]$^+$; $^1$H NMR (CDCl$_3$/CD$_3$OD, 9:1, 400 MHz) δ 7.28 (m, 1H), 7.33 (m, 1H), 7.43-7.50 (m, 2H), 7.74 (d, J=4.4, 1H), 7.82 (d, J=7.6, 1H) ppm

Process 18

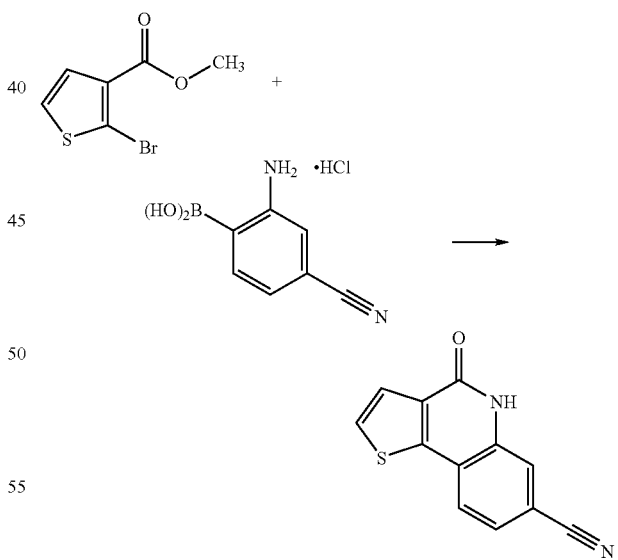

In a microwave vessel, methyl 2-bromo-3-thiophene carboxylate (1.0 eq, 250 mg, 1.13 mmol), 2-amino-3-cyanophenyl boronic acid HCl (1.1 eq, 250 mg, 1.24 mmol), sodium acetate (3.0 eq, 278 mg, 3.39 mmol) and PdCl$_2$(dppf) (0.007 eq, 4.3 mg, 0.0082 mmol) were mixed together in anhydrous DMF (2.5 ml). The mixture was heated in a microwave oven at 120° C. for 10 nm. Water was added and the material extracted with CH$_2$Cl$_2$. The organic extracts were washed with brine, dried over Na$_2$SO$_4$ and the solvents removed in vacuo. The resulting solid was sonicated in AcOEt, filtered and dried to afford 4-oxo-4,5-dihydrothieno[3,2-c]quinoline-7-carbonitrile as a beige solid (121 mg, 48% yield). LCMS (ES): 95% pure, m/z 227 [M+1]$^+$.

Process 19

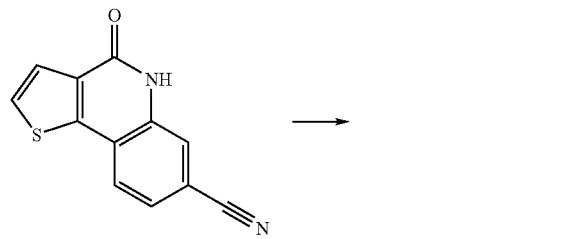

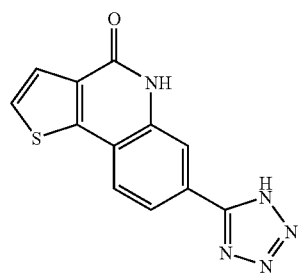

4-oxo-4,5-dihydrothieno[3,2-c]quinoline-7-carbonitrile (1.0 eq, 20 mg, 0.088 mmol) was dissolved in anhydrous DMF (0.15 ml). Sodium azide (4.0 eq, 23 mg, 0.354 mmol) and ammonium chloride (4.0 eq, 19 mg, 0.354 mmol) were added and the mixture stirred at 120° C. overnight. The reaction mixture was cooled down and water was added. Addition of aqueous 6 N HCl induced formation of a precipitate. After filtration and drying in vacuo, 7-(1H-tetrazol-5-yl)thieno[3,2-c]quinolin-4(5H)-one was isolated as a greenish solid (18 mg, 76% yield)). LCMS (ES): 95% pure, m/z 270 [M+1]$^+$, 242 [M+1-N$_2$]$^+$; $^1$H NMR (DMSO-d$_6$, 400 MHz) δ 7.64 (d, J=5.2, 1H), 7.86 (dd, J=1.6, J=8.4, 1H), 7.89 (d, J=5.2, 1H), 8.09 (d, J=8.0, 1H), 8.16 (d, J=1.6, 1H), 12.03 (s, 1H) ppm.

Process 20

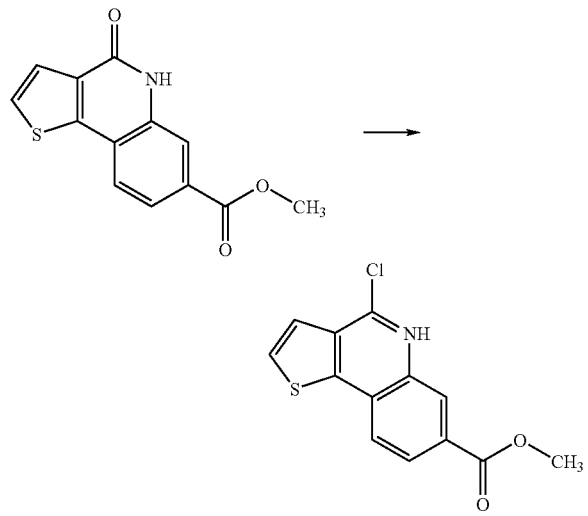

Methyl 4-oxo-4,5-dihydrothieno[3,2-c]quinoline-7-carboxylate (1.0 eq, 1.50 g, 5.79 mmol) was suspended in dry toluene (15 ml). POCl$_3$ (1.2 eq, 0.64 mmol, 6.99 mmol) and DIEA (0.8 eq, 0.81 mmol, 4.65 mmol) were added and the mixture vigorously stirred at 120° C. for 3 hours under nitrogen atmosphere. The mixture was hydrolyzed by addition of ice and water. The compound was extracted with CH$_2$Cl$_2$ (4×). The combined extracts were dried over Na$_2$SO$_4$ and the black solution filtered through a pad of celite. After evaporation of the volatiles in vacuo, the resulting solid was triturated in a mixture of AcOEt and hexanes. Filtration and drying provided methyl 4-chlorothieno[3,2-c]quinoline-7-carboxylate as a yellow fluffy solid (1.14 g, 71% yield). LCMS (ES): 95% pure, m/z 278 [M+1]$^+$, $^1$H NMR (CDCl$_3$, 400 MHz) δ 4.01 (s, 3H), 7.72 (d, J=4.8, 1H), 7.74 (d, J=5.2, 1H), 8.14 (d, J=8.4, 1H), 8.25 (d, J=8.4, 1H), 8.85 (d, J=1.6, 1H) ppm.

Process 21

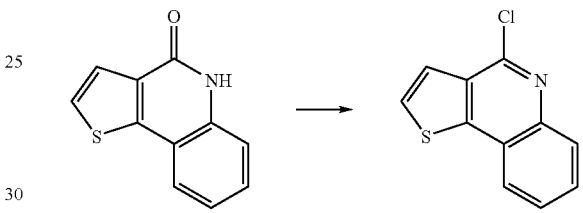

4-chlorothieno[3,2-c]quinoline was prepared according to the procedure used in process 16, starting from thieno[3,2-c]quinolin-4(5H)-one. 4-chlorothieno[3,2-c]quinoline was isolated as a solid (71 mg, 93% yield). LCMS (ES): 95% pure, m/z 220 [M+1]$^+$, 223 [M+3]$^+$.

Process 22

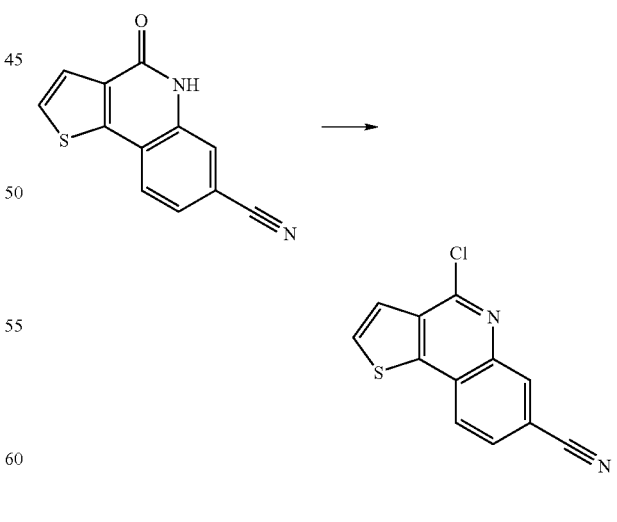

4-chlorothieno[3,2-c]quinoline-7-carbonitrile was prepared according to the procedure used in process 16. 4-chlorothieno[3,2-c]quinoline-7-carbonitrile was isolated as a yellow fluffy solid (833 mg, 77% yield). LCMS (ES): 95% pure, m/z 245 [M+1]$^+$, 247 [M+3]$^+$.

Process 23

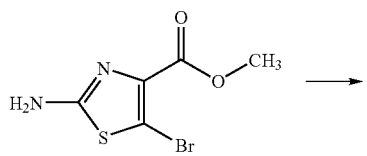

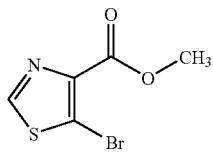

Methyl 2-amino-4-bromothiazole-4-carboxylate (1.0 eq, 100 mg, 0.42 mmol) was dissolved in anhydrous DMF (0.8 ml). The mixture was heated to 80° C. under nitrogen atmosphere. To the hot mixture, a solution of tert-Butyl nitrite (1.2 eq, 60 ul, 0.50 mmol) in DMF (0.8 ml) was added dropwise. After a few minutes, absence of gas evolution indicated completion of the reaction. The mixture was cooled down and poured onto a prepacked silica gel column. Flash chromatography using hexanes, then AcOEt/hexanes (2:8), provided methyl 5-bromothiazole-4-carboxylate as a yellow solid (49 mg, 53% yield). LCMS (ES): 95% pure, m/z 222 [M]$^+$, 224 [M+2]$^+$.

Process 24

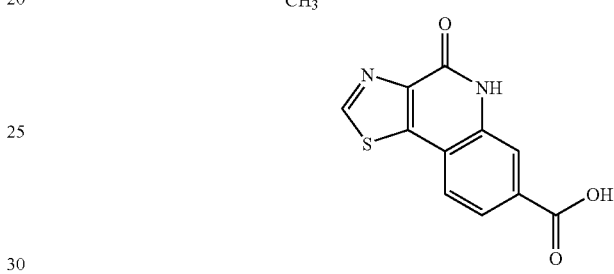

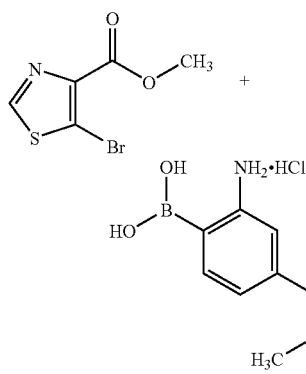

In a microwave vessel, methyl 5-bromothiazole-4-carboxylate (1.0 eq, 97 mg, 0.44 mmol), 2-amino-3-methoxycarbonyl phenyl boronic acid HCl (1.1 eq, 111 mg, 0.48 mmol), sodium acetate (3.0 eq, 107 mg, 1.31 mmol) and PdCl$_2$(dppf) (0.05 eq, 11 mg, 0.022 mmol) were mixed together in anhydrous DMF (1 ml). The mixture was heated in a microwave oven at 120° C. for 10 nm. Water was added and the material extracted with CH$_2$Cl$_2$. The combined extracts were washed with brine, dried over Na$_2$SO$_4$ and the solvents removed by evaporation. The material was dissolved in a mixture of CH$_2$Cl$_2$ and MeOH and the solution filtered through a pad of celite. Evaporation of the volatiles afforded crude methyl 4-oxo-4,5-dihydrothiazolo[4,5-c]quinoline-7-carboxylate as a black solid (44 mg, 39% yield). A small part of the compound was subjected to preparative HPLC for analytical purpose. LCMS (ES): 95% pure, m/z 261 [M+1]$^+$.

Process 25

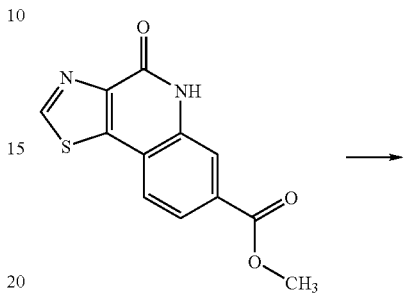

Methyl 4-oxo-4,5-dihydrothiazolo[4,5-c]quinoline-7-carboxylate (35 mg, 0.12 mmol) and LiOH (60 mg, 0.83 mmol) were stirred in a (1:1:1, v:v:v) mixture of THF, MeOH and water (0.6 ml) for 2 hours. 6 N aqueous NaOH was added and the solution filtered through celite. The solution was acidified and the resulting solid filtered. Preparative HPLC purification and genevac evaporation provided 4-oxo-4,5-dihydrothiazolo[4,5-c]quinoline-7-carboxylic acid as a white solid (0.8 mg). LCMS (ES): 95% pure, m/z 247 [M+1]$^+$.

Process 26

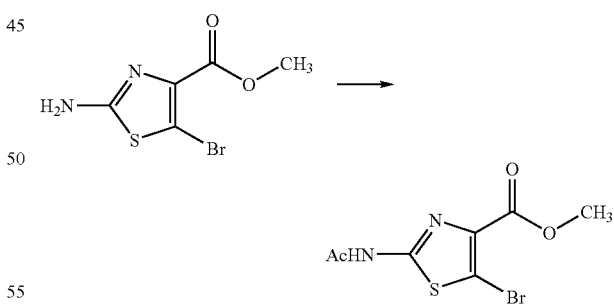

Methyl 2-amino-4-bromothiazole-4-carboxylate (1.0 eq, 2.0 g, 8.44 mmol) was dissolved in CH$_2$Cl$_2$ (4 ml). Acetic anhydride (1.5 eq, 1.2 ml, 12.66 mmol) and triethylamine (1.1 eq, 1.3 ml, 9.28 mmol) were added and the mixture stirred at 100° C. for one hour. The resulting solid was filtered, triturated in AcOEt and then filtered again. After drying, methyl 2-acetamido-5-bromothiazole-4-carboxylate was isolated as a beige solid (1.81 g, 77% yield). LCMS (ES): 95% pure, m/z 280 [M+1]$^+$. $^1$H NMR (CDCl$_3$, 400 MHz) δ 2.25 (s, 3H), 3.95 (s, 3H) ppm.

Process 27

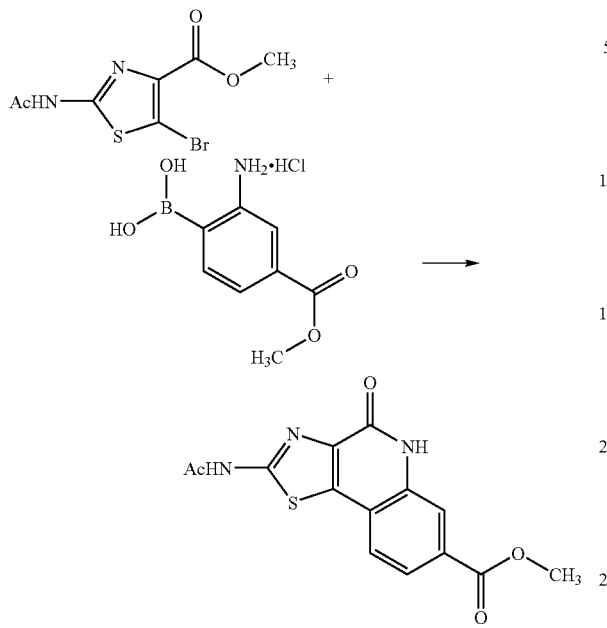

Methyl 2-acetamido-4-oxo-4,5-dihydrothiazolo[4,5-c]quinoline-7-carboxylate was prepared according to the procedure used in process 2, starting from methyl 2-acetamido-5-bromothiazole-4-carboxylate. Methyl 2-acetamido-4-oxo-4,5-dihydrothiazolo[4,5-c]quinoline-7-carboxylate was isolated as a black solid (106 mg, 37% yield). LCMS (ES): 95% pure, m/z 318 [M+1]$^+$.

Process 28

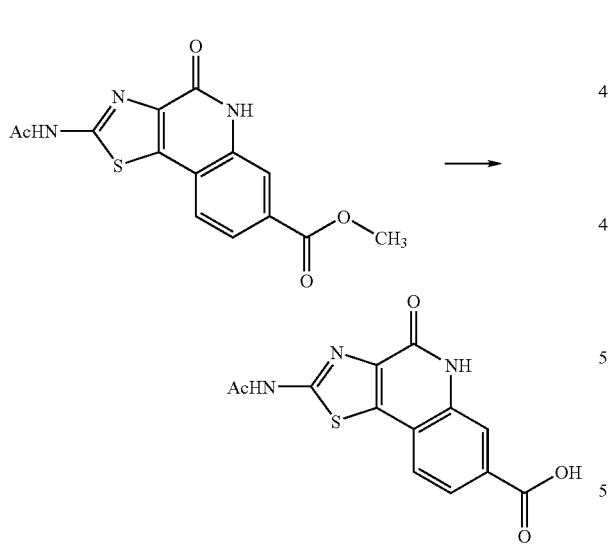

2-acetamido-4-oxo-4,5-dihydrothiazolo[4,5-c]quinoline-7-carboxylic acid was prepared according to the procedure in process 3, starting from. Methyl 2-acetamido-4-oxo-4,5-dihydrothiazolo[4,5-c]quinoline-7-carboxylate. -acetamido-4-oxo-4,5-dihydrothiazolo[4,5-c]quinoline-7-carboxylic acid was isolated as a black solid (14 mg, 44% yield). LCMS (ES): 95% pure, m/z 304 [M+1]$^+$, $^1$H NMR (DMSO-d$_6$, 400 MHz) δ 2.22 (s, 3H), 7.74 (dd, J=1.2, J=8.0, 1H), 7.89 (d, J=8.4, 1H), 8.03 (d, J=1.6, 1H), 12.07 (s, 1H), 12.80 (s, 1H) ppm.

Process 29

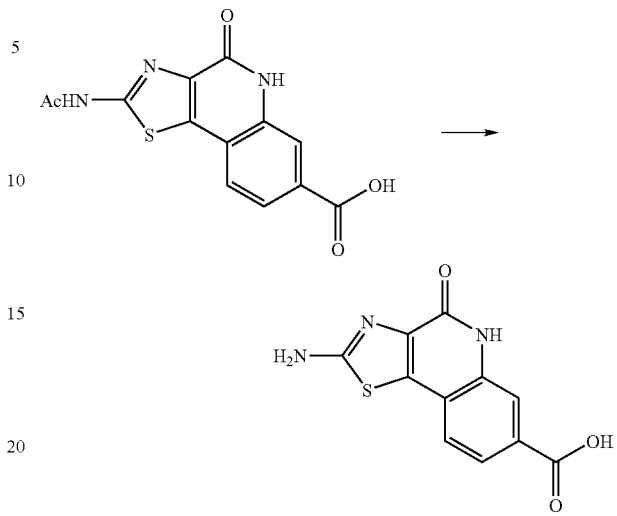

2-acetamido-4-oxo-4,5-dihydrothiazolo[4,5-c]quinoline-7-carboxylic acid (102 mg, 0.34 mmol) was stirred at 120° C. in aqueous 6N HCl overnight. Water was added and the compound was filtered and dried to provide 2-amino-4-oxo-4,5-dihydrothiazolo[4,5-c]quinoline-7-carboxylic acid as a black solid (76 mg, 86% yield). LCMS (ES): 95% pure, m/z 262 [M+1]$^+$, $^1$H NMR (DMSO-d$_6$, 400 MHz) δ 7.60 (d, J=8.4, 1H), 7.70 (dd, J=1.2, J=8.0, 1H), 7.99 (d, J=1.2, 1H), 11.94 (s, 1H) ppm.

Process 30

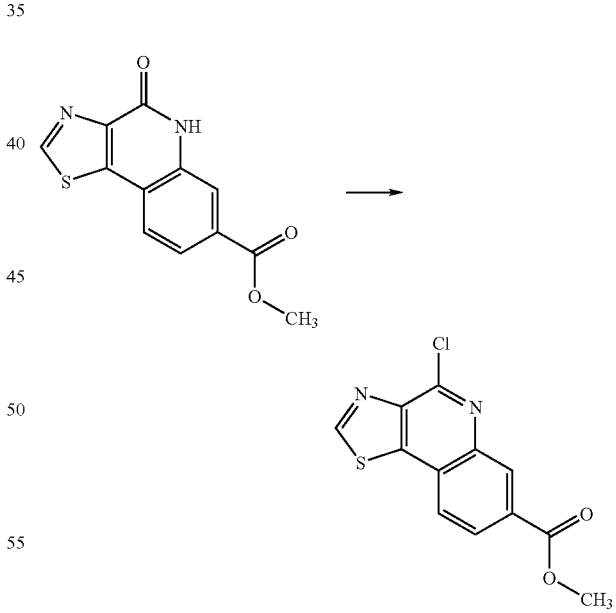

Methyl 4-oxo-4,5-dihydrothiazolo[4,5-c]quinoline-7-carboxylate (1.0 eq, 0.62 g, 2.38 mmol) was suspended in toluene. DIEA (1.5 eq, 122 ul, 3.57 mmol) and POCl$_3$ (2.3 eq, 507 ul, 5.47 mmol) were added and the mixture vigorously stirred at 120° C. for 1 hour. Water, ice and CH$_2$Cl$_2$ were added and the resulting emulsion filtered through celite. The organic phase was decanted and the aqueous phase further extracted with CH$_2$Cl$_2$. The combined organic extracts were dried over Na$_2$SO$_4$ and the solvent removed in vacuo to afford methyl 4-chlorothiazolo[4,5-c]quinoline-7-carboxylate (0.31 g, 47% yield). LCMS (ES): >90% pure, m/z 279[M+1]$^+$.

Conversion of Intermediates to Compounds of Formula (II)

Compounds of Formula (II) are prepared by routes analogous to those described herein for preparation of compounds of Formula (I). For example, the halogenated products prepared in processes 20, 21, 22, and 30, may be converted to compounds of Formula (II) under conditions substantially as described in Example 4, or under conditions known to those of skill in the art.

EXAMPLE 15

Modulation of CK2 Activity in Cell-free In vitro Assays

Modulatory activity of compounds described herein is assessed in vitro in cell-free CK2 assays. These assays are described hereafter.

CK2 Assay

Test compounds in aqueous solution are added at a volume of 10 microliters, to a reaction mixture comprising 10 microliters Assay Dilution Buffer (ADB; 20mM MOPS, pH 7.2, 25 mM beta-glycerolphosphate, 5 mM EGTA, 1 mM sodium orthovanadate and 1 mM dithiothreitol), 10 microliters of substrate peptide (RRRDDDSDDD (SEQ ID NO:4), dissolved in ADB at a concentration of 1 mM), 10 microliters of recombinant human CK2 (25 ng dissolved in ADB; Upstate). Reactions are initiated by the addition of 10 microliters of ATP Solution (90% 75 mM MgCl$_2$, 75 micromolar ATP dissolved in ADB; 10% [γ-$^{33}$P]ATP (stock 1 mCi/100 μl; 3000 Ci/mmol (Perkin Elmer) and maintained for 10 minutes at 30 degrees C. The reactions are quenched with 100 microliters of 0.75% phosphoric acid, then transferred to and filtered through a phosphocellulose filter plate (Millipore). After washing each well 5 times with 0.75% phosphoric acid, the plate is dried under vacuum for 5 min and, following the addition of 15 ul of scintillation fluid to each well, the residual radioactivity is measured using a Wallac luminescence counter.

EXAMPLE 16

Cell Proliferation Modulatory Activity

A representative cell-proliferation assay protocol using Alamar Blue dye (stored at 4° C., use 20 ul per well) is described hereafter.

96-Well Plate Setup and Compound Treatment
a. Split and trypsinize cells.
b. Count cells using hemocytometer.
c. Plate 4,000-5,000 cells per well in 100 μl of medium and seed into a 96-well plate according to the following plate layout. Add cell culture medium only to wells B10 to B12. Wells B1 to B9 have cells but no compound added.

|   | 1 | 2 | 3 | 4 | 5 | 6 | 7 | 8 | 9 | 10 | 11 | 12 |
|---|---|---|---|---|---|---|---|---|---|----|----|----|
| A |   |   |   | EMPTY |   |   |   |   |   |    |    |    |
| B |   |   | NO COMPOUND ADDED |   |   |   |   | Medium Only |   |    |    |    |
| C | 10 nM |   |   | 100 nM |   |   | 1 uM |   |   | 10 uM |   | Control |
| D | 10 nM |   |   | 100 nM |   |   | 1 uM |   |   | 10 uM |   | Comp 1 |
| E | 10 nM |   |   | 100 nM |   |   | 1 uM |   |   | 10 uM |   | Comp 2 |
| F | 10 nM |   |   | 100 nM |   |   | 1 uM |   |   | 10 uM |   | Comp 3 |
| G | 10 nM |   |   | 100 nM |   |   | 1 uM |   |   | 10 uM |   | Comp 4 |
| H |   |   |   |   |   | EMPTY |   |   |   |    |    |    | d. Add 100 μl of 2× drug dilution to each well in a concentration shown in the plate layout above. At the same time, add 100 μl of media into the control wells (wells B10 to B12). Total volume is 200 μl/well.
e. Incubate four (4) days at 37° C., 5% CO2 in a humidified incubator.
f. Add 20 μl Alamar Blue reagent to each well.
g. Incubate for four (4) hours at 37° C., 5% CO2 in a humidified incubator.
h. Record fluorescence at an excitation wavelength of 544 nm and emission wavelength of 590 nm using a microplate reader.

In the assays, cells are cultured with a test compound for approximately four days, the dye is then added to the cells and fluorescence of non-reduced dye is detected after approximately four hours. Different types of cells can be utilized in the assays (e.g., HCT-116 human colorectal carcinoma cells, PC-3 human prostatic cancer cells and MiaPaca human pancreatic carcinoma cells).

EXAMPLE 17

Modulation of Endogenous CK2 Activity

The human leukemia Jurkat T-cell line is maintained in RPMI 1640 (Cambrex) supplemented with 10% fetal calf serum and 50 ng/ml Geutamycin. Before treatment cells are washed, resuspended at a density of about 10$^6$ cells/milliliter in medium containing 1% fetal calf serum and incubated in the presence of indicated mounts of drug for two hours. Cells are recovered by centrifugation, lysed using a hypotonic buffer (20 mM Tris/HCl pH 7.4; 2 mM EDTA; 5 mM EGTA; 10 mM mercaptoethanol; 10 mM NaF; 1 uM Okadaic acid; 10% v/v glycerol; 0.05% NP-40; 1% Protease Inhibitor Cocktail) and protein from the cleared lysate is diluted to 1 microgram per microliter in Assay Dilution Buffer (ADB; 20 mM MOPS, pH 7.2,mM β-gycerolphosphate, 5 mM EGTA, 1 mM sodium orthovanadate and 1 mMdithiothreitol). To 20 microliters of diluted protein is added 10 microliters of substrate peptide (RRRDDDSDDD (SEQ ID NO:4), dissolved in ADB at a concentration of 1 mM) and 10 microliters of PKA Inhibitor cocktail (Upstate). Reactions are initiated by the addition of 10 microliters of ATP Solution (90% 75 mM MgCl$_2$, 100 uM ATP dissolved in ADB; 10% [gamma-$^{33}$P]ATP (stock 1 mCi/100 microliters; 3000Ci/mmol (Perkin Elmer)) and maintained for 15 min at 32 degrees C. The reactions are quenched with 100 microliters of 0.75% phosphoric acid, then transferred to and filtered through a phosphocellulose filter plate (Millipore). After washing each well 5 times with 0.75% phosphoric acid, the residual radioactivity is measured using a Wallac luminescence counter.

EXAMPLE 18

Evaluation of Pharmacokinetic Properties

The pharmacokinetics properties of drugs are investigated in ICR mice following an intravenous (IV) bolus and oral (PO) doses of drug at 5 mg/kg and 25 mg/kg respectively.

Blood samples are collected at predetermined times and the plasma separated. Plasma is separated from the blood samples collected at 5, 15 and 30 minutes and 1, 2, 4, 8 and 24 hours post-dose.

Drug levels are quantified by the LC/MS/MS method described below. Noncompartmental pharmacokinetic analysis is applied for intravenous administration. A linear trapezoidal rule is used to compute AUC(0-24). The terminal $t_{1/2}$ and $C_0$ are calculated using the last three and the first three data points, respectively Bioanalysis is performed using a Quattro Micro LC/MS/MS instrument in the MRM detection mode, with an internal standard (IS). Briefly, 15 μL plasma samples are prepared for analysis using protein precipitation with 120 μL of acetonitrile. The supernatants are transferred into a 96 well plate and subjected to LC-MS/MS analysis using a Phenomenex Polar-RP HPLC column. The mobile phases are 10 mM $NH_4HCO_3$ in water (Solution-A) and 10 mM $NH_4HCO_3$ in methanol (Solution-B). The column is initially equilibrated with 25% Solution-B and followed with 100% Solution B over 5 minutes. The method has a dynamic range from 1 to 10,000 ng/mL. Quantitation of the analytes is performed in the batch mode with two bracketing calibration curves according to the bioanalytical sample list.

EXAMPLE 19

Modulation of non-CK2 Protein Kinase Activity

Compounds described herein are profiled for in vitro modulatory activity against protein kinases other than CK2. The in vitro analysis is conducted using known protocols (e.g., assay protocols described at world-wide web address upstate.com/img/pdf/KP_Assay Protocol_Booklet_v3.pdf). Compounds described herein are screened in the assays and prioritized based upon modulatory activity against protein kinases other than CK2 and specificity for CK2.

EXAMPLE 20

Modulation of Protein Kinase Activity in Cell-Free In Vitro Assay

In a PIM-1 assay, test compounds in aqueous solution are added at a volume of 5 μl, to a reaction mixture comprising 5 μl of 5× Reaction buffer (40 mM MOPS, pH 7.0, 1 mM EDTA), 2.5 μl of recombinant human PIM-1 solution (10 ng), 2.5 μl of substrate peptide(KKRNRTLTK) (SEQ ID NO:5) and 10 μl of ATP solution—98% (75 mM MgCl2 37.5 uM ATP) 2% ([γ-33P]ATP: 3000Ci/mmol—Perkin Elmer). The reactions are incubated for 10 min at 30° C., quenched with 100μl of 0.75% Phosphoric acid, then transferred to and filtered through a Phosphocellulose filter plate (Millipore). After washing each well 5 times with 0.75%Phosphoric acid, Scintillation fluid (15 μl) is added to each well. The residual radioactivity is measured using a luminescence counter.

Test compounds are tested further for activity against other protein kinases. Selected kinase inhibition $IC_{50}$ data are determined using standardized radiometric kinase assays for each individual kinase, which entail filter binding of $^{33}P$ labeled substrate proteins by the kinase of interest. Each $IC_{50}$ value is determined over a range of 10 drug concentrations. Representative reaction conditions are available from the World Wide Web URL upstate.com/discovery/services/ic50_profiler.q.

EXAMPLE 21

Biological Activity

Biological activity data for representative compounds of the invention against CK2 and in a variety of cell lines is provided in Table 2 below.

TABLE 2

| | Representative compounds and data | | | | | | | | | |
|---|---|---|---|---|---|---|---|---|---|---|
| Structure | CK2: % inh 500 nM | CK2: $IC_{50}$ (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
| 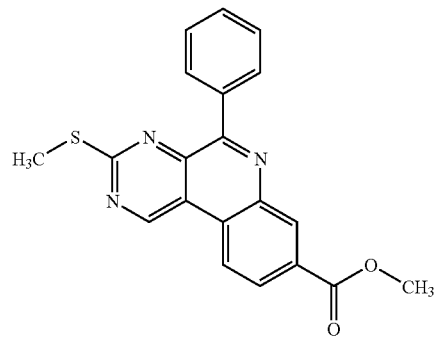 | −26 | 2.0 | | | | | | | | | |

TABLE 2-continued

Representative compounds and data

| Structure | CK2: % inh 500 nM | CK2: IC$_{50}$ (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| (structure: 6-phenyl-benzo[c][2,7]naphthyridine methyl ester) | −34 | 2.9 | >10 | >10 | | | | | | | |
| (structure: 6-(1-methylpyrazol-4-yl)-benzo[c][2,7]naphthyridine methyl ester) | −49 | 2.5 | >10 | >10 | | | | | | | |
| (structure: 6-phenyl-benzo[c][2,7]naphthyridine carboxylic acid) | 97 | 0.013 | >10 | >10 | 8.1 | >10 | >10 | >10 | | | |
| (structure: 6-(1-methylpyrazol-4-yl)-benzo[c][2,7]naphthyridine carboxylic acid) | 98 | 0.004 | >10 | >10 | >10 | >10 | >10 | >10 | | | |

TABLE 2-continued

Representative compounds and data

| Structure | CK2: % inh 500 nM | CK2: IC$_{50}$ (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| [phenyl-benzo[c][2,7]naphthyridine-CONH$_2$] | 27 | | >10 | >10 | 1.4 | | | | | | |
| [phenyl-benzo[c][2,7]naphthyridine-CONH-propyl] | −26 | | >10 | >10 | >10 | | | | | | |
| [phenyl-benzo[c][2,7]naphthyridine-CONH-cyclopropyl] | −9 | | >10 | >10 | >10 | | | | | | |
| [phenyl-benzo[c][2,7]naphthyridine-CON(CH$_3$)$_2$] | 0 | | >10 | >10 | >10 | | | | | | |

TABLE 2-continued

Representative compounds and data

| Structure | CK2: % inh 500 nM | CK2: IC$_{50}$ (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| (structure with pyrazole, fused tricyclic, CONH$_2$) | 7 | | >10 | >10 | 2.9 | | | | | | |
| (structure with N-propyl amide) | −21 | | >10 | >10 | >10 | | | | | | |
| (structure with N-cyclopropyl amide) | −15 | | | 1.0 | 2.7 | | | | | | |
| (structure with N,N-dimethyl amide) | −13 | | >10 | >10 | >10 | | | | | | |

TABLE 2-continued
Representative compounds and data
| Structure | CK2: % inh 500 nM | CK2: IC$_{50}$ (uM) | HCT- 116 (uM) | K562 (uM) | MV- 4-11 (uM) | Mia- PaCa (uM) | Bx- PC3 (uM) | MDA- MB231 (uM) | PC3 (uM) | Pan C1 (uM) | Jurkat (uM) |
|---|---|---|---|---|---|---|---|---|---|---|---|
| 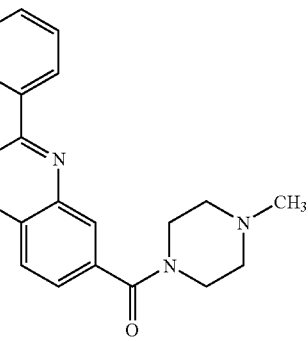 | 57 | | >10 | >10 | >10 | | | | | | |
| 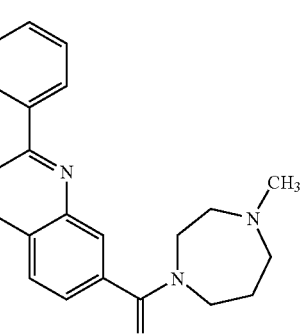 | −15 | | >10 | >10 | >10 | | | | | | |
| 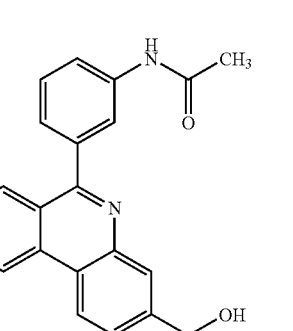 | 93 | 0.042 | >10 | >10 | >10 | >10 | >10 | >10 | | | |
| 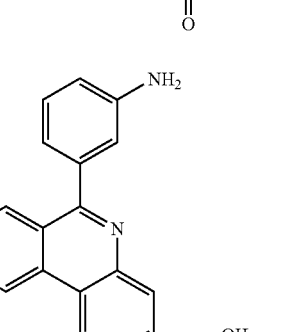 | 97 | 0.027 | >10 | | >10 | >10 | >10 | >10 | | | |

TABLE 2-continued
Representative compounds and data
| Structure | CK2: % inh 500 nM | CK2: IC$_{50}$ (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| 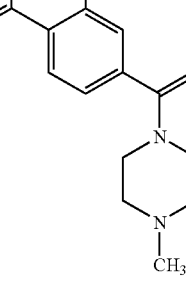 | 19 | >10 | >10 | >10 | >10 |  |  |  | >10 |  |  |
| 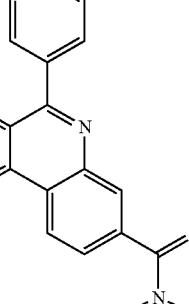 | −21 | >10 |  |  |  |  |  |  |  |  |  |
| 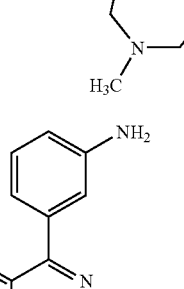 | −24 | >10 |  |  |  |  |  |  |  |  |  |

TABLE 2-continued

Representative compounds and data

| Structure | CK2: % inh 500 nM | CK2: IC$_{50}$ (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| 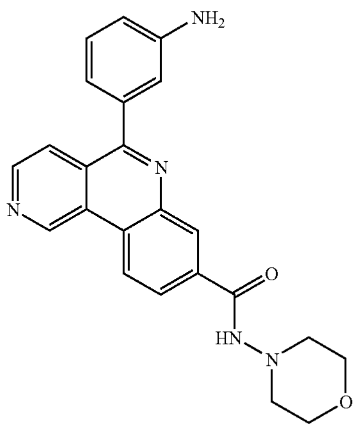 | −28 | >10 | | | | | | | | | |
| 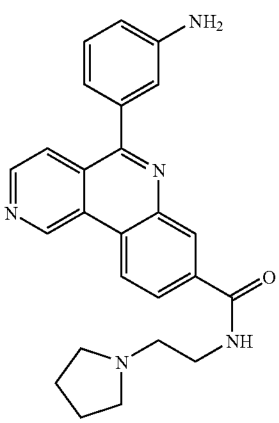 | 56 | >10 | | | | | | | | | |
| 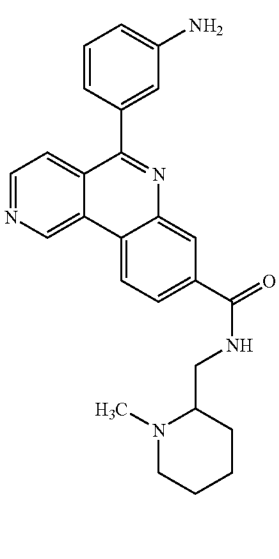 | 9 | >10 | >10 | >10 | >10 | | >10 | | | | |

TABLE 2-continued

Representative compounds and data

| Structure | CK2: % inh 500 nM | CK2: IC$_{50}$ (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| *(structure with acetamido-phenyl, pyrido-isoquinoline core, and 4-methylpiperazine carbonyl)* | 6 | >10 | | | | | | | | | |
| *(structure with acetamido-phenyl, pyrido-isoquinoline core, and 4-methyl-1,4-diazepane carbonyl)* | 30 | >10 | | | | | | | | | |

TABLE 2-continued

Representative compounds and data

| Structure | CK2: % inh 500 nM | CK2: IC$_{50}$ (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| (structure) | −6 | >10 | | | | | | | | | |
| (structure) | 19 | >10 | | | | | | | | | |
| (structure) | 89 | 0.144 | >10 | | | | | | | | |

TABLE 2-continued

Representative compounds and data

| Structure | CK2: % inh 500 nM | CK2: IC$_{50}$ (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| 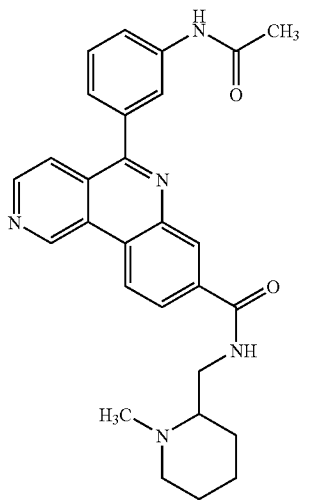 | 40 | >10 | | | | | | | | | |
| 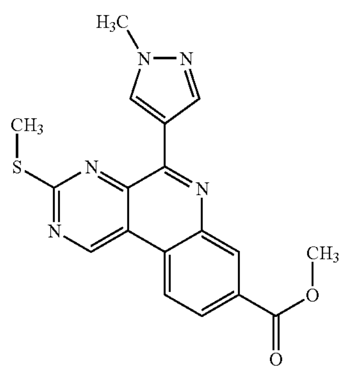 | 68 | >10 | | | >62.5 | >62.5 | >62.5 | | >62.5 | | 47.6 |
| 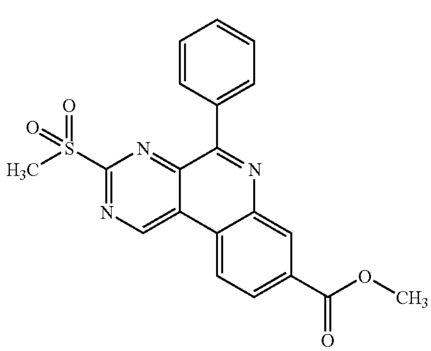 | −18 | 2.7 | | | 5.5 | 10.6 | 6.4 | | 9.8 | | 0.7 |

TABLE 2-continued

Representative compounds and data

| Structure | CK2: % inh 500 nM | CK2: IC$_{50}$ (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| (cyclopropylamino pyrimido-quinoline with phenyl and methyl ester) | −27 | | 2.6 | | | 3.2 | 1.9 | 3.4 | | 8.7 | 1.1 |
| (cyclopropylamino pyrimido-quinoline with phenyl and carboxylic acid) | 99 | 0.093 | 2.9 | | | 3.7 | 4.5 | 11.1 | | 15.9 | 1.5 |
| (cyclopropylamino pyrimido-quinoline with phenyl and carboxamide) | 45 | | 1.1 | | | 5.2 | 1.1 | 35.7 | | 25.9 | 0.5 |
| (cyclopropylamino pyrimido-quinoline with phenyl and N-cyclopropyl carboxamide) | −4 | | 0.8 | | | 58.4 | 1.2 | >62.5 | | 30.2 | 0.6 |

TABLE 2-continued
Representative compounds and data
| Structure | CK2: % inh 500 nM | CK2: IC$_{50}$ (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| 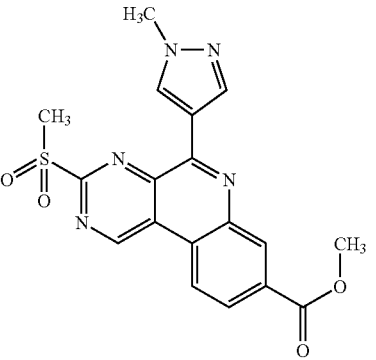 | 11 | | 0.9 | | | | | | | | |
| 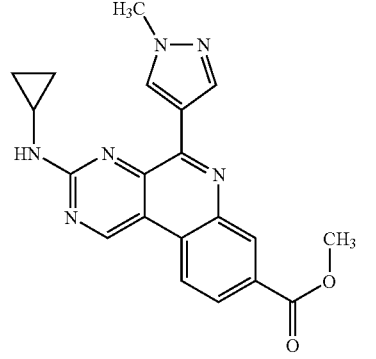 | 10 | | >10 | | | 0.6 | >30 | 17.2 | | 1.4 | >30 |
| 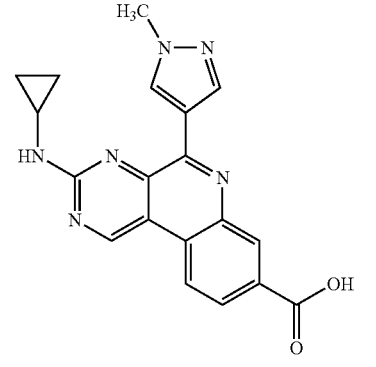 | 101 | 0.004 | >10 | 0.6 | 0.6 | 0.9 | 13.6 | >30 | | >30 | 3.6 |
| 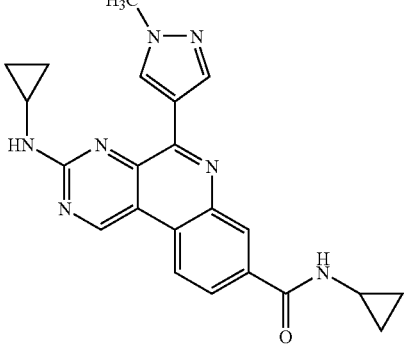 | 0 | | 4.3 | | 2.8 | 5.9 | >30 | | | >30 | 1.6 |

TABLE 2-continued
Representative compounds and data
| Structure | CK2: % inh 500 nM | CK2: IC50 (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| 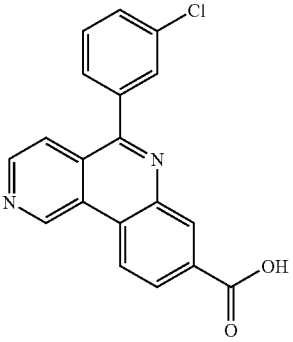 | 95 | 0.03 | >10 | 0.9 | >10 | >10 | >10 | >10 | >10 | | |
| 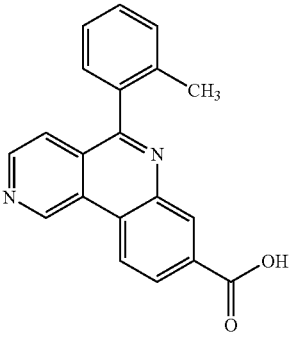 | 76 | | >10 | >10 | | >10 | | | >10 | | |
| 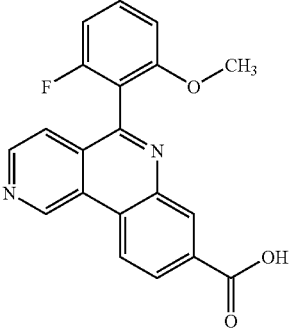 | 68 | | >10 | >10 | | >10 | | | >10 | | |
| 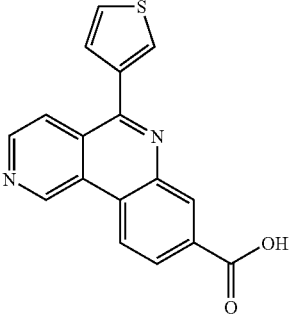 | 98 | 0.004 | >30 | 0.2 | 13.3 | >10 | >10 | >10 | >10 | | |

TABLE 2-continued

Representative compounds and data

| Structure | CK2: % inh 500 nM | CK2: IC$_{50}$ (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| (structure) | 98 | 0.007 | >10 | >10 | >10 | >10 | >10 | >10 | >10 | | |
| (structure) | −5 | | >10 | >10 | >10 | | | >10 | | | |
| (structure) | −15 | | >10 | >10 | >10 | | | >10 | | | |
| (structure) | −17 | | >10 | >10 | >10 | | | >10 | | | |

TABLE 2-continued

Representative compounds and data

| Structure | CK2: % inh 500 nM | CK2: IC50 (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| (2-F phenyl compound) | 97 | 0.106 | >10 | >10 | >10 | >10 | | | 4.1 | | |
| (3-F phenyl compound) | 98 | 0.029 | >10 | >10 | 1.4 | >10 | | 0.2 | >10 | | |
| (4-F phenyl compound) | 98 | 0.033 | >10 | 1.0 | 7.0 | >30 | | >10 | | | |
| (2-OCF3 phenyl compound) | 23 | | >10 | | >10 | | | >10 | | | |

TABLE 2-continued
Representative compounds and data
| Structure | CK2: % inh 500 nM | CK2: IC$_{50}$ (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| 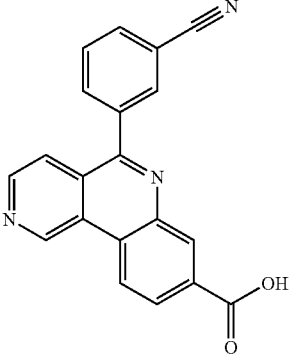 | 98 | 0.045 | >10 | | | >10 | | | >10 | | |
| 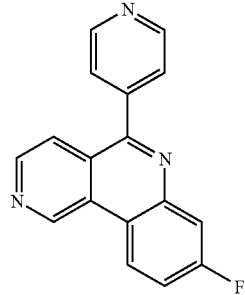 | –37 | | | | | | | | | | |
| 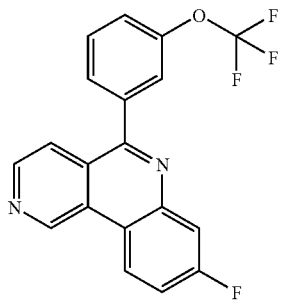 | –35 | | | | | | | | | | |
| 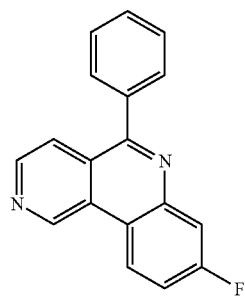 | –51 | | | | | | | | | | |

TABLE 2-continued

Representative compounds and data

| Structure | CK2: % inh 500 nM | CK2: IC$_{50}$ (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| 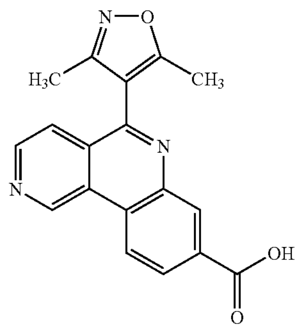 | 52 | | | | | | | | | | |
| 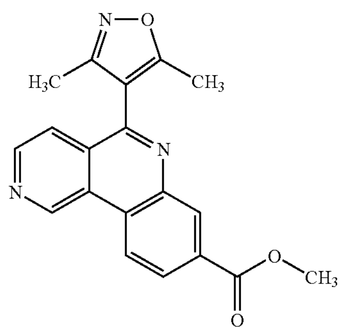 | −5 | | | | | | | | | | |
| 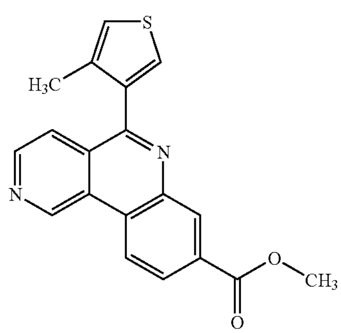 | 4 | | | | | | | | | | |
| 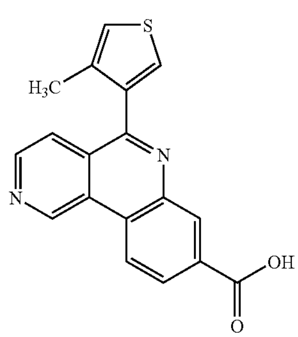 | 87 | | | | | | | | | | |

TABLE 2-continued

Representative compounds and data

| Structure | CK2: % inh 500 nM | CK2: IC$_{50}$ (uM) | HCT-116 (uM) | K562 (uM) | MV-4-11 (uM) | Mia-PaCa (uM) | Bx-PC3 (uM) | MDA-MB231 (uM) | PC3 (uM) | Pan C1 (uM) | Jurkat (uM) |
|---|---|---|---|---|---|---|---|---|---|---|---|
| 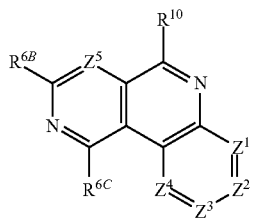 | 99 | | | | | | | | | | |

EXAMPLE 22

Exemplary Embodiments of the Invention

Some representative embodiments of the invention are set forth hereafter, but are not to be taken as limiting the scope of the invention as described herein.

Embodiments

A1. A Compound of Formula (I):

(I)

and pharmaceutically acceptable salts, esters, and tautomers thereof; wherein:

each $Z^1$, $Z^2$, $Z^3$, and $Z^4$ is N, CH, or $CR^3$, provided that none, one or two of $Z^1$, $Z^2$, $Z^3$, and Z are N; and further provided that one or more of $Z^1$, $Z^2$, $Z^3$, and $Z^4$ is $CR^3$;

each $R^3$ is independently an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^3$ is independently halo, $CF_3$, CFN, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, COOH, polar substituent, carboxy bioisostere, $CONR_2$, OOCR, COR, or $NO_2$;

$Z^5$ is $CR^{6A}$ or N;

each of $R^{6A}$, $R^{6B}$ and $R^{6C}$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each of $R^{6A}$, $R^{6B}$ and $R^{6C}$ can be halo, $CF_3$, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, $CONR_2$, OOCR, COR, or $NO_2$;

wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', NR'$_2$, SR', $SO_2R$, $SO_2NR'_2$, $NR'SO_2R$, NR'CONR'$_2$, NR'COOR', NR'COR', CN, COOR', CONR'$_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S; and $R^{10}$ is an optionally substituted five-membered or six-membered carbocyclic or heterocyclic aromatic ring.

A2. The compound of embodiment A1, wherein $Z^5$ is N.

A3. The compound of embodiment A1, wherein $Z^5$ is $CR^{6A}$.

A4. The compound of embodiment A1, A2, or A3, wherein at least one $R^3$ is a polar substituent, wherein said polar substituent is a carboxylic acid, carboxylate salt, ester, carboxamide, tetrazole or carboxy bioisostere.

A5. The compound of any one of embodiments A1-A4, wherein each of each $Z^1$, $Z^3$ and $Z^4$ is CH, and $Z^2$ is $CR^3$, where $R^3$ is a carboxylic acid, carboxylate salt, ester, carboxamide, tetrazole or carboxy bioisostere.

A6. The compound of any one of embodiments A1-A4, wherein at least one of $Z^1$-$Z^4$ is N.

A7. The compound of any one of embodiments A1-A6, wherein $R^{10}$ is an optionally substituted six-membered carbocyclic or heterocyclic aromatic ring.

A8. The compound of embodiment A7, wherein $R^{10}$ is an optionally substituted phenyl or pyridyl ring.

A9. The compound of embodiment A8, wherein $R^{10}$ is phenyl optionally substituted with one or more halo, CN, $C_{1-4}$ alkyl, $C_{1-4}$ alkoxy, $NH_2$, or NHAc substituents.

A10. The compound of any one of embodiments A1-A6, wherein $R^{10}$ is an optionally substituted five-membered heterocyclic aromatic ring.

A11. The compound of embodiment A10, wherein $R^{10}$ is an optionally substituted pyrazole, isoxazole or thiophene ring.

A12. The compound of any one of embodiments A1-A11, wherein at least one of $R^{6B}$ or $R^{6C}$ is H.

A13. The compound of any one of embodiments A1-A12, wherein $R^{6B}$ and $R^{6C}$ are H.

A14. The compound of any one of embodiments A1-A12, wherein $R^{6B}$ is H, SR, $SO_2R$ or $NR_2$, where each R is independently H or $C_{1-4}$ alkyl.

A15. The compound of any one of embodiments A3-A14, wherein $R^{6A}$ is H.

B1. The compound of embodiment A1 having the structure of Formula (III), (IV), (V), or (VI):

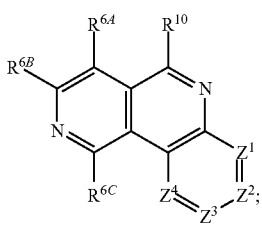
(III)

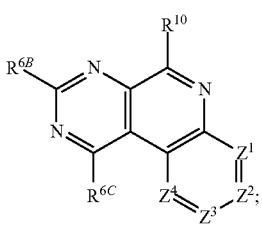
(IV)

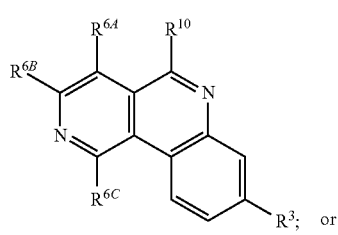
(V)

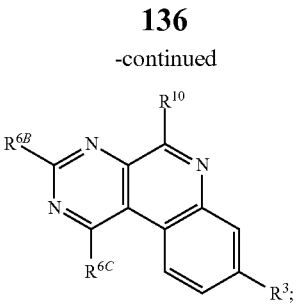
(VI)

and pharmaceutically acceptable salts, esters, and tautomers thereof.

B2. The compound of embodiment B1, wherein at least one $R^3$ is a polar substituent, wherein said polar substituent is a carboxylic acid, carboxylate salt, ester, carboxamide, tetrazole or carboxy bioisostere.

B3. The compound of embodiment B1 or B2, wherein:
the compound has the Formula (III) or (IV) and each of each $Z^1$, $Z^3$ and $Z^4$ is CH, and $Z^2$ is $CR^3$;
or the compound has the Formula (V) or (VI); and
$R^3$ is a carboxylic acid, carboxylate salt, ester, carboxamide, tetrazole or carboxy bioisostere.

B4. The compound of embodiment B1 or B2, wherein at least one of Z-$Z^4$ is N.

B5. The compound of any one of embodiments B1-B4, wherein $R^{10}$ is an optionally substituted six-membered carbocyclic or heterocyclic aromatic ring.

B6. The compound of embodiment B5, wherein $R^{10}$ is an optionally substituted phenyl or pyridyl ring.

B7. The compound of embodiment B6, wherein $R^{10}$ is phenyl optionally substituted with one or more halo, CN, $C_{1-4}$ alkyl, $C_{1-4}$ alkoxy, $NH_2$, or NHAc substituents.

B8. The compound of embodiment B5, wherein $R^{10}$ is an optionally substituted five-membered heterocyclic aromatic ring.

B9. The compound of embodiment B8, wherein $R^{10}$ is an optionally substituted pyrazole, isoxazole or thiophene ring.

B10. The compound of any one of embodiments B1-B9, wherein at least one of $R^{6B}$ or $R^{6C}$ is H.

B11. The compound of any one of embodiments B1-B10, wherein $R^{6B}$ and $R^{6C}$ are H.

B12. The compound of any one of embodiments B1-B10, wherein $R^{6B}$ is H, SR, $SO_2R$ or $NR_2$, where each R is independently H or $C_{1-4}$ alkyl.

B13. The compound of any one of embodiments B1-B12 having Formula (III) or (V), wherein $R^{6A}$ is H.

C1. A compound of Formula (II):

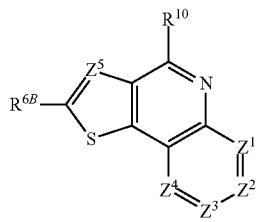
(II)

and pharmaceutically acceptable salts, esters, and tautomers thereof; wherein:
each $Z^1$, $Z^2$, $Z^3$, and $Z^4$ is N, CH, or $CR^3$, provided that none, one or two of $Z^1$, $Z^2$, $Z^3$, and $Z^4$ are N; and further provided that one or more of $Z^1$, $Z^2$, $Z^3$, and $Z^4$ is $CR^3$;

each $R^3$ is independently an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^3$ is independently halo, $CF_3$, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, COOH, polar substituent, carboxy bioisostere, $CONR_2$, OOCR, COR, or $NO_2$;

$Z^5$ is $CR^{6A}$ or N;

each of $R^{6A}$ and $R^{6B}$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each of $R^{6A}$ and $R^{6B}$ can be halo, $CF_3$, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, $CONR_2$, OOCR, COR, or $NO_2$;

wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR, $SO_2R$, $SO_2NR'_2$, $NR'SO_2R'$, $NR'CONR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S; and $R^{10}$ is an optionally substituted five-membered or six-membered carbocyclic or heterocyclic aromatic ring.

C2. The compound of embodiment C1, wherein $Z^5$ is N.

C3. The compound of embodiment C1, wherein $Z^5$ is $CR^{6A}$.

C4. The compound of embodiment C1, C2, or C3, wherein at least one $R^3$ is a polar substituent, wherein said polar substituent is a carboxylic acid, carboxylate salt, ester, carboxamide, tetrazole or carboxy bioisostere.

C5. The compound of any one of embodiments C1-C4, wherein each of each $Z^1$, $Z^3$ and $Z^4$ is CH, and $Z^2$ is $CR^3$, where $R^3$ is a carboxylic acid, carboxylate salt, ester, carboxamide, tetrazole or carboxy bioisostere.

C6. The compound of any one of embodiments C1-C4, wherein at least one of $Z^1$-$Z^4$ is N.

C7. The compound of any one of embodiments C1-C6, wherein $R^{10}$ is an optionally substituted six-membered carbocyclic or heterocyclic aromatic ring.

C8. The compound of embodiment C7, wherein $R^{10}$ is an optionally substituted phenyl or pyridyl ring.

C9. The compound of embodiment C7, wherein $R^{10}$ is an optionally substituted five-membered heterocyclic aromatic ring.

C10. The compound of embodiment C9, wherein $R^{10}$ is an optionally substituted pyrazole, isoxazole or thiophene ring.

C11. The compound of any one of embodiments C1-C10, wherein $Z^5$ is $R^{6A}$ and $R^{6A}$ is H.

C12. The compound of any one of embodiments C1-C10, wherein $Z^5$ is N.

C13. The compound of any one of embodiments C1-C10, wherein $R^{6B}$ is H, halo, or $NR_2$, where each R is independently H or $C_{1-4}$ alkyl.

D1. A pharmaceutical composition comprising a compound of any one of embodiments A1-A15 and a pharmaceutically acceptable excipient.

D2. A pharmaceutical composition comprising a compound of any one of embodiments B1-B13 and a pharmaceutically acceptable excipient.

D3. A pharmaceutical composition comprising a compound of any one of embodiments C1-C13 and a pharmaceutically acceptable excipient.

E1. A method for identifying a candidate molecule that interacts with a casein kinase 2 (CK2) protein, which method comprises:
    contacting a composition containing a CK2 protein and a compound having a structure of Formula (I), (II), (III), (IV), (V), or (VI) with a candidate molecule under conditions in which the compound and the protein interact, and
    determining whether the amount of the compound that interacts with the protein is modulated relative to a control interaction between the compound and the protein without the candidate molecule, whereby a candidate molecule that modulates the amount of the compound interacting with the protein relative to the control interaction is identified as a candidate molecule that interacts with the protein.

E2. The method of embodiment E1, wherein the CK2 protein comprises the amino acid sequence of SEQ ID NO: 1, SEQ ID NO:2 or SEQ ID NO:3, or a substantially identical variant thereof.

E3. The method of embodiment E1 or E2, wherein the protein is in a cell.

E4. The method of embodiment E1 or E2, wherein the protein is in a cell-free system.

E5. The method of any one of embodiments E1-E4, wherein the protein, the compound or the molecule is in association with a solid phase.

E6. The method of any one of embodiments E1-E5, wherein the interaction between the compound and the protein is detected via a detectable label.

E7. The method of any one of embodiments E1-E5, wherein the interaction between the compound and the protein is detected without a detectable label.

F1. A method for modulating the activity of a CK2 protein, which method comprises contacting a system comprising the protein with a compound having a structure of Formula (I), (II), (III), (IV), (V), or (VI) in an amount effective for modulating the activity of the protein.

F2. The method of embodiment F1, wherein the activity of the protein is inhibited.

F3. The method of embodiment F1 or F2, wherein the CK2 protein comprises the amino acid sequence of SEQ ID NO: 1, SEQ ID NO:2 or SEQ ID NO:3, or a substantially identical variant thereof.

F4. The method of embodiment F1, F2 or F3, wherein the system is a cell.

F5. The method of embodiment F1, F2 or F3, wherein the system is a cell-free system.

F6. The method of any one of embodiments F1-F5, wherein the protein, the compound or the molecule is in association with a solid phase.

G1. A method for inhibiting cell proliferation, which method comprises contacting cells with a compound having a structure of Formula (I), (II), (III), (IV), (V), or (VI) in an amount effective to inhibit proliferation of the cells.

G2. The method of embodiment G1, wherein the cells are in a cancer cell line.

G3. The method of embodiment G2, wherein the cancer cell line is a breast cancer, prostate cancer, pancreatic cancer, lung cancer, hemopoietic cancer, colorectal cancer, skin cancer, or ovary cancer cell line.

G4. The method of embodiment G1, G2 or G3, wherein the cells are in a tumor in a subject.

G5. The method of any one of embodiments G1-G4, wherein contacting cells with a compound having a structure of Formula (I), (II), (III), (IV), (V), or (VI) induces cell apoptosis.

G6. The method of embodiment G1, wherein the cells are from an eye of a subject having macular degeneration.

G7. The method of embodiment G1, wherein the cells are in a subject having macular degeneration.

H1. A method for treating a condition related to aberrant cell proliferation, which method comprises administering a compound having a structure of Formula (I), (II), (III), (IV), (V), or (VI) to a subject in need thereof in an amount effective to treat the cell proliferative condition.

H2. The method of embodiment Hi, wherein the cell proliferative condition is a tumor-associated cancer.

H3. The method of embodiment H2, wherein the cancer is of the colorectum, breast, ovary, lung, liver, pancreas, lymph node, colon, prostate, brain, head and neck, skin, liver, kidney, blood and heart.

H4. The method of embodiment Hi, wherein the cell proliferative condition is a non-tumor cancer.

H5. The method of embodiment H4, wherein the non-tumor cancer is a hematopoietic cancer.

H6. The method of embodiment Hi, wherein the cell proliferative condition is macular degeneration.

J1. A method for identifying a candidate molecule that interacts with a protein kinase, which comprises:
contacting a composition containing a protein kinase and a compound having a structure of Formula (I), (II), (III), (IV), (V), or (VI) under conditions in which the compound and the protein interact with a candidate molecule, and
determining whether the amount of the compound that interacts with the protein kinase is modulated relative to a control interaction between the compound and the protein kinase without the candidate molecule,
whereby a candidate molecule that modulates the amount of the compound interacting with the protein kinase relative to the control interaction is identified as a candidate molecule that interacts with the protein kinase.

J2. The method of embodiment J1, wherein the protein kinase is serine-threonine protein kinase or a tyrosine protein kinase.

J3. The method of embodiment J1 or J2, wherein the protein kinase is a human serine-threonine protein kinase or a human tyrosine protein kinase.

J4. The method of embodiment J1, J2, or J3, wherein the protein kinase is a human serine-threonine protein kinase selected from the group consisting of CK2, CK2α2, PIM1, PIM2, PIM3, CDK1/cyclinB, c-RAF, Mer, MELK, HIPK3, HIPK2 and ZIPK.

J5. The method of embodiment J2, wherein the protein kinase is a serine-threonine protein kinase which contains one or more of the following amino acids at positions corresponding to those listed in human CK2: leucine at position 45, methionine at position 163 and isoleucine at position 174.

J6. The method of embodiment J5, wherein the serine threonine protein kinase is selected from the group consisting of CK2, STK10, HIPK2, HIPK3, DAPK3, DYK2 and PIM-1.

J7. The method of embodiment J1, J2, or J3, wherein the protein kinase is a human tyrosine protein kinase selected from the group consisting of FLT1, FLT2, FLT3, FLT3 (D835Y), and FLT4.

J8. The method of any one of embodiments J1-J7, wherein the protein, the compound or the molecule is in association with a solid phase.

J9. The method of any one of embodiments J1-J8, wherein the interaction between the compound and the protein is detected via a detectable label.

J10. The method of any one of embodiments J1-J9, wherein the protein kinase activity is the transfer of a gamma phosphate from adenosine triphosphate to a peptide or protein substrate.

K1. A method for modulating a protein kinase activity, which comprises contacting a system comprising a protein kinase protein with a compound of Formula (I), (II), (III), (IV), (V), or (VI) in an amount effective for modulating the activity of the protein kinase.

K2. The method of embodiment K1, wherein the protein kinase is serine-threonine protein kinase or a tyrosine protein kinase.

K3. The method of embodiment K2, wherein the protein kinase is a human serine-threonine protein kinase or a human tyrosine protein kinase.

K4. The method of embodiment K3, wherein the protein kinase is a human serine-threonine protein kinase selected from the group consisting of CK2, C2α2, PIM1, PIM2, PIM3, CDK1/cyclinB, c-RAF, Mer, MELK, HIPK3, HIPK2 and ZIPK.

K5. The method of embodiment K2, wherein the protein kinase is a human tyrosine protein kinase selected from the group consisting of FLT1, FLT2, FLT3, FLT3 (D835Y), and FLT4.

L1. A method for treating pain or inflammation in a subject, which comprises administering a compound of Formula (I), (II), (III), (IV), (V), or (VI) to a subject in need thereof in an amount effective to treat the pain or the inflammation.

M1. A method for inhibiting angiogenesis in a subject, which comprises administering a compound of Formula (I), (II), (III), (IV), (V), or (VI) to a subject in need thereof in an amount effective to inhibit the angiogenesis.

N1. A composition of matter comprising a protein kinase and a compound of Formula (I), (II), (III), (IV), (V), or (VI).

N2. The composition of embodiment N1, wherein the protein kinase is a human serine-threonine kinase or a human tyrosine kinase.

N3. The composition of embodiment N2, wherein the protein kinase is selected from the group consisting of CK2, C2α2, PIM1, PIM2, PIM3, CDK1/cyclinB, c-RAF, Mer, MELK, HIPK3, HIPK2, ZIPK, FLT1, FLT2, FLT3, FLT3 (D835Y), and FLT4.

P1. A compound of Formula (I), (II), (III), (IV), (V), or (VI) which is a compound in one of the Tables provided herein or a pharmaceutically acceptable salt thereof.

Q1. A compound of Formula (I), selected from the group consisting of:
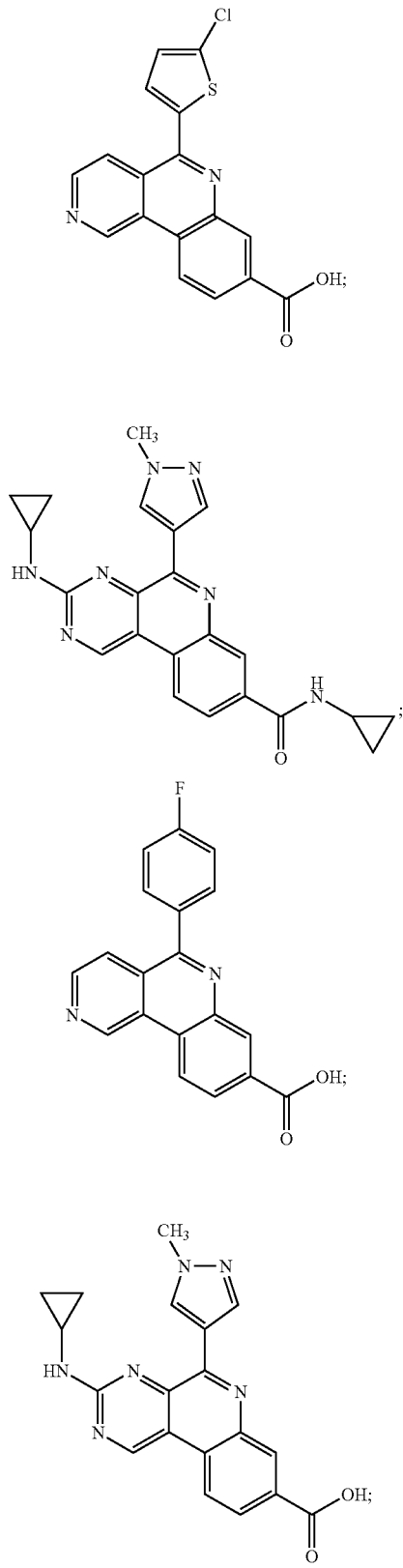
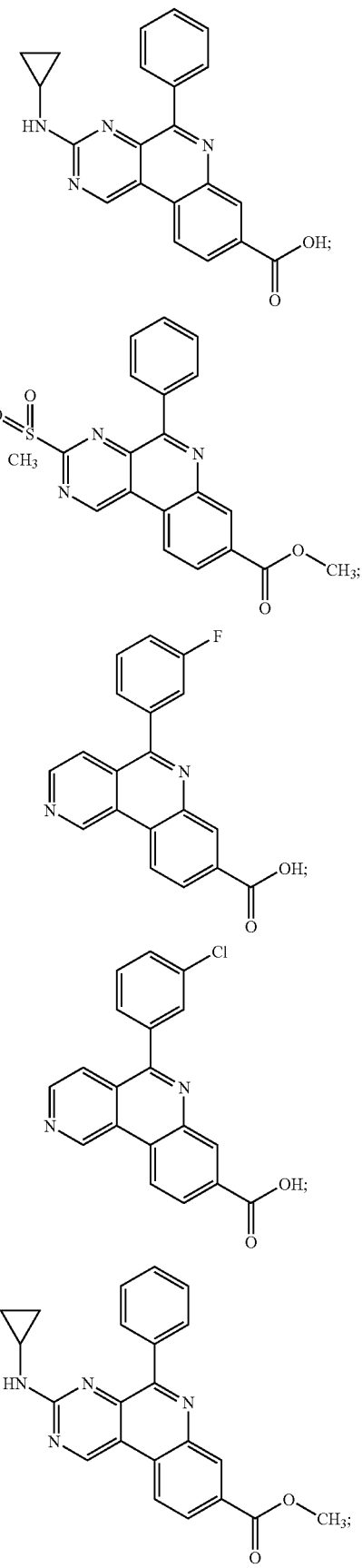

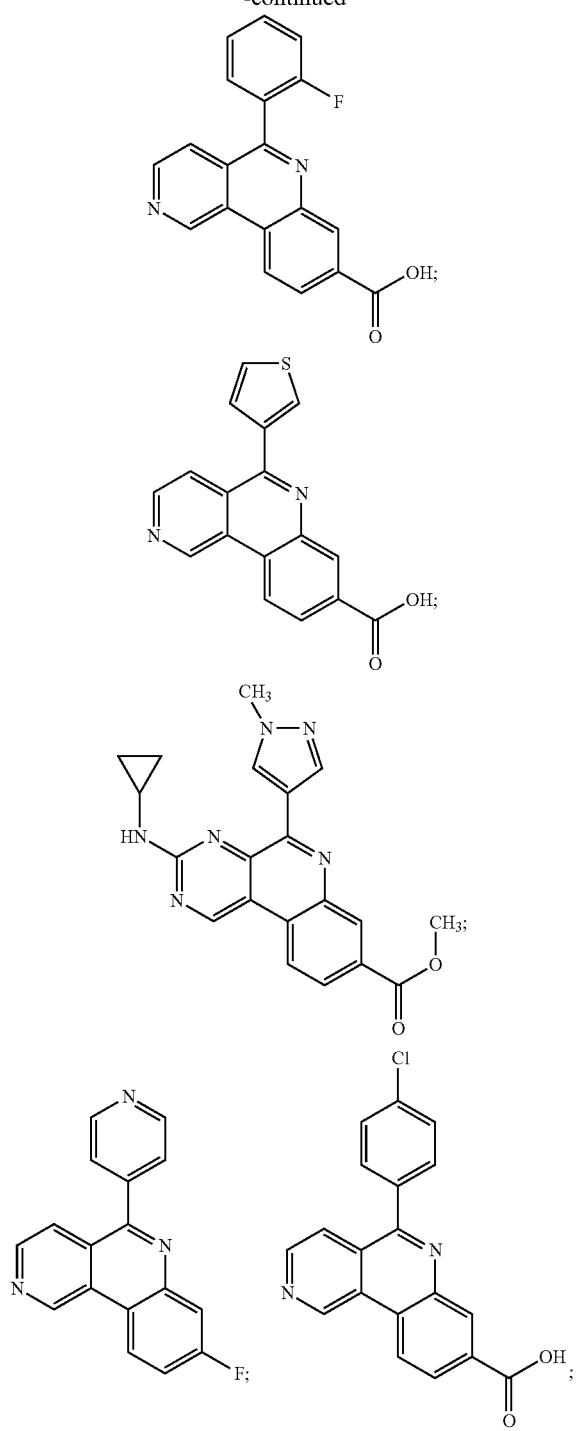
or a pharmaceutically acceptable salt thereof.

The invention claimed is:

1. A compound of Formula (I):

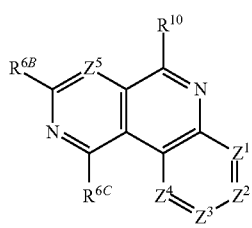

and pharmaceutically acceptable salts, esters, and tautomers thereof; wherein:
each $Z^1$, $Z^3$, and $Z^4$ is CH;
$Z^2$ is $CR^3$;
each $R^3$ is independently an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or
each $R^3$ is independently halo, $CF_3$, CFN, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, COOH, polar substituent, carboxy bioisostere, $CONR_2$, OOCR, COR, or $NO_2$;
$Z^5$ is $CR^{6A}$;
each of $R^{6A}$, $R^{6B}$ and $R^{6C}$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group,
or each of $R^{6A}$, $R^{6B}$ and $R^{6C}$ can be halo, $CF_3$, OR, $NR_2$, NROR, $NRNR_2$, SR, SOR, $SO_2R$, $SO_2NR_2$, $NRSO_2R$, $NRCONR_2$, NRCOOR, NRCOR, CN, COOR, $CONR_2$, OOCR, COR, or $NO_2$;
wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl,
and wherein two R on the same atom or on adjacent atoms can be linked to form a 3-8 membered ring, optionally containing one or more N, O or S;
and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$,
wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;
and wherein two R' can be linked to form a 3-7 membered ring optionally containing up to three heteroatoms selected from N, O and S; and
$R^{10}$ is an optionally substituted five-membered or six-membered carbocyclic or heterocyclic aromatic ring.

2. The compound of claim 1, wherein at least one $R^3$ is a polar substituent, wherein said polar substituent is a carboxylic acid, carboxylate salt, ester, carboxamide, tetrazole or carboxy bioisostere.

3. The compound of claim 1, wherein $Z^2$ is $CR^3$, where $R^3$ is a carboxylic acid, carboxylate salt, ester, carboxamide, tetrazole or carboxy bioisostere.

4. The compound of claim 1, wherein $R^{10}$ is an optionally substituted six-membered carbocyclic or heterocyclic aromatic ring.

5. The compound of claim 4, wherein $R^{10}$ is an optionally substituted phenyl or pyridyl ring.

6. The compound of claim 5, wherein $R^{10}$ is phenyl optionally substituted with one or more halo, CN, $C_{1-4}$ alkyl, $C_{1-4}$ alkoxy, $NH_2$, or NHAc substituents.

7. The compound of claim 1, wherein $R^{10}$ is an optionally substituted five-membered heterocyclic aromatic ring.

8. The compound of claim 7, wherein $R^{10}$ is an optionally substituted pyrazole, isoxazole or thiophene ring.

9. The compound of claim 1, wherein at least one of $R^{6B}$ or $R^{6C}$ is H.

10. The compound of claim 1, wherein $R^{6B}$ and $R^{6C}$ are H.

11. The compound of claim 1, wherein $R^{6A}$ is H.

12. The compound of claim 1 having the structure of Formula (V):

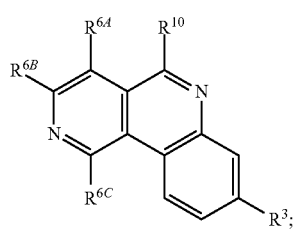

and pharmaceutically acceptable salts, esters, and tautomers thereof.

13. A pharmaceutical composition comprising a compound of claim 1 and a pharmaceutically acceptable excipient.

14. A composition of matter comprising a protein kinase and a compound of Formula (I) or (V).

15. The composition of claim 14, wherein the protein kinase is a human serine-threonine kinase or a human tyrosine kinase.

16. The composition of claim 15, wherein the protein kinase is selected from the group consisting of CK2, CK2∀2, PIM1, PIM2, PIM3, CDK1/cyclinB, c-RAF, Mer, MELK, HIPK3, HIPK2, ZIPK, FLT1, FLT2, FLT3, FLT3 (D835Y), and FLT4.

17. A compound of Formula (I), selected from the group consisting of:

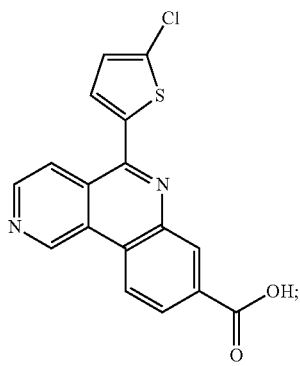

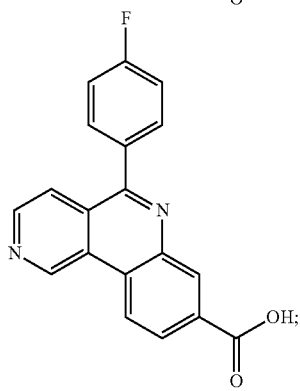

-continued

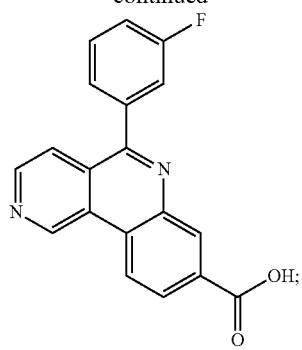

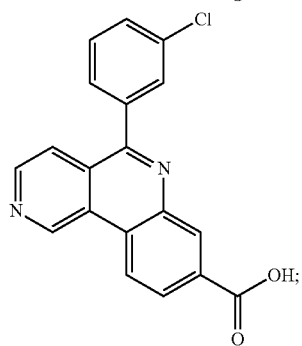

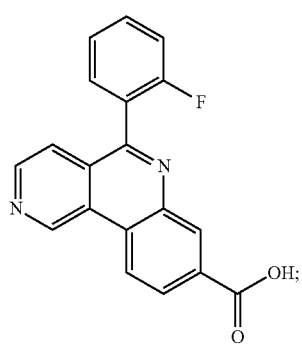

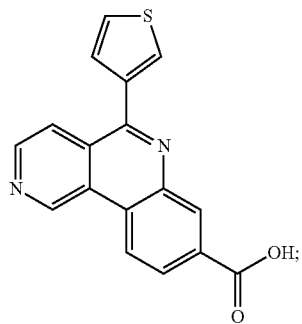

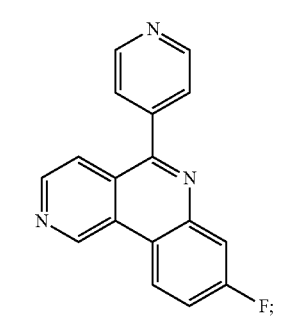

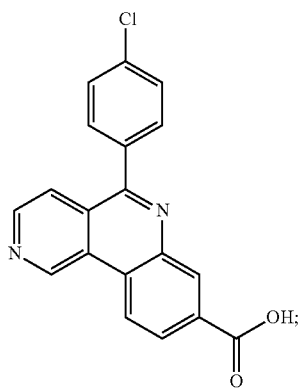
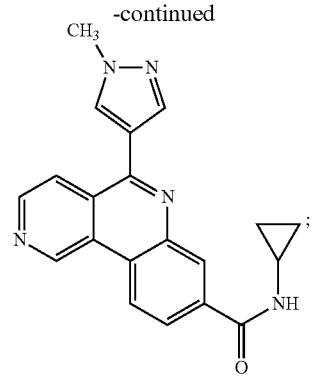
or a pharmaceutically acceptable salt thereof.
* * * * *